US008044265B2

(12) United States Patent
Landouar-Arsivaud et al.

(10) Patent No.: US 8,044,265 B2
(45) Date of Patent: Oct. 25, 2011

(54) GENE PROMOTORS WHICH CAN BE USED IN PLANTS

(75) Inventors: Lucie Landouar-Arsivaud, Montils (FR); Remi Lemoine, Poitiers (FR)

(73) Assignees: Vilmorin & Cie, Paris (FR); Centre National de la Recherche Scientifique, Paris (FR); Universite de Poitiers, Poiters (FR)

(*) Notice: Subject to any disclaimer, the term of this patent is extended or adjusted under 35 U.S.C. 154(b) by 0 days.

(21) Appl. No.: 12/087,440

(22) PCT Filed: Jan. 5, 2007

(86) PCT No.: PCT/FR2007/000014
§ 371 (c)(1),
(2), (4) Date: Nov. 10, 2008

(87) PCT Pub. No.: WO2007/077398
PCT Pub. Date: Jul. 12, 2007

(65) Prior Publication Data
US 2009/0276917 A1   Nov. 5, 2009

(30) Foreign Application Priority Data
Jan. 6, 2006   (FR) .................................. 06 00137

(51) Int. Cl.
*A01H 1/00*   (2006.01)
*C07H 21/04*   (2006.01)
*C12N 15/00*   (2006.01)

(52) U.S. Cl. ........ 800/295; 435/6.1; 435/69.1; 435/468; 435/419; 435/320.1; 536/24.1; 800/278

(58) Field of Classification Search ............. 435/6, 69.1, 435/468, 419, 320.1, 6.1; 536/24.1; 800/278, 800/295; 530/370
See application file for complete search history.

(56) References Cited

OTHER PUBLICATIONS

Muzny et al., GenEmbl Database, Direct submission, Acc. No. AC114245, Oct. 9, 2002, See Result 6.*
International Search Report issued by the International Searching Authority (ISA/EPO) on Jul. 12, 2007 in connection with International Application No. PCT/FR2007/000014.
Zamski E., et al. "Analysis of celery (*Apium graveolens*) mannitol dehydrogenase (*Mtd*) promoter regulation in *Arabidopsis* suggests roles for MTD in key environmental and metabolic responses" Plant Molecular Biology, 2001, 47:621-631.
Genbank Accession No. AF067082, Sep. 30, 1998.
WO 02/04647 A1 (Centre National De La Recherche Scientifique) Jan. 17, 2002.
Noiraud N., et al. "Identification of a Mannitol Transporter, AgMaT1, in Celery Phloem" The Plant Cell, Mar. 2001, vol. 13, pp. 695-705.
EMBL Accession No. Q8RVQ2, Jun. 1, 2002.
Noiraud N., et al. "The Sucrose Transporter of Celery. Identification and Expression during Salt Stress" Plant Physiology, Apr. 2000, vol. 122, pp. 1447-1455.

GENESEQ Accession No. ACL37108, Jun. 2, 2005.
WO 00/53763 A1 (Pioneer Hi-Bred International, Inc.) Sep. 14, 2000.
Divot F., et al. "Systemic response to aphid infestation by *Myzus persicae* in the phloem of *Apium graveolens*" Plant Molecular Biology, 2005, 57:517-540.
Bohnert H.J., et al. "A genomics approach towards salt stress tolerance" Plant Physiol. Biochem., 2001, 39:295-311.
Busk P.K. and Pages M. "Regulation of abscisic acid-induced transcription" Plant Molecular Biology, 1998, 37:425-435.
Chatthai M., et al. "The isolation of a novel metallothionein-related cDNA expressed in somatic and zygotic embryos of Douglas-fir: regulation by ABA, osmoticum, and metal ions" Plant Molecular Biology, 1997, 34: 243-254.
Choi H., et al. "ABFs, a Family of ABA-responsive Element Binding Factors" The Journal of Biological Chemistry, 2000, 275(3):1723-1730.
Choi D., et al. "Molecular Cloning of a Metallothionein-Like Gene from *Nicotiana glutinosa* L. and its Induction by Wounding and Tobacco Mosaic Virus Infection" Plant Physiol., 1996, 112:353-359.
De Pascale S., et al. "Growth, Water Relations, and Ion Content of Field-grown Celery [*Apium graveolens* L. var. *dulce* (Mill.)Pers.] under Saline Irrigation" J. Amer. Soc. Hort. Sci., 2003, 128(1):136-143.
Eulgem T., et al. "The WRKY superfamily of plant transcription factors" Trends in Plant Science, May 2000, 5(5):199-206.
Fromard L., et al. "Control of Vascular Sap pH by the Vessel-Associated Cells in Woody Species" Plant Physiol., 1995, 108:913-918.
Hasegawa P.M., et al. "The dawn of plant salt tolerance genetics" Trends in Plant Science, Aug. 2000, 5(8):317-319.
Hasegawa P.M., et al. "Plant Cellular and Molecular Responses to High Salinity" Annu. Rev. Plant Physiol. Plant Mol. Biol., 2000, 51:463-499.
Kang J.Y., et al. "*Arabidopsis* Basic Leucine Zipper Proteins That Mediate Stress-Responsive Abscisic Acid Signaling" The Plant Cell, Feb. 2002, 14:343-357.
Karakas B., et al. "Salinity and drought tolerance of mannitol-accumulating transgenic tobacco" Plant, Cell and Environment, 1997, 20:609-616.
Koyama M.L., et al. "Quantitative Trait Loci for Component Physiological Traits Determining Salt Tolerance in Rice" Plant Physiology, Jan. 2001, 125:406-422.
Kreps J.A., et al. "Transcriptome Changes for *Arabidopsis* in Response to Salt, Osmotic, and Cold Stress" Plant Physiology, Dec. 2002, 130:2129-2141.
Lohaus G., et al. "Solute balance of a maize (*Zea mays* L.) source leaf as affected by salt treatment with special emphasis on phloem retranslocation and ion leaching" Journal of Experimental Botany, Oct. 2000, 51(351):1721-1732.
Lu C.A., et al. "Three Novel MYB Proteins with One DNA Binding Repeat Mediate Sugar and Hormone Regulation of α—Amylase Gene Expression" The Plant Cell, Aug. 2002, 14:1963-1980.

(Continued)

*Primary Examiner* — Phuong T Bui
(74) *Attorney, Agent, or Firm* — John P. White; Cooper & Dunham LLP

(57) ABSTRACT

The present invention relates to nucleic acid sequences which have a transcriptional promoter activity preferentially in the phloem of plants under conditions of stress, or in the roots, to derived sequences, to constructs containing such sequences, and also to cells transformed with said constructs and to transgenic plants. The present invention makes it possible to place any transgene under the transcriptional control of a promoter, the activity of which is tissue-specific, organ-specific and/or inducible by environmental factors, such as biotic or abiotic stresses.

23 Claims, 25 Drawing Sheets

OTHER PUBLICATIONS

Figure 1:
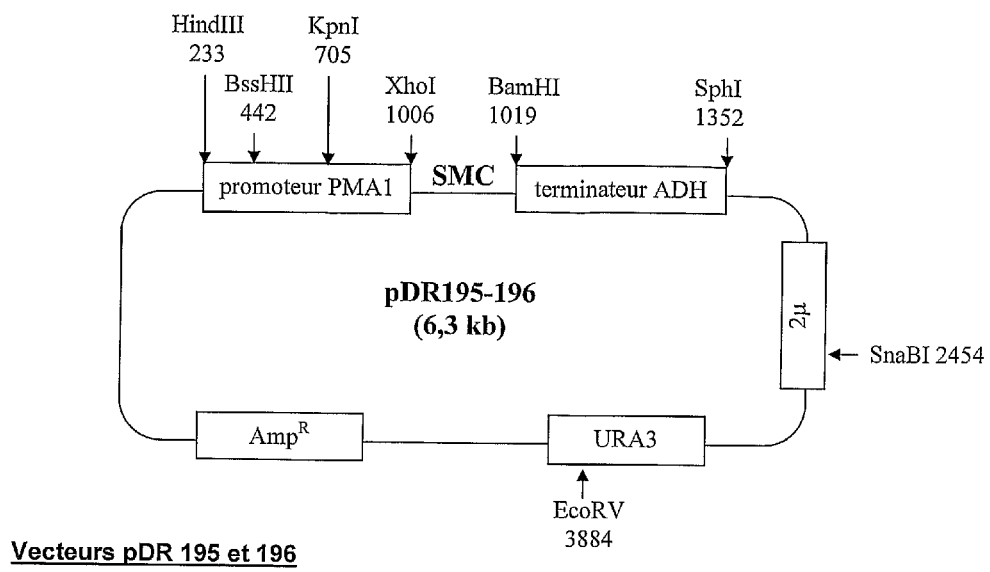
Figure 1:
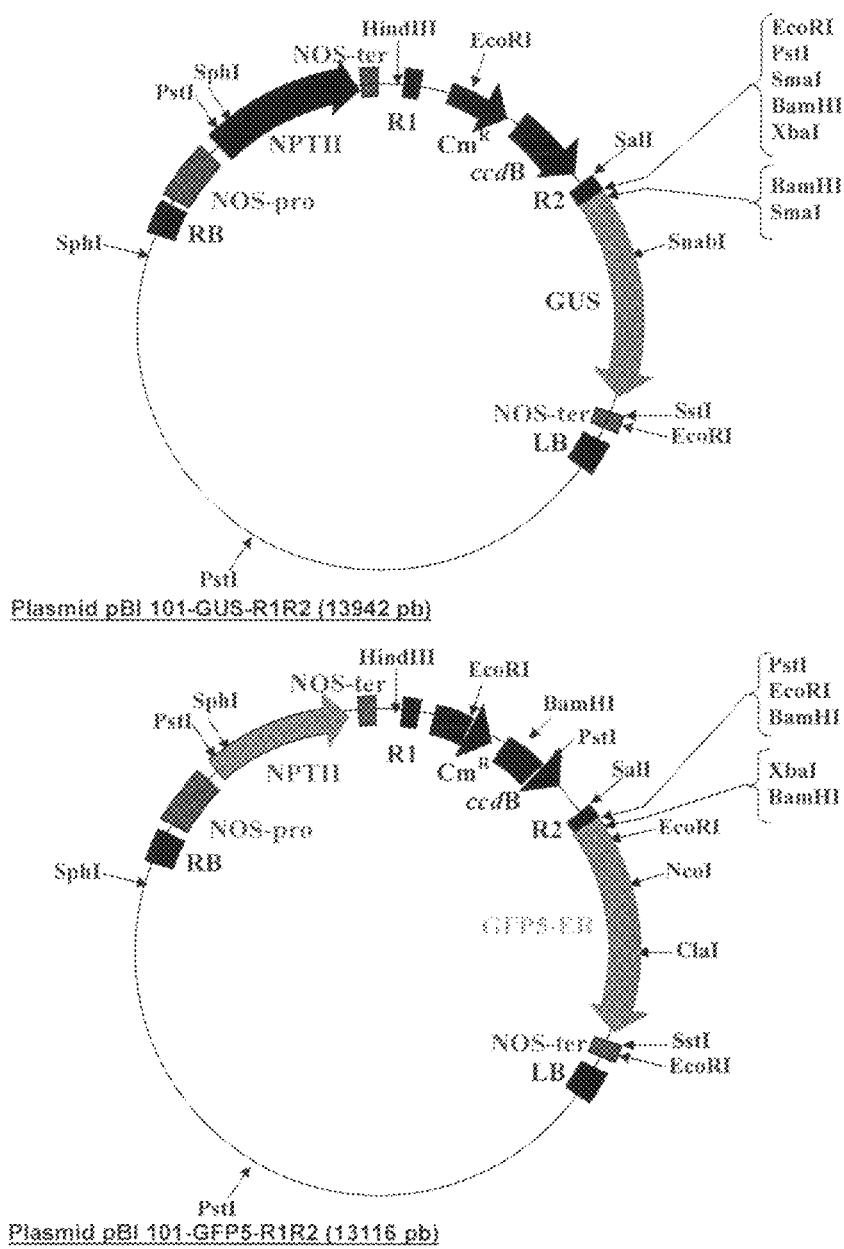

Masmoudi K., et al. "Isolation and characterization of a differentially expressed sequence tag from *Triticum durum* salt-stressed roots" Plant Physiol. Biochem., 2001, 39:971-979.

Morita A., et al. "Functional dissection of a sugar-repressed α-amylase gene (*RAmy1A*) promoter in rice embryos" FEBS Letters, 1998, 423:81-85.

Noiraud N., et al. "Transport of polyols in higher plants" Plant Physiol. Biochem., 2001, 39:717-728.

Popova O.V., et al. "Salt-dependent expression of a nitrate transporter and two amino acid transporter genes in *Mesembtyanthemum crystallinum*" Plant Molecular Biology, 2003, 52:569-578.

Salekdeh G.H., et al. "A proteomic approach to analyzing drought- and salt-responsiveness in rice" Field Crops Research, 2002, 76:199-219.

Shen B., et al. "Increased Resistance to Oxidative Stress in Transgenic Plants by Targeting Mannitol Biosynthesis to Chloroplasts" Plant Physiol., 1997, 113:1177-1183.

Shen B., et al. "Mannitol Protects against Oxidation by Hydroxyl Radicals" Plant Physiol.; 1997, 115:527-532.

Sugimoto K., et al. "Transcriptional activation mediated by binding of a plant GATA-type zinc finger protein AGP1 to the AG-motif (AGATCCAA) of the wound-inducible *Myb* gene *NtMyb2*" The Plant Journal, 2003, 36:550-564.

Tarczynski M.C., et al. "Stress Protection of Transgenic Tobacco by Production of the Osmolyte Mannitol" Science, 1993, 259:508-510.

Teakle G.R., et al. "*Arabidopsis thaliana* GATA factors: organization, expression and DNA-binding characteristics" Plant Molecular Biology, 2002, 50:43-57.

Urao T., et al. "An *Arabidopsis myb* Homolog is Induced by Dehydration Stress and its Gene Product Binds to the Conserved MYB Recognition Sequence" The Plant Cell, 1993, 5:1529-1539.

Vilaine F., et al. "Towards deciphering phloem: a transcriptome analysis of the phloem of *Apium graveolens*" The Plant Journal, 2003, 36:67-81.

Shahmuradov et al., "PlantProm: a database of plant promoter sequences" (2003) Nucleic Acids Res. (2003) 31(1):114-117.

Communication pursuant to Article 94(3) EPC, including an Examination Report, dated Apr. 20, 2011 and issued by the European Patent Office in connection with European Patent Application No. 07 712 640.7.

GeneSeq Accession No. ACI49108, Human microarray DNA oligonucleotide SEQ ID No. 49099 of U.S. Patent Application Publication No. US 2003/0104410 A1, published Jun. 5, 2003 to Mittmann [cited in Examination Report dated Apr. 20, 2011, issued by the European Patent Office in connection with European Patent Application No. 07 712 640.7].

OeneSeq Accession No. AJJ48225, Viral regulatory mlRNA SEQ ID No. 200545 of PCT International Publication No. WO 2004/048511 A2, published Jun. 10, 2004 to Bentwich [cited in Examination Report dated Apr. 20, 2011, issued by the European Patent Office in connection with European Patent Application No. 07 712 640.7].

\* cited by examiner

Vecteurs pDR 195 et 196

```
AAAATGTTTCATATTCACAAAAGAAATTTTGAACAGAAACAATTGTGGATGCACCTCTCTATATATTTGTACTTTTGCAT
    -580      -570      -560      -550      -540      -530      -520      -510

ACTGTCGTATATATAGTAAAGAATTACTTAATAGGGGTGAATGTACTCACCGGGCAAAGTATTAGTAATTTCTTCATTAA
    -500      -490      -480      -470      -460      -450      -440      -430

AATATTTAAGAGTCAATTTAATTTGCCACTGCCTTTTCTTTTTCAGTTCTTACTTCAAGGTTAGTCAATCTATTCCGGTG
    -420      -410      -400      -390      -380      -370      -360      -350

AATAATTACGAACGAATATATAATCTCTGAGTAGCAAAGATTCCCAAAACTATCCAAAATTATCCGGCGGCTGCGGATTT
    -340      -330      -320      -310      -300      -290      -280      -270

GATACGATAAAAAAATATCGCTATAATCACAAATTTATTCAAATTTACTAAAAAGGGCCCACAGCCTAATTACCAAAATC
    -260      -250      -240      -230      -220      -210      -200      -190

AAATTGAACTTTCCCAATTCCACGCAATCCTCAAAGATAAACACAGCAACCACCAACTAATACTCTATAAAAAATCATAC
    -180      -170      -160      -150      -140      -130      -120      -110

AAAAGTCCAACTAATTACACCCCTCACGTTACGATAGTCAAATTGTTTAGTCCTTTCCCCCAAGCTTCGACCATTGTTTC
    -100       -90       -80       -70       -60       -50       -40       -30
                                                 M   A   G   T   S   G   P   S   G   G   V   V
TCAACATTTTGTAATCTCTCTCTCTCTCG ATG GCC GGA ACT TCT GGC CCT TCC GGC GGT GTC GTC
     -20       -10         1              10              20              30

A   D   P   K   N   L   S   S   P   L   F   D   A   E   K   K   P   K   N   N
GCC GAT CCC AAG AAT CTG AGT TCA CCT TTA TTT GAC GCG GAG AAA AAA CCC AAA AAT AAC
         40              50              60              70              80              90

K   Y   A   F   A   C   S   I   L   A   S   M   T   S   I   L   L   G   Y
AAG TAT GCT TTT GCT TGT TCC ATT TTA GCT TCC ATG ACT TCA ATT CTA CTT GGT TAT
        100             110             120             130             140             150

GGTACGATGTCTTTCAAACCTACACTTATTTTCAGTACACTCACAATGTCACAAATTCTTCGTAATCGATCTCTCTTCCA
        160             170             180             190             200             210             220             230

CGATCAGTATTTTTATTTTTAATTCAATTTATTAAAGCTTTCGGACAGATCTCTTTAGTTTTACCGACACATATTACATTA
        240             250             260             270             280             290             300             310

GAATAATCTGAACAACACTCTGCATGTCTTTTTGTCTTAACTATCTTATGATCTAAACACTCTACTTGTGTTGTGTTATA
        320             330             340             350             360             370             380             390

D   T   G   V   M   S   G   A   A   I   Y   I   K   K
ACCTTTTCAATTTTTTATTTTTTA GAT ACG GGG GTT ATG AGT GGA GCA GCA ATC TAC ATA AAA AAA
        400             410             420             430             440             450             46

D   L   R   F   T   D   V   Q   I   E   I   I   V   G   I   I   N   I   F   S
GAT CTC CGT TTC ACC GAT GTA CAA ATC GAA ATC ATC GTC GGA ATC ATC AAC ATC TTC TCT
0              470             480             490             500             510             52

L   L   G   S   F   L   A   G   R   T   S   D   W   I   G   R   R   Y   T   M
CTT CTC GGC TCT TTT CTC GCC GGA AGA ACC TCC GAT TGG ATT GGC CGG AGA TAC ACA ATG
0              530             540             550             560             570             58

V   L   A   G   G   I   F   F   A   G   A   F   L   M   G   C   A   T   N   F
GTT CTA GCC GGT GGC ATA TTT TTT GCC GGA GCT TTT TTA ATG GGA TGT GCT ACA AAC TTT
0              590             600             610             620             630             64
```

Figure 8A

```
  E   F   L   M   V   G   R   F   V   A   G   I   G   V   G   Y   A   M   M   I
GAG TTT TTA ATG GTG GGT CGG TTT GTC GCC GGG ATC GGA GTA GGG TAT GCT ATG ATG ATC
0           650         660         670         680         690          70

A   P   V   Y   T   T   E   V   A   P   A   S   S   R   G   F   L   T   S   F
GCT CCG GTT TAT ACA ACT GAG GTT GCT CCG GCG TCT TCT CGG GGT TTT CTC ACT TCT TTC
0           710         720         730         740         750           7

P   E   V   F   I   N   A
CCG GAG GTC TTT ATT AAT GCT GGTGCGTTTTTATTCGCTAATTAATTTATATTTATTTATTTGTATAAA
0           770         780       790       800       810       820       830

TTAGATATAATTTTTAATTTAAATTGAATAAAACTTTACTGTACTAAAGATCAGATAACGTATATCTCGTGCAAATGTTG
      840       850       860       870       880       890       900       910

TGGAACACATCATGAAGATAATAATATTAAGCATATATTAAAATAATGTTTTATTAAAAATATGTGAACTGTTGTTTGGT
      920       930       940       950       960       970       980       990

GTTAACTGCTTTTTTTTATTTGGTGTTCGTGATGTTTTAACAACACTGACCAATATGTAAGTGTGTACAACTTTACCAAC
      1000      1010      1020      1030      1040      1050      1060      1070

AAAAGATACTGTTATTAAAGTACAGATTATGTGAATATTATTTATATAAAATAAAAAAATATGTAGGTCCAGTGAAGCAT
      1080      1090      1100      1110      1120      1130      1140      1150

TTTTCGTCGTTTAGATGTGTGGTCCTTATTGATAGGTAGAGTTGTGTATCTTTTGCTTTTGTACACGTTTACAATAAGAT
      1160      1170      1180      1190      1200      1210      1220      1230

ATTTGGTTGTCAATTTAACAGCTGTATAGCTTTGATGACCTGTGTTATATATTATGTGGTGTACATAGGTTGTGATTGTG
      1240      1250      1260      1270      1280      1290      1300      1310

ATGTTTATCTGATAATTAGTCTGTTTTTATTTGTTATATTTTTGGGTTTGAATTGGTTAACATGTAGTGATGAGTTGTTG
      1320      1330      1340      1350      1360      1370      1380      1390

AACTCGATTTAATTGTATATAGTTGGACAGTTGTGATTACTCGATTTGATCGAATATAATTGGTATTGGACAGTTGTGAT
      1400      1410      1420      1430      1440      1450      1460      1470

TGGTTTTTTTTGGATAATGTTGGCGGCTTTTTCTTGATTATCGTTTGGATGATAATGAAATGTTAATTGTTATTGACATT
      1480      1490      1500      1510      1520      1530      1540      1550

G   V   M   L   G   Y   V   S   N   F   A
ACATGGTAGATGTAACTATGTTGTTTGTTAACA GGA GTT ATG CTG GGG TAT GTA TCC AAC TTT GCA
      1560      1570      1580         1590        1600        1610          16

F   A   K   L   P   L   W   L   G   W   R   F   M   L   G   I   G   A   V   P
TTT GCA AAG CTT CCG CTT TGG TTA GGC TGG AGG TTT ATG CTT GGA ATT GGA GCA GTT CCT
20          1630        1640        1650        1660        1670          16

S   V   G   L   A   I   G   V   L   Y   M   P   E   S   P   R   W   L   V   M
TCG GTT GGC TTA GCC ATT GGT GTA TTG TAT ATG CCT GAG TCT CCG CGT TGG CTT GTC ATG
80          1690        1700        1710        1720        1730          17

R   G   Q   L   G   E   A   R   R   V   L   E   K   T   S   E   S   K   E   E
AGG GGT CAA CTT GGC GAA GCA AGG CGT GTA CTG GAA AAG ACT TCG GAG AGC AAA GAA GAA
40          1750        1760        1770        1780        1790          18

A   R   Q   R   L   E   D   I   K   E   A   A   G   I   P   E   E   C   N   D
GCT CGA CAA AGA CTA GAA GAT ATC AAG GAG GCT GCT GGA ATT CCA GAA GAA TGT AAT GAT
00          1810        1820        1830        1840        1850          18
```

Figure 8B

```
  D   V   V   E   V   P   K   R   S   K   D   D   A   V   W   K   E   L   F   L
GAC GTT GTT GAA GTT CCT AAA CGT AGC AAA GAC GAT GCT GTG TGG AAA GAA TTG TTC CTT
60       1870        1880        1890        1900        1910              19

H   P   T   P   A   V   R   H   A   A   I   T   G   I   G   I   H   F   F   Q
CAT CCT ACA CCA GCT GTT CGC CAT GCT GCT ATC ACT GGC ATT GGT ATT CAT TTC TTC CAA
20       1930        1940        1950        1960        1970              19

M   A   S   G   V   D   A   V   V   L   Y   S   P   R   I   F   E   K   A   G
ATG GCT AGT GGT GTT GAT GCT GTT GTT TTG TAC AGT CCT CGA ATT TTT GAG AAG GCT GGG
80       1990        2000        2010        2020        2030              20

L   K   S   D   N   H   K   L   L   A   T   I   G   V   G   V   C   K   T   I
TTA AAG AGT GAT AAC CAC AAG CTA CTC GCC ACC ATT GGT GTT GGA GTC TGC AAA ACT ATT
40       2050        2060        2070        2080        2090              21

F   V   L   I   S   T   F   L   L   D   K   V   G   R   R   P   L   M   L   S
TTT GTT TTG ATA TCA ACA TTT TTG CTA GAC AAA GTC GGA CGG CGC CCA CTG ATG CTT TCG
00       2110        2120        2130        2140        2150              21

S   M   G   G   M   V   I   A   L   L   V   L   S   G   S   L   S   V   I   N
AGT ATG GGG GGC ATG GTA ATT GCT CTA CTC GTA CTC TCA GGC TCA TTG TCT GTA ATT AAT
60       2170        2180        2190        2200        2210              22

H   S   H   Q   T   V   P   W   A   V   A   L   A   I   I   S   V   Y   G   F
CAC TCG CAT CAA ACC GTT CCC TGG GCT GTT GCT TTG GCA ATA ATT TCG GTG TAT GGC TTT
20       2230        2240        2250        2260        2270              22

V   S   V   F   S   S   G   M   G   P   I   A   W   V   Y   S   S   E   V   F
GTG TCG GTG TTT TCA AGT GGG ATG GGG CCA ATT GCT TGG GTG TAT AGT TCG GAG GTG TTT
80       2290        2300        2310        2320        2330              23

P   L   R   L   R   A   Q   G   C   S   I   G   V   A   V   N   R   G   V   S
CCT TTG AGG CTT AGA GCC CAA GGT TGC AGT ATC GGA GTG GCA GTC AAT CGT GGT GTT AGT
40       2350        2360        2370        2380        2390              24

G   I   I   G   M   T   F   I   S   M   Y   K   A   L   T   I   G   G   A   F
GGC ATT ATC GGA ATG ACA TTT ATA TCA ATG TAC AAG GCC TTG ACT ATT GGT GGT GCA TTC
00       2410        2420        2430        2440        2450              24

F   V   F   A   V   V   A   A   I   G   W   V   F   M   F   T   M   F   P   E
TTT GTA TTC GCT GTG GTT GCA GCA ATT GGA TGG GTA TTC ATG TTC ACA ATG TTT CCT GAA
60       2470        2480        2490        2500        2510              25

T   Q   G   R   N   L   E   E   I   E   V   L   F   G   S   Y   F   G   W   R
ACT CAA GGA AGA AAT CTT GAA GAA ATT GAG GTA TTG TTT GGC AGT TAC TTT GGC TGG AGG
20       2530        2540        2550        2560        2570              25

K   T   L   K   D   L   K   K   K   E   A   A   E   A   K   N   V   C   I   V
AAA ACA TTG AAG GAT TTG AAG AAG AAA GAA GCG GCA GAA GCA AAG AAT GTC TGC ATT GTT
80       2590        2600        2610        2620        2630              26

A   stop
GCT TAA AATTCAAATACAGCGGGGATTATAGCTTTGTGATGTTAAATGTGTTTGAGCGAGGGTGCAAAACCAAACATA
40       2650        2660        2670        2680        2690        2700        2710

CCCGGTATATTCACTCCTAAGTAGAATTTCTGGAGTACCTGCGGATTTGTTTGTGTTAACTAAGGGCGATTTTATCAAAA
2720        2730        2740        2750        2760        2770        2780        2790
```

Figure 8C

```
TCCTTGGTACCCTTGGAACTCCTCTAATAAATTTAAAACAGTATTGTGGTTTTTACTTGATTCGTGACATTCCTACATTT
2800      2810      2820      2830      2840      2850      2860      2870

CTGCTTCTCATCTCTAGTTTTATGTACGCATATAATTGTGCTTAGTACTCCTACGTTATTGCTCAACCTCTGTTTGTGAA
2880      2890      2900      2910      2920      2930      2940      2950

TCGAATATGGTTTGCTGACATCTTCCGAGACCAGAAACGGAAAGAGTAAATGTTTTTTCGCATGTGCAATTATAACATCA
2960      2970      2980      2990      3000      3010      3020      3030

ATGTCTTGCGTTTAATTGGTATGATATATGTTCTCTTGTTTGCAGCTTCTTTGCTCAGTTCATATGCACAAT
3040      3050      3060      3070      3080      3090      3100
```

Figure 8D

```
AACGTTGCCAAATAACTTTATGAGATTGTTTGATGGGTAGACATTGAAGATAAAATAAAGTTGTTTCTTCTTTTGCCGGG
        -1560      -1550      -1540      -1530      -1520      -1510      -1500      -

AGATATTCTCAAATCTCAAATATTCTGGACCGAAGAAGTTTATTTGCAATTGCCTAGTTCACAAAATAAAATAAACAGAG
1490       -1480      -1470      -1460      -1450      -1440      -1430      -1420      -

TTCACTTTTGTAGAGCAATTATTCGAAATCCACCACCATTGACGGATGCAGCTCATCTTGGACCCACTATCAACAATGAT
1410       -1400      -1390      -1380      -1370      -1360      -1350      -1340      -

CAAGAATGAACAATACATATACATGGTGTATAGTTAAGATTTCAGGATATTTTATTGGTATGATTGTTGCATTGGTATAG
1330       -1320      -1310      -1300      -1290      -1280      -1270      -1260      -

ATATAGCATGTTGAGAGGAAAGTGTTTGAAACAGAGATTGCAATATAAGTAGGGTAGGCTATAGCAGACTACTCTTAAAC
1250       -1240      -1230      -1220      -1210      -1200      -1190      -1180      -

CGAGCACCAAAAGCTTCTTGATTCATCTCTAGATAATATCAGAATGATGATTGCAGTTCAAACTATGTGCTGATACTCGT
1170       -1160      -1150      -1140      -1130      -1120      -1110      -1100      -

AAAACTCCTCTTCAGCAGTGGCTGGTTCGATTTGTTATTGGTAAATGAATTTCTATACTCGATCGCCCGGCAGAATCGGC
1090       -1080      -1070      -1060      -1050      -1040      -1030      -1020      -

CATCTAACATTATATCAAAATTTTATACTTTTTATCAGCATCCTAATGAGGGTGTTAATAATCTTTAATATTAATTGTTT
1010       -1000      -990       -980       -970       -960       -950       -940

GATAGAGATGATCGTCTAATAAACGTAAATATCGTTTAAGATGATAGTTCACCATCTTCTTTAGAAAGGTAAACTGATTC
-930       -920       -910       -900       -890       -880       -870       -860

AGATAAGCATGCTTCACTTATTGGAGATGGTGACAACGGCATTCTGCTTTTGATTGATCGACGCCCTCGGTTCCTTATGC
-850       -840       -830       -820       -810       -800       -790       -780

AAAGCAACTTTCTCTTTTGTTAGTGGACGTCTATTAGTTTCAATCCATTGTCATTTTCTGCTGTAGGAATCCTTTTTATT
-770       -760       -750       -740       -730       -720       -710       -700

ATTGGACCGAAAAATTGCTCTTCAGGCTCTACCTGAGACATATCAGATCGTAAACCAGATCAAACATATCCAATGTAATC
-690       -680       -670       -660       -650       -640       -630       -620

GGCTTGTAGATCAGGATTTTATGTGGGGTGAGATGTACGCATATTATATAGCCAGGATTTTAGGTGGCATAAGATGTACG
-610       -600       -590       -580       -570       -560       -550       -540

CATATCATATAACACTTCTACACTTATTGAGTAGAGGCAAAACAATTTTCTTTTAGTGTATAGAAAACTACAGAGTCGTG
-530       -520       -510       -500       -490       -480       -470       -460

CATAATGTTGAAATCGCATGTTTGTTGGTACAGATTGAAGGTCCATGAGCTTAAGTTAAATAAAAAATCTACGATAAAAA
-450       -440       -430       -420       -410       -400       -390       -380

TCACCATATGATATTCAACTTTTTACACGAGTCAGAATTCATAAAATGTTATTACCTGCTCAAAATTGCTAAGTTATGGA
-370       -360       -350       -340       -330       -320       -310       -300

ATATTATTGCATGGATATTATACTACTACCGCAAAAACTATCTTTAAGATAACAATATGAAGTACAAATAATGGAGTTCT
-290       -280       -270       -260       -250       -240       -230       -220

TCAGGCCACAGACAAAGCTGTACCAGAGGATATATAACTTTTCGTTTGACTGGTCCAGGTGGACGGTCGATAGTTAGCCT
-210       -200       -190       -180       -170       -160       -150       -140

CCTTTCTCCTTTTTGCACTATAAATAAAGCTCATGACTTCACAAAACAAAGTCACCAGATAAGTGAGAGTGATTAATACA
-130       -120       -110       -100       -90        -80        -70        -60
```

Figure 9A

```
                                                              M   S   C   C   G   G
GAGTCCACAACGATCTTATAATCTTAATCATTCTCTTTACTATCCATTCGAAA ATG TCT TGC TGT GGA GGA
    -50         -40         -30         -20         -10                  10

N   C   G   C   G   A   G   C   K   C   G   N   G   C   G   G   C   G   M   Y
AAC TGT GGT TGT GGT GCT GGC TGC AAG TGC GGC AAT GGC TGT GGA GGA TGC GGA ATG TAC
 20          30          40          50          60          70

P   D   V   E   K   N   T   T   A   T   I   I   D   G   V   A   P   T   K   T
CCT GAT GTG GAG AAG AAC ACA ACT GCA ACC ATC ATT GAT GGA GTT GCA CCA ACA AAG ACG
 80          90         100         110         120         130           1

F   S   Q   G   S   E   M   S   F   T   T   E   G   G   H   A   C   K   C   G
TTT TCT CAG GGT TCA GAG ATG AGC TTT ACA ACT GAA GGA GGG CAT GCC TGC AAG TGC GGA
40          150         160         170         180         190           2

S   N   C   T   C   N   P   C   K   C  stop
TCA AAC TGC ACA TGT AAT CCG TGC AAA TGT TAACGATGAAATGGAACTGAGTACCTAACAAAGCAGCTAG
00          210         220         230         240         250         260       2

CGTTTCTCCAATATTGTACTATAATAATGCCGCAGCCTGTGTTTTATGCTATTCCAGACTTGGATGTGTTTAATGTTGNT
 70         280         290         300         310         320         330         340         3

AGGCTGCTTAATCTTTTTTTTTTATGTTTTTCGTAACTACCGTTGCTCTCTGCTTTGNGGGTACTGGTATTGNCTTAAGG
 50         360         370         380         390         400         410         420         4

GTTAATTCATCTGCGNGATGAAACTAATGGCATGAAATTCT
 30         440         450         460
```

Figure 9B

```
AAAGCAACGATTTCTTTTTACCAAATTTTGTTCTTTATTCTGCAGCTAGAGCCTACAAGAAAGTGTTCCAAAATATCAAA
    -680       -670       -660       -650       -640       -630       -620       -61
AGTGACTAATCGATTAGTTATAACTTAACATGTTTTAACTGGTGTTTTAACCGATGAATGCATATATTAATGAATGCAAG
0   -600       -590       -580       -570       -560       -550       -540       -53
ATCATCTATTTACGAATAAAAAATCAATAATTAATTGACATTTATCGTTTTAGAAAGAAAGTGTTCGAAAATATCAAAAG
0   -520       -510       -500       -490       -480       -470       -460       -45
ATCCAAATCGACGAATTGTAACTTAATATGTTTTAACTAGCGAATACATATTAATGAATGCAAGATCATCTATTTACGAA
0   -440       -430       -420       -410       -400       -390       -380       -37
TAAAAAATCAATAATTAATTAACACATTTTTATTTGAAAACCGTTTTAGAAACAAATTTGGGAGTTTCCGATTCTCTTTT
0   -360       -350       -340       -330       -320       -310       -300       -29
AAGATTAATATATTTGAAAAGTTAAAAACACAATTAAATTCAGAAAATGGGAAAGTATCAAGTTGATGAATATGAGATAC
0   -280       -270       -260       -250       -240       -230       -220       -21
TTAAAAAGGATGGACGAGAGAAGGATAGCATAGGCCCCAAGCTCCATTATCAAGATTCCTCAAGTAACCTTTATTCATTG
0   -200       -190       -180       -170       -160       -150       -140       -13
AAGCGTGTGCTCTTCTCGTGCCACTCCATCTATAAATACCAGCCCAAATCACACTTCTGGAAAATATAGCAAACTACAAA
0   -120       -110       -100       -90        -80        -70        -60        -5
                                                         M   S   N   T   C   G   N
GCTCTACAATACACTCTTGCATACCACCTTACTTCAAGCTCTTAACAACC ATG TCG AAC ACC TGT GGC AAC
0   -40        -30        -20        -10                        10              20

C   D   C   S   D   K   S   Q   C   V   K   K   G   A   S   Y   G   L   D   I
TGT GAC TGC TCC GAC AAG AGC CAG TGC GTG AAG AAG GGA GCC AGC TAT GGC CTT GAC ATT
        30              40              50              60              70              80

V   E   T   G   K   S   Y   V   Q   T   X   V   M   E   V   S   A   T   E   N
GTT GAA ACT GGA AAG AGC TAT GTC CAG ACC NCT GTG ATG GAA GTC TCG GCA ACT GAG AAC
        90              100             110             120             130             140

D   G   K   C   K   C   G   T   S   C   T   C   V   N   C   S   C   G   G   H
GAC GGC AAG TGC AAA TGC GGA ACA AGC TGC ACT TGT GTG AAC TGC AGT TGC GGT GGT CAC
        150             160             170             180             190             200 stop
TAAGCAGCCCTTCTCCATCCTCCAGACAACTATAATATGTTACAAATAGAACTTGTGCATGCATGAGCTCTGTACAATAA
        210         220         230         240         250         260         270         280

AACTGTGACTATAGTGTCAAGTGTCTGAGTGTCAATTAGTCCCCTTGTATTTCAGTTTCCTTGTTACCTGTGTAATGTGT
        290         300         310         320         330         340         350         360

TCACAGCTGCTACATTAGTACAGTTGTGTTAAATGAATCACTTCCTAGTTT
        370         380         390         400         410
```

Figure 10

* Boîtes HSE (S000 030) réponse à la chaleur

● Boîtes MYB, MYC (S000 174, 175, 176, 177, 407, 408, 409, 413)

✳ Boîtes LTRE (S000 153, 250) réponse au froid

▲ Boîtes de réponse aux stress bio/abiotiques (S000 042, 430, 443, 444)

▲ Boîtes WRKY (S000 142, 310, 390)

```
AAAATGTTTC ATATTCACAA AAGAAATTTT GAACAGAAAC AATTGTGGAT GCACCTCTCT   60
ATATATTTGT ACTTTTGCAT ACTGTCGTAT ATATAGTAAA GAATTACTTA ATAGGGGTGA  120
ATGTACTCAC CGGGCAAAGT ATTAGTAATT TCTTCATTAA AATATTTAAG AGTCAATTTA  180
ATTTGCCACT GCCTTTTCTT TTTCAGTTCT TACTTCAAGG TTAGTCAATC TATTCCGGTG  240
AATAATTACG AACGAATATA TAATCTCTGA GTAGCAAAGA TTCCCAAAAC TATCCAAAAT  300
TATCCGGCGG CTGCGGATTT GATACGATAA AAAAATATCG CTATAATCAC AAATTTATTC  360
AAATTTACTA AAAAGGGCCC ACAGCCTAAT TACCAAAATC AAATTGAACT TTCCCAATTC  420
CACGCAATCC TCAAAGATAA ACACAGCAAC CACCAACTAA TACTCTATAA AAAATCATAC  480
AAAAGTCCAA CTAATTACAC CCCTCACGTT ACGATAGTCA AATTGTTTAG TCCTTTCCCC  540
CAAGCTTCGA CCATTGTTTC TCAACATTTT GTAATCTCTC TCTCTCTCGA TG          592
```

AgMT2  Longeur: 1576 paires de bases (1319 pb)

```
AACGTTGCCA AATAACTTTA TGAGATTGTT TGATGGGTAG ACATTGAAGA TAAAATAAAG   60
TTGTTTCTTC TTTTGCCGGG AGATATTCTC AAATCTCAAA TATTCTGGAC CGAAGAAGTT  120
TATTTGCAAT TGCCTAGTTC ACAAAATAAA ATAAACAGAG TTCACTTTTG TAGAGCAATT  180
ATTCGAAATC CACCACCATT GACGGATGCA GCTCATCTTG GACCCACTAT CAACAATGAT  240
CAAGAATGAA CAATACATAT ACATGGTGTA TAGTTAAGAT TTCAGGATAT TTTATTGGTA  300
TGATTGTTGC ATTGGTATAG ATATAGCATG TTGAGAGGAA AGTGTTTGAA ACAGAGATTG  360
CAATATAAGT AGGGTAGGCT ATAGCAGACT ACTCTTAAAC CGAGCACCAA AAGCTTCTTG  420
ATTCATCTCT AGATAATATC AGAATGATGA TTGCAGTTCA AACTATGTGC TGATACTCGT  480
AAAACTCCTC TTCAGCAGTG GCTGGTTCGA TTTGTTATTG GTAAATGAAT TTCTATACTC  540
GATCGCCCGG CAGAATCGGC CATCTAACAT TATATCAAAA TTTTATACTT TTTATCAGCA  600
TCCTAATGAG GGTGTTAATA ATCTTTAATA TTAATTGTTT GATAGAGATG ATCGTCTAAT  660
AAACGTAAAT ATCGTTTAAG ATGATAGTTC ACCATCTTCT TTAGAAAGGT AAACTGATTC  720
AGATAAGCAT GCTTCACTTA TTGGAGATGG TGACAACGGC ATTCTGCTTT TGATTGATCG  780
ACGCCCTCGG TTCCTTATGC AAAGCAACTT TCTCTTTTGT TAGTGACGT CTATTAGTTT   840
CAATCCATTG TCATTTTCTG CTGTAGGAAT CCTTTTTATT ATTGGACCGA AAAATTGCTC  900
TTCAGGCTCT ACCTGAGACA TATCAGATCG TAAACCAGAT CAAACATATC CAATGTAATC  960
GGCTTGTAGA TCAGGATTTT ATGTGGGGTG AGATGTACGC ATATTATATA GCCAGGATTT 1020
TAGGTGGCAT AAGATGTACG CATATCATAT AACACTTCTA CACTTATTGA GTAGAGGCAA 1080
AACAATTTTC TTTTAGTGTA TAGAAAACTA CAGAGTCGTG CATAATGTTG AAATCGCATG 1140
TTTGTTGGTA CAGATTGAAG GTCCATGAGC TTAAGTTAAA TAAAAAATCT ACGATAAAAA 1200
TCACCATATG ATATTCAACT TTTTACACGA GTCAGAATTC ATAAAATGTT ATTACCTGCT 1260
CAAAATTGCT AAGTTATGGA ATATTATTGC ATGGATATTA TACTACTACC GCAAAACTA  1320
TCTTTAAGAT AACAATATGA AGTACAAATA ATGGAGTTCT TCAGGCCACA GACAAAGCTG 1380
TACCAGAGGA TATATAACTT TTCGTTTGAC TGGTCCAGGT GGACGGTCGA TAGTTAGCCT 1440
CCTTTCTCCT TTTTGCACTA TAAATAAAGC TCATGACTTC ACAAACAAA GTCACCAGAT  1500
AAGTGAGAGT GATTAATACA GAGTCCACAA CGATCTTATA ATCTTAATCA TTCTCTTTAC 1560
TATCCATTCG AAAATG                                                 1573
```

AgMT3  Longeur: 693 paires de bases (649 pb)

```
AAAGCAACGA TTTCTTTTTA CCAAATTTTG TTCTTTATTC TGCAGCTAGA GCCTACAAGA   60
AAGTGTTCCA AAATATCAAA AGTGACTAAT CGATTAGTTA TAACTTAACA TGTTTTAACT  120
GGTGTTTTAA CCGATGAATG CATATATTAA TGAATGCAAG ATCATCTATT TACGAATAAA  180
AAATCAATAA TTAATTGACA TTTATCGTTT TAGAAAGAAA GTGTTCGAAA ATATCAAAAG  240
ATCCAAATCG ACGAATTGTA ACTTAATATG TTTTAACTAG CGAATACATA TTAATGAATG  300
CAAGATCATC TATTTACGAA TAAAAAATCA ATAATTAATT AACACATTTT TATTTGAAAA  360
CCGTTTTAGA AACAAATTTG GGAGTTTCCG ATTCTCTTTT AAGATTAATA TATTTGAAAA  420
GTTAAAAACA CAATTAAATT CAGAAAATGG GAAAGTATCA AGTTGATGAA TATGAGATAC  480
TTAAAAAGGA TGGACGAGAG AAGGATAGCA TAGGCCCCAA GCTCCATTAT CAAGATTCCT  540
CAAGTAACCT TTATTCATTG AAGCGTGTGC TCTTCTCGTG CCACTCCATC TATAAATACC  600
AGCCCAAATC ACACTTCTGG AAAATATAGC AAACTACAAA GCTCTACAAT ACACTCTTGC  660
ATACCACCTT ACTTCAAGCT CTTAACAACC ATG                              690
```

Figure 12

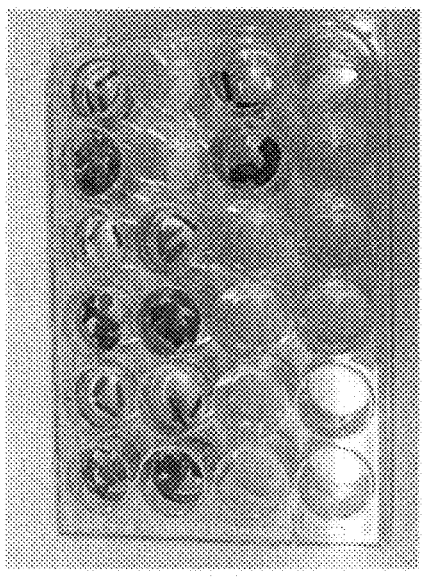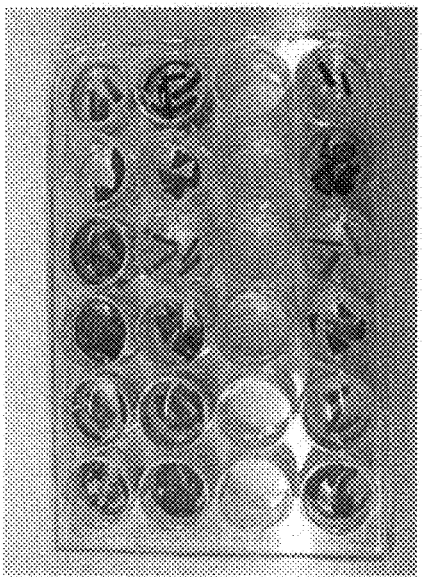
Figure 15

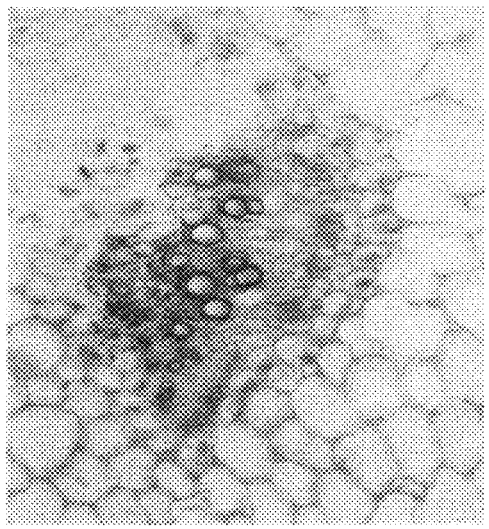
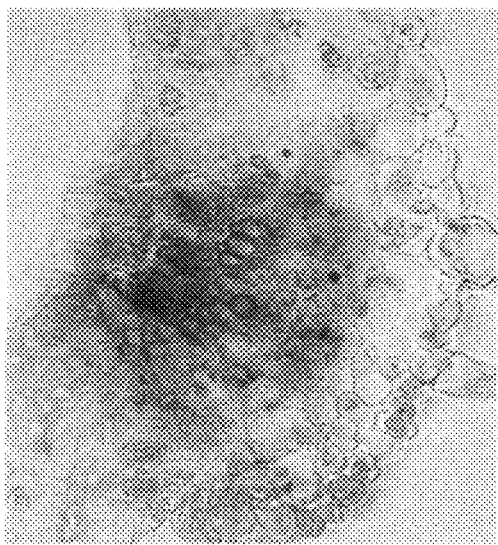
Figure 17

GENE PROMOTORS WHICH CAN BE USED IN PLANTS

This application is a §371 national stage of PCT International Application No. PCT/FR2007/000014, filed Jan. 5, 2007, and claims priority of French Patent Application No. 0600137, filed Jan. 6, 2006, the contents of all of which are hereby incorporated by reference into this application.

In the agricultural field, it may be of interest to be able to augment or reduce the expression of genes of interest in certain tissues of a plant and/or in response to environmental factors such as biotic or abiotic stresses which influence the productivity of agricultural cultures.

The present invention relates to novel sequences which regulate transcription identified in celery, the activity of which is tissue-specific, organ-specific and/or can be induced by environmental factors such as biotic or abiotic stresses, and to their use in transforming plants and placing a gene of interest under their control.

Salinity, for example, is one of the most severe environmental factors limiting the productivity of agricultural cultures. Although the salinity of the ground largely pre-dates agriculture, the problem has been aggravated by agricultural practices such as irrigation. Currently, about 20% of cultivated land in the world and almost half of irrigated land is affected by salinity.

In addition to the enormous financial cost, salinity has other serious impacts on infrastructure, water reserves and on the social structure and stability of human communities.

Two types of responses have been made to salinity: (i) introduction of environmental management to control the increase of salt in the ground, by managing irrigation and drainage, and (ii) using genetic engineering of plants to increase their salt tolerance.

The present invention in particular concerns the second approach consisting of investigating and understanding the mechanisms which allow certain plants to tolerate salt and stress in general rather better, to develop strategies rendering cultivated plants more tolerant to salt or other stresses.

Throughout their lifetime, plants which are fixed to their substrate are subjected to many variations in environmental conditions which they have to survive by adapting their growth and development. Abiotic stresses correspond to large modifications in chemical or physical environmental factors, while biotic stresses are induced by an interaction between the plant and a living organism. The abiotic factors, which particularly affect culture yields, include hydric stress (dryness or surplus water), extreme temperature modifications, mineral element deficiencies in the ground and the high concentration of salts or heavy metals in the ground.

Saline stress caused by too high a concentration of NaCl in the environment of the plant falls into the category of abiotic stresses. Although $Na^+$ is necessary for some plants, particular for halophytes, a high concentration of NaCl is a limiting or even toxic factor in plant growth. This phenomenon is widespread over arable surfaces throughout the world.

In response to environmental stresses, plants have developed an array of physiological and biochemical strategies to adapt or at least tolerate stress conditions. Such strategies are linked to modifications in gene expression, as shown by changes in the quantities of mRNA and newly synthesized proteins. The identified genes code for proteins associated with many functions such as ion compartmentalization, equilibrium of the redox potential, degradation or protection of proteins, the synthesis of osmolytes. A number of studies have been carried out on molecules termed "osmolytes" as their synthesis is augmented in many abiotic stresses (Hasegawa et al, 100a and b). Such molecules may accumulate in large quantities during the salt response (or osmotic stress), thus allowing the water balance in the cell to be restored.

It has been proposed that metabolic engineering could play a major role in increasing the tolerance of plants to stress. It has been shown that plants transformed to express enzymes leading to the synthesis of certain osmolytes were more resistant to saline stress than non transformed plants (Tarczinsky et al, 1993, Shen et al, 1997a and b), thus confirming the importance of osmolytes. However, certain of these results are controversial in that the quantity of osmolytes in the transgenic plants was too low to explain an osmotic effect (Karakas et al, 1997). Thus, this effect was attributed to an anti-oxidant role rather than to a purely osmolytic role.

The synthesis of such osmolytes takes place in source tissues or is based on molecules deriving from photoassimilates. As a result, the transport over long distance of photoassimilates in phloem is certainly affected during saline stress, although little data is available in this regard (Noiraud et al, 2000).

Sap produced from phloem also transports a wide range of ions, metabolites and macro-molecules such as proteins and nucleic acids, many of which are involved in signaling. Thus, phloem can be considered to be the major actor in communication between tissues in vascular plants ((Ruiz-Medrano et al, 2001).

However, to this day, knowledge regarding the genes specifically expressed in the phloem or in the roots is scanty, especially in vegetables or in truck (market) garden species such as celery, despite recent studies on various plant models (Vilaine et al, 2003). Knowledge regarding the promoters of such genes, especially regarding their phloem-specific, root-specific and stress inducible properties, is also scanty to non-existent.

In the absence of such knowledge, it is thus not possible to place any coding sequence under the control of a promoter which could express that coding sequence only under stress conditions, preferably in the phloem or roots.

The present inventors have now determined the sequence of three promoters with preferential activity in vascular tissues and more particularly the phloem or roots, this activity being, if appropriate, a function of the stress conditions in the cell. The inventors have also produced constructs using these promoters which can express the sequences of interest only under stress conditions, preferentially in the phloem or preferentially in roots.

As a consequence, in a first aspect of the invention, the present application concerns a sequence of nucleic acids having a transcriptional promoter activity such that said sequence comprises SEQ ID NO: 1, 2 or 3 or a fragment or fragments (or portions) of at least one of those sequences. A fragment or a portion of SEQ ID NO: 1, 2 or 3 is defined as a sequence comprising at least 30 consecutive nucleotides of SEQ ID NO: 1, 2 or 3.

A portion of SEQ ID NO: 1, 2 or 3 may contain only 30 nucleotides but it may advantageously contain at least 50 consecutive nucleotides of SEQ ID NO: 1, 2 or 3, for example exactly 50 or more than 50 or even more than 75, 80 or 90. A portion may also contain more than 100 consecutive nucleotides of SEQ ID NO: 1, 2 or 3, in particular 120, 150 or even 180 or 200. In accordance with the present invention, the portions of SEQ ID NO: 1, 2 or 3 which are preferred are fragments corresponding to almost the whole of SEQ ID NO: 1, 2 or 3 with just one deletion of 1 to 10, 20, 30 or 50 nucleotides at the 3' and/or 5' end or even within the SEQ ID NO: 1, 2 or 3 sequences.

It is also envisaged that a sequence of the invention could comprise at least two fragments of SEQ ID NO: 1, 2 or 3, at least one of said fragments having a minimum length of 30 nucleotides. The various fragments may be fragments derived from distinct sequences, for example a fragment of SEQ ID NO: 1 and a fragment of SEQ ID NO: 2 or fragments of the same sequence. In the latter case, the fragments are preferably non consecutive, for example separated by 2, 10, 20 or 50 nucleotides.

In accordance with a preferred implementation of the invention, a sequence of the invention comprises or consists of all of one of the sequences SEQ ID NO: 1, 2 or 3.

The term "sequence having a transcriptional promoter activity" means a sequence having a promoter activity, i.e. of a nature to promote transcription of a sequence placed downstream of said promoter sequence, possibly in the presence of suitable co-factors.

Such a transcriptional promoter activity may be tested by cloning a sequence which may have such an activity upstream of any sequence to be transcribed, in the presence of RNA polymerase and ribonucleotides. If RNA molecules are obtained, while no RNA molecule is obtained in the absence of cloning of the test sequence, it may be deduced therefrom that said test sequence has a transcriptional promoter activity. A suitable test is described in the experimental section.

The transcription initiation site may be either within the sequence of the invention or at the 3' end of a sequence of the invention or on the downstream 3' side of a sequence of the invention. In the first case, a portion of the sequence of the invention is transcribed.

In addition to all or part of one of sequences SEQ ID NO: 1, 2 or 3, a sequence of the invention may also contain additional sequences provided that they do not displace the transcriptional promoter property. Such additional sequences may in particular be "enhancers" or other sequences such as binding sites for various proteins.

Said transcriptional promoter activity may be manifested in any type of cell, in vivo and/or also in vitro in solution, in the presence of RNA polymerase and all of the elements necessary for transcription, in particular in the presence of ribonucleotides.

Advantageously, a sequence of the present invention has a ubiquitous promoter activity, i.e. both in prokaryotic and in eukaryotic cells, in plant or animal cells, or in the presence of a RNA polymerase of one of those cells. A sequence of the present invention is preferably active as a promoter in plant cells or in the presence of a RNA polymerase derived from a plant cell.

A preferred property of a sequence of the invention is its capacity to promote transcription in a plant cell in response to a stimulus. Said stimulus is preferably a stimulus connected with a stress. Preferably, the transcriptional promoter activity possessed by a sequence of the invention is sensitive to a biotic or abiotic stress; this activity is induced or enhanced under biotic or abiotic stress conditions.

The term "biotic stress" means the stress in a plant which is induced by an interaction between the plant and a living organism, for example during attack by greenfly.

Abiotic stresses, on the other hand, correspond to major modifications in chemical or physical factors of the environment. Abiotic factors which have a particular effect on culture yields are hydric stress (dryness or surplus water), extreme temperature modifications, mineral element deficiencies in the ground and a high concentration of salts or heavy metals in the ground.

The stress may be sensed on a cellular level, in an organ of the plant or in the organism as a whole.

The transcriptional activity of a sequence of the invention may also be induced when certain components or conditions linked to stress are reproduced. As an example, the transcriptional activity of a sequence of the invention may be induced as a result of the presence of certain factors which are linked to stress such as stress proteins.

In one preferred implementation, a sequence of the invention has a preferential transcriptional promoter activity in vascular tissues. The vascular tissues of particular interest are the phloem and/or the xylem, but preferably the phloem.

In accordance with another preferred implementation, a sequence of the invention has a specific transcriptional promoter activity in one or more organs, i.e. a promoter the activity of which is higher in certain organs of the plant, for example the stems, leaves or roots, or even limited to these organs. In a preferred implementation, a sequence of the invention has a specific transcriptional promoter activity in the roots.

The transcriptional promoter activity presented by a sequence of the invention is preferably manifested in plant cells and more particularly in the cells of truck garden plants or vegetable plants, i.e. plants used for the individual or intensive production of vegetables, herbs and certain fruits (such as melon or watermelon), in particular apiaceae, asteraceae, brassicaceae (or crucifereae), chenopodiaceae, cucurbitaceae, poaceae, rosaceae, solanaceae, valerianaceae or legumineae. More particularly, the transcriptional promoter activity manifests itself in the cells of celery (*apium gravolens* L), *Arabidopsis thaliana* or tomato (*solanum lycopersicum* L).

The sequences of the invention comprise SEQ ID NO: 1, 2 or 3 or one or more fragments (or portions) of at least one of these sequences. Preferably, the sequences of the invention consist of one of the following sequences: SEQ ID NO: 1, 2, 3, 4, 5 or 6, or they comprise one of these sequences. SEQ ID NO: 4 is a sequence comprising SEQ ID NO: 1, SEQ ID NO: 5 and a sequence comprising SEQ ID NO: 2 and SEQ ID NO: 6 is a sequence comprising SEQ ID NO: 3.

In accordance with a second aspect of the present invention, a sequence of the invention may also be a sequence which has at least 5 point mutations compared with a sequence as defined above in accordance with the first aspect, i.e. with respect to a sequence comprising SEQ ID NO: 1, 2 or 3 or one or more fragments (or portions) of at least one of sequences SEQ ID NO: 1, 2 or 3 where said fragment comprises at least 30 consecutive nucleotides of SEQ ID NO: 1, 2 or 3.

A sequence in accordance with this second aspect of the invention may, for example, have a single mutation with respect to a sequence according to the first aspect, but preferably at least two point mutations or even 3, 4 or 5 point mutations.

The term "point mutation" means a single modification of a single nucleic acid, said modification possibly being suppression of a nucleic acid compared with the sequence with no mutation or addition of a nucleic acid compared with the sequence without mutation or a modification to a nucleic acid compared with the sequence without mutation. The term "modification of a nucleic acid" means both substitution of a nucleic acid by another natural nucleic acid (for example substitution of A for G) and the chemical modification of a natural nucleic acid (for example replacing an adenine by 2-methyladenosine or 4-acetylcytidine).

The various modified nucleic acids which can be incorporated into a sequence of the invention are well known to the skilled person.

In a particular implementation, a mutation may be introduced to remove the transcriptional promoter activity of a sequence in accordance with the first aspect of the invention, or to modify its characteristics.

Preferably, a sequence in accordance with this second aspect of the invention will have at most 5 point mutations with respect to a sequence comprising a fragment of SEQ ID NO: 1, 2 or 3 of at least 40 consecutive nucleotides, preferably at least 50 consecutive nucleotides.

A sequence in accordance with this second aspect of the invention may also have a transcriptional promoter activity, but not necessarily. The mutations introduced compared with the sequence of the first aspect of the invention may modify the promoter activity of such a sequence, for example by modifying its initiation per second rate, or by modifying its cell specificity or the transcription initiation conditions.

In a third aspect, the present invention also concerns a nucleic acid sequence which has a transcriptional promoter activity and which has at least 70% identity with a sequence selected from SEQ ID NO: 1, SEQ ID NO: 2, SEQ ID NO: 3, SEQ ID NO: 4, SEQ ID NO: 5 and SEQ ID NO: 6. Preferably, the percentage identity is more than 70%, i.e. at least 75% or 80%, but preferably at least 85% or 90% identity or even at least 95% identity. Sequences which are also envisaged exhibit 97%, 98%, 99% or even 99.5% identity with one of sequences SEQ ID NO: 1 to 6.

The percentage identity between two sequences S1 and S2 of nucleic acids is calculated by aligning the two sequences so as to maximize the common sequences, possibly by inserting gaps then by dividing the total number of common nucleic acids by the number of nucleic acids in the longest sequence.

A high percentage identity also results in hybridization of monocatenary sequences S1 and S2 under high stringency conditions. The conditions ensuring high stringency are well known to the skilled person. In fact, stringency is defined by the experimental conditions of temperature, pH and ionic strength which allow molecular hybridization. Two parameters in particular determine stringency: temperature and salt concentration. High stringency conditions correspond, for example, to a high temperature (above Tm) and/or low ionic strength, to encourage specific pairings.

As an example, high stringency conditions may be illustrated by a medium having the properties described in the experimental section.

The term "sequence of the invention" also denotes a sequence in accordance with the first, second or third aspect of the invention.

In particular, a sequence of the invention may be a double stranded DNA, but also a single stranded DNA or partially double stranded DNA. Further, a sequence of the invention may have varied topologies. It may also be circular DNA, or even supercoiled.

The present invention also concerns a sequence complementary to one of the sequences described above.

A sequence of the invention may be used in various technical fields and in particular in agriculture, especially in the transgenic plant sector.

The invention also concerns nucleic acid probes such that said probes are capable of hybridizing under high stringency conditions with a sequence selected from SEQ ID NO: 1, 2 or 3. A probe as mentioned comprises at least 25 nucleotides, preferably at least 30. As a general rule however, the nucleic acid probes comprise less than 150, even less than 100 or even less than 50 nucleic acids.

Such probes can identify sequences homologous to one of SEQ ID NO: 1, 2 or 3 in various organisms or can detect the presence of one or these sequences, in vitro or in vivo. Such probes may be DNA or RNA probes, single or double stranded. They may, for example, be used as primers in PCR experiments or in Southern blot experiments.

The present invention also pertains to a DNA construct or DNA construction which is constituted or comprises a sequence having a promoter activity as described above and which also comprises a sequence of nucleic acids to be transcribed. The construct of the invention is produced so that the sequence of interest to be transcribed is located downstream of the promoter sequence, i.e. at the 3' end of the promoter sequence, and transcription of the sequence of interest is directed by the promoter sequence. The sequence of the invention and the sequence to be transcribed may be contiguous or may be separated by interposed nucleic acids. In this latter case, the interposed sequence preferably comprises less than 200 or even less than 50 or less than 20 nucleotides.

A construct of the invention may also comprise sequences allowing transcription termination or even sequences allowing translation termination (stop codon).

Transcription of a nucleic acid sequence is said to be directed by a promoter when said promoter allows transcription of the sequence and it controls that transcription. The sequence of interest is thus transcribed under conditions and to a degree which is a function of the promoter. Thus, it is possible, using the teaching of the invention, to place a sequence of interest under the control of a promoter sequence of the invention so that said sequence of interest is transcribed uniquely under stress conditions, for example uniquely under saline stress conditions in plant cells, or specifically in one organ of the plant, such as the roots or a tissue such as phloem and/or xylem. Because of the specific properties of the promoter sequences of the invention, it is thus possible to obtain transcription of a sequence of interest preferentially in vascular cells and preferentially under stress conditions or preferentially in the roots.

In accordance with a preferred implementation, a sequence of interest is placed under the control of SEQ ID NO: 1 or SEQ ID NO: 3 or a sequence of the invention derived from one of these two sequences and having a transcriptional promoter activity so that transcription of said sequence of interest is induced in response to a stress, especially a saline stress, and more particularly in the plant phloem.

In accordance with a further preferred implementation, a sequence of interest is placed under the control of SEQ ID NO: 2 or a sequence of the invention derived from SEQ ID NO: 2 and having a transcriptional promoter activity so that said sequence of interest is transcribed to a greater extend in the phloem of the plant.

In accordance with another preferred implementation, a sequence of interest is placed under the control of SEQ ID NO: 1 or a sequence of the invention derived from SEQ ID NO: 1 and having a transcriptional promoter activity so that said sequence of interest is transcribed to a greater extent in the roots than in the stems and leaves.

In accordance with a particular implementation of the invention, the promoter sequence and the sequence of interest to be transcribed which is within said construct are mutually heterologous. The term "heterologous" means that they derive from different sources, for example different organisms. Two sequences are also said to be heterologous when at least one of the two sequences is artificial (i.e. not present in nature). The construct comprising a sequence to be transcribed which is heterologous with respect to a promoter sequence of the invention thus comprises a chimeric gene. Preferably, the sequence to be transcribed is different from the sequence to be transcribed which is naturally associated with the promoter sequence of the invention.

In accordance with a highly preferred implementation, the sequence of interest to be transcribed is a coding sequence which is thus not also for transcription but also for translation. It may be an integrally coding sequence, for example a cDNA sequence, or a partially coding sequence, for example a sequence comprising introns and exons. The protein or peptide coded by such a sequence of interest may, for example, be a protein for resistance to a herbicide or to an antibiotic, or a growth factor, a stress resistance factor, or a toxic or lethal protein. Requirements will dictate to the skilled person what sequence of interest to place under the control of a promoter of the invention.

They are preferably sequences coding for peptides of interest in the plant field, especially peptides or proteins having an activity in plant cells, or having a nutritional or aesthetic advantage. They may also be lethal proteins which can destroy any plant which has been subjected to a stress. They may also be proteins or peptides allowing detection of cells expressing them.

The term "DNA construct" as used within the context of the present invention means any non natural DNA support. Such a construct may in particular be a vector allowing transfer of the construct into a cell. The construct is preferably a vector, for example a viral vector, but is preferably a plasmidic vector or plasmid. One plasmid which is of advantage in the context of the present invention is the Ti plasmid of agrobacteria or a plasmid derived from the Ti plasmid, which has retained its DNA transfer properties but is free of oncogenes.

A plasmid of the present invention may, in addition to the promoter sequence of the invention and a sequence of interest to be transcribed, comprise resistance genes which in particular can allow positive or negative selections to be carried out. Said resistance genes may be genes for resistance to herbicides or to antibiotics.

It may also be advantageous for the construct or plasmid of the invention to include bacterial resistance genes, for example to facilitate subsequent bacterial multiplication steps.

The invention also concerns a plant cell which has been transformed by a sequence of the invention or by a construct as defined above, in particular by a construct comprising a sequence to be transcribed which is heterologous with respect to a promoter sequence of the invention, regardless of the means employed to carry out the transformation. Currently, very diverse means are employed to allow transformation of cells by a nucleic acid sequence. Examples which may be cited are transformation by electroporation, bombardment and using agrobacteria. Clearly, depending on the type of cells to be transformed and the species in question, in particular the plant species, certain techniques are preferred over others. The skilled person will know for each cell type which techniques are the most appropriate for carrying out a transformation.

Similarly, the skilled person will know what techniques will allow transitional transformation of the cell, the genetic material being lost as a consequence, and which techniques will allow integration of the transferred sequence into the genome of the cell in a stable manner. The term "genome of a cell" means both the nuclear genome and the chloroplastic or mitochondrial genome. Preferably, it is a nuclear genome.

The cell may be any type of cell, prokaryotic or eukaryotic, although eukaryotic cells are preferred in the context of the present invention. A cell of the invention is also preferably a plant cell, but it may also be a bacterial cell, an animal cell, for example from a mammal, or any other type of cell, for example a yeast cell. Preferably, it is a cell from a plant of agronomic interest.

The present invention also concerns a transgenic plant comprising in its genome a sequence of the invention, said sequence being exogenous in nature. The terms "transgenic plant" and "exogenous sequence" mean that the sequence of the invention has been transferred deliberately to the plant and said sequence was not previously naturally present in the plant.

A transgenic plant of the invention may also comprise a construct as described above, in particular a construct comprising a sequence to be transcribed which is heterologous with respect to a promoter sequence of the invention.

A transgenic plant of the invention thus comprises in its genome a sequence (or construct) of the invention; preferably, said sequence (or construct) is inserted into the nuclear genome of any cell of the plant, but the invention also encompasses situations in which the sequence is inserted into the mitochondrial genome or into the chloroplastic genome. It is also possible to maintain the sequence or construct of the invention in an extrachromosomal manner.

The sequence (or construct comprising said sequence) is preferably stably inserted, although transient insertion may also be envisaged.

The present invention also concerns transgenic plants comprising cells transformed as described above.

Preferably, all of the cells of a transgenic plant of the invention comprise a sequence or a construct of the invention. It is also envisageable that only certain parts of said plants will comprise such transformed cells, for example when the plants are chimeric or due to excision of a transgene from certain cells.

The invention also pertains to parts of said transgenic plants. Parts of particular interest are fruits, flowers, roots, stems, leaves, and also seeds, buds, grains and reproductive material, including male and female reproductive material, as well as the cells, said portions of the invention having transformed cells comprising a sequence or a construct in accordance with the invention. Preferably, they comprise a construct comprising a sequence to be transformed which is heterologous with respect to a promoter sequence of the invention. Said parts are thus also transgenic.

A transgenic plant of the invention may be any type of plant. It may be a monocotyledon or dicotyledon plant. Preferably, a transgenic plant is of agronomic interest. In particular it may be a cereal plant, a truck plant or vegetable plant, or a fruit tree. Preferably, it is a plant other than celery.

Plants from the following families are particularly preferred: plants from the cucurbitaceae, chenopodiaceae, crucifereae, poaceae, legumineae, apiaceae, rosaceae, valerianaceae, solanaceae and asteraceae families.

Particularly preferred examples of transgenic plants of the invention are the tomato plant, the melon plant and the lettuce plant. Other preferred plants are celery, onion, beet, broccoli, wheat, asparagus, sweetcorn and rape.

A transgenic plant of the present invention may also contain in its genome other transgenes independently of the sequence of the invention; in particular, it may be a gene for resistance to viral infection under the control of a constitutive promoter. In this case, the various transformations may have been carried out simultaneously during a single transformation step or sequentially.

A transgenic plant of the invention may have been regenerated from transformed cells. It is also possible to obtain a plant of the invention by descending it from another transgenic plant of the invention.

The present invention also concerns a transgenic plant comprising in its genome a nucleic acid sequence comprising all or a portion of SEQ ID NO: 1, such that said sequence has a transcriptional promoter activity, said part comprising at least 30 consecutive nucleotides of SEQ ID NO: 1, said sequence being in functional association with a heterologous coding sequence and expressing said coding sequence in a specific manner in the roots. Preferably, said plant belongs to the apiaceae, asteraceae, brassicaceae (or crucifereae), chenopodiaceae, cucurbitaceae, poaceae, rosaceae, solanaceae, valerianaceae or legumineae families.

The present invention also concerns a transgenic plant comprising in its genome a nucleic acid sequence comprising all or part of SEQ ID NO: 1, 2 or 3 such that said sequence has a transcriptional promoter activity, said portion comprising at least 30 consecutive nucleotides of SEQ ID NO: 1, 2 or 3, and said sequence being in functional association with a heterologous coding sequence and expressing said coding sequence in a specific manner in the phloem. In a particular implementation, said sequence is SEQ ID NO: 2 or a portion of SEQ ID NO: 2 comprising at least 30 consecutive nucleotides and said plant belongs to the family of apiaceae, brassicaceae, chenopodiaceae, convolvulaceae, cucurbitaceae, fabaceae, grossulariaceae, lamiaceae, liliaceae, poaceae, polygonaceae, rosaceae, solanaceae or valerianaceae. In a further particular implementation, said sequence is SEQ ID NO: 1 or 3 or a portion of SEQ ID NO: 1 or 3 comprising at least 30 consecutive nucleotides, said plant belonging to the brassicaceae family and expression of said coding sequence is induced by a biotic or abiotic stress. In a preferred implementation, said biotic or abiotic stress is a saline stress.

The present invention also pertains to a method for obtaining a transgenic plant of the invention. Such a method comprises the following steps:
  obtaining a construct of the invention as described above;
  introducing the construct into a cell deriving from a plant of interest; and
  regenerating a transgenic plant from the transformed cells.

A method of the invention may clearly comprise numerous other steps preceding or following the steps mentioned. A method of the invention may advantageously also comprise a supplemental step for crossing the transgenic plant obtained with other plants, which may or may not be transgenic. Additional crosses may clearly be carried out. Multiplication steps, sexual or asexual, depending on the species, and obtaining descendents, may also be carried out.

Preferably, the descendants obtained at the end of the method are examined to determine the plants of the lineage which include a sequence or a construct of the invention. The plants comprising a sequence or a construct of the invention may also be isolated. Such plants which include in their genome a sequence or a construct of the invention and which are derived from the method described above also form part of the invention. Preferably, the plants from the descendents which include a sequence or a construct of the invention are determined by a selection step. Said selection may be field or greenhouse selection or genetic selection using genetic markers.

The present invention also concerns the use of a sequence or a construct of the invention to produce transgenic plants, i.e. in the genetic engineering field.

As explained above, one application of the present invention is the use of promoter sequences of the invention positioned upstream of a coding sequence of interest (transgene) so that the protein coded by the sequence of interest is only expressed under specific stress conditions, preferably in certain vascular organs of the transgenic plant. By this means, the transgene is expressed to a small or zero extent under normal conditions and its expression is induced only under stress conditions. This characteristic of the invention is of major interest since it becomes possible to only express certain transgenes, in particular resistance genes, when it proves necessary, i.e. under stress conditions. The constitutive expression of certain transgenes is sometimes useless or even deleterious under normal conditions. The present invention means that it is possible to express the transgenes only under stress conditions.

Within the context of the invention, the inventors have also discovered a novel protein, namely a novel mannitol transporter in the celery apium graveolens, denoted AgMaT3. As a result, the present application also concerns a peptide comprising a sequence which has at least 70% identity with SEQ ID NO: 8, preferably at least 80% identity or even 90% or even 95% identity with said SEQ ID NO: 8. Preferred peptides in accordance with this aspect of the invention are peptides comprising or consisting of SEQ ID NO: 11. Other preferred peptides are those which are coded by all or part of SEQ ID NO: 7, 13 or 14, or by a sequence derived from SEQ ID NO: 7, 13 or 14 due to degeneracy of the genetic code.

Preferably, such an amino acid sequence in accordance with this aspect of the invention has the capacity to transport mannitol through a lipid bilayer, especially in plant cells.

The application also concerns nucleic acid sequences coding for peptides as described above. In accordance with one possible implementation, said sequence is downstream of a promoter of the invention, for example SEQ ID NO: 1.

KEY TO FIGURES

FIG. 1: Maps of cloning vectors used.
1A: PDR 195 and 196 vectors
Multiple cloning site of PDR 195: Xhol-Notl-Sacll-BamHI
Multiple cloning site of PDR 196: Spel-BamHI*-Smal-Pstl-EcoRI-EcoRV-Hindlll-Sall-Xhol-Acc651-Kpnl-BamHI*
The bold type indicates enzymes which do not cleave elsewhere in the plasmid and* indicates those which cleave twice in the MCS.
1B: plasmid pBI 101-GUS-R1R2 (13942 bp) and plasmid pBI 101-GFP5-R1R2 (13116 bp)

Figure 2:
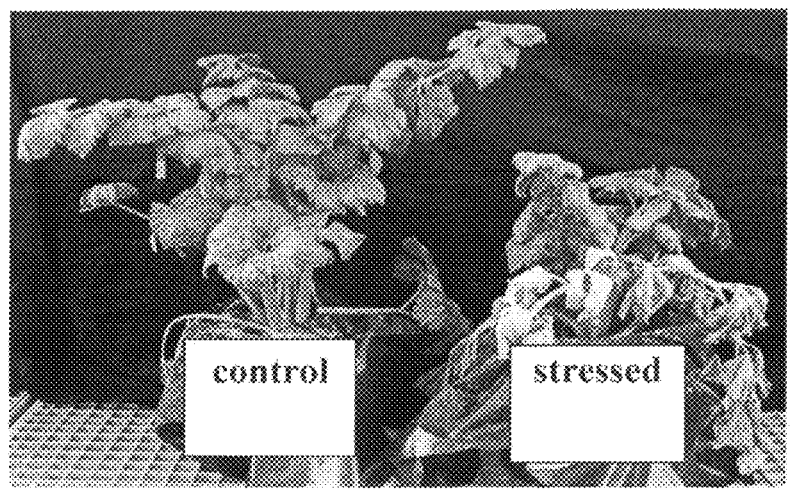

FIG. 2: Celery maintained for three weeks with water or a fertilizer solution (control plant) and with 300 mM NaCl (stressed plant).

Figure 3:
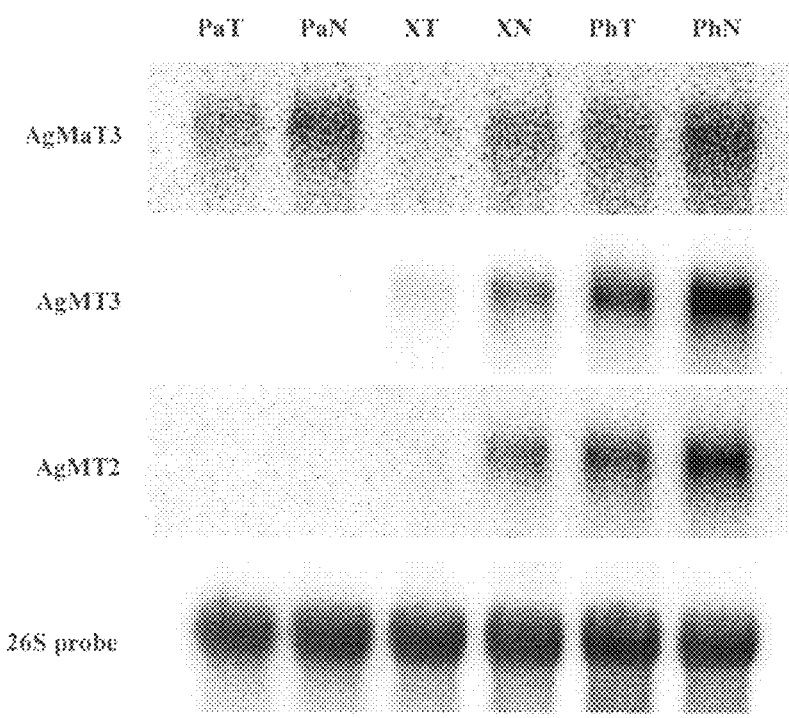

FIG. 3: Northern hybridizations of storage parenchyma, xylem and phloem from petioles of "control" plants and plants "stressed" with NaCl (300 mM, 3 weeks) using probes produced from sequences obtained via a subtractive library. Quantification was carried out using a 26S ribosomal probe. Abbreviations: PaT, control parenchyma; PaN, NaCl parenchyma; XT, control xylem; XN, NaCl xylem; PhT, control phloem; PhN, NaCl phloem.

Figure 4:
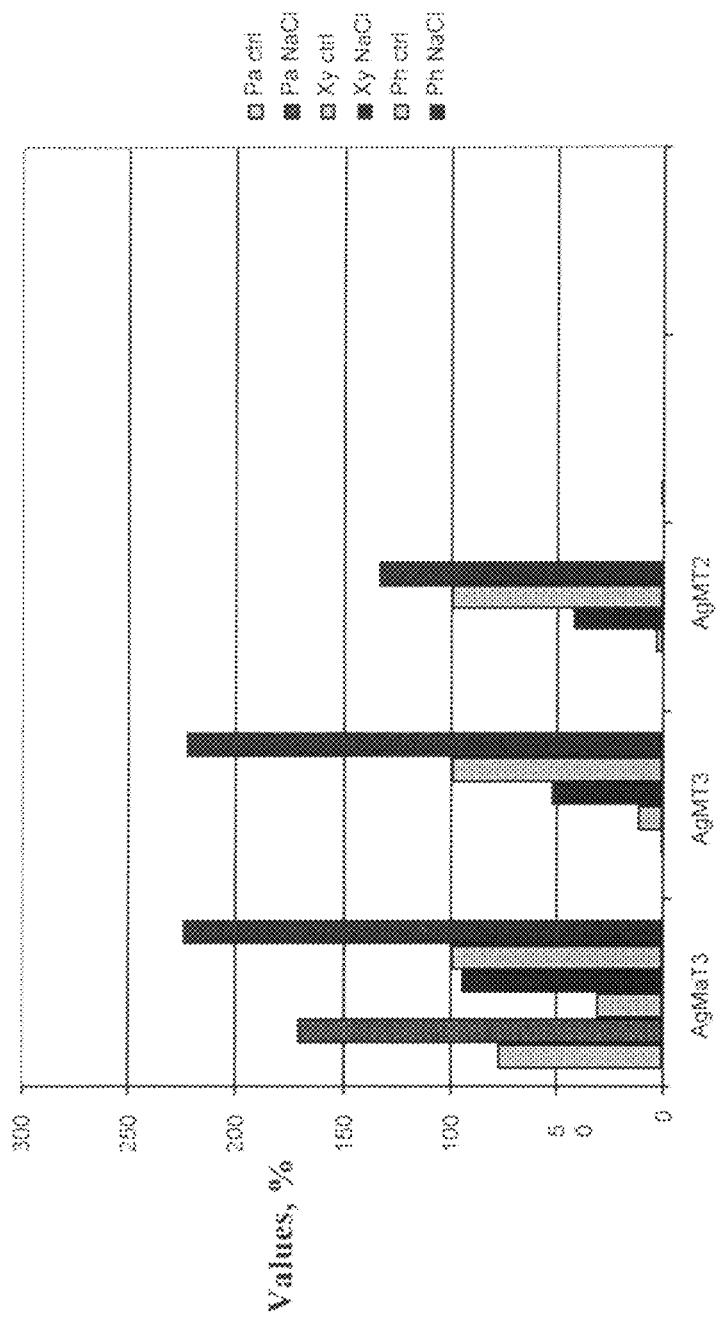

FIG. 4: Graphical representation of the level of expression of test probes during Northern hybridization as a function of the tissue. Abbreviations: AgMaT3, apium graveolens mannitol transporter 3; AgMT2 and 3, apium graveolens metallothioneins 2 and 3.

Figure 5:
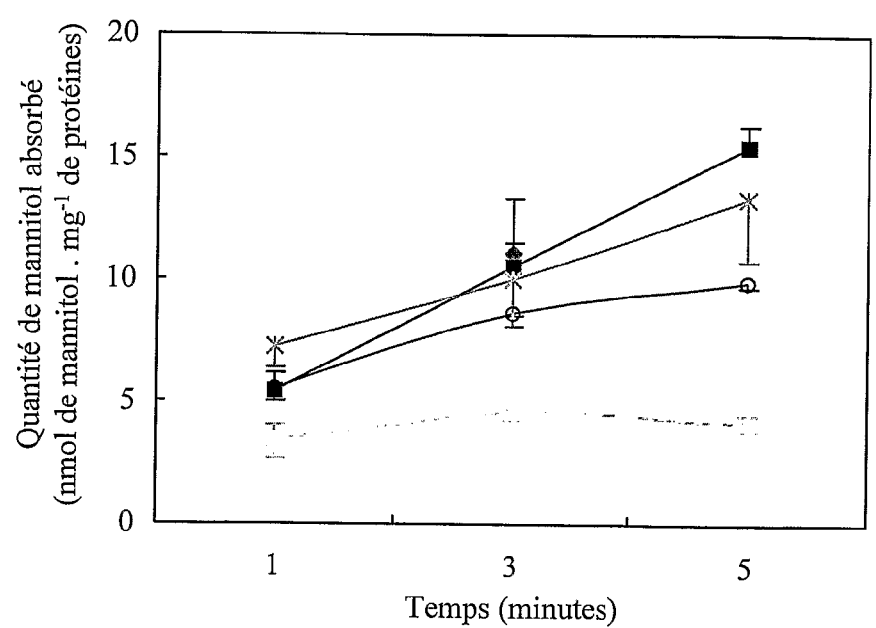

FIG. 5: Absorption of mannitol (0.55 mM) by RS453 yeasts supplemented with PDR (▲), or with AgMaT1/PDR (♦) or by three independent AgMaT3/PDR clones (■, O and x), as a function of time. The curve produced with the strain transformed by the empty plasmid acted as a control. The values correspond to the mean±the standard deviation of a single experiment with three repetitions per point.

Figure 6A:
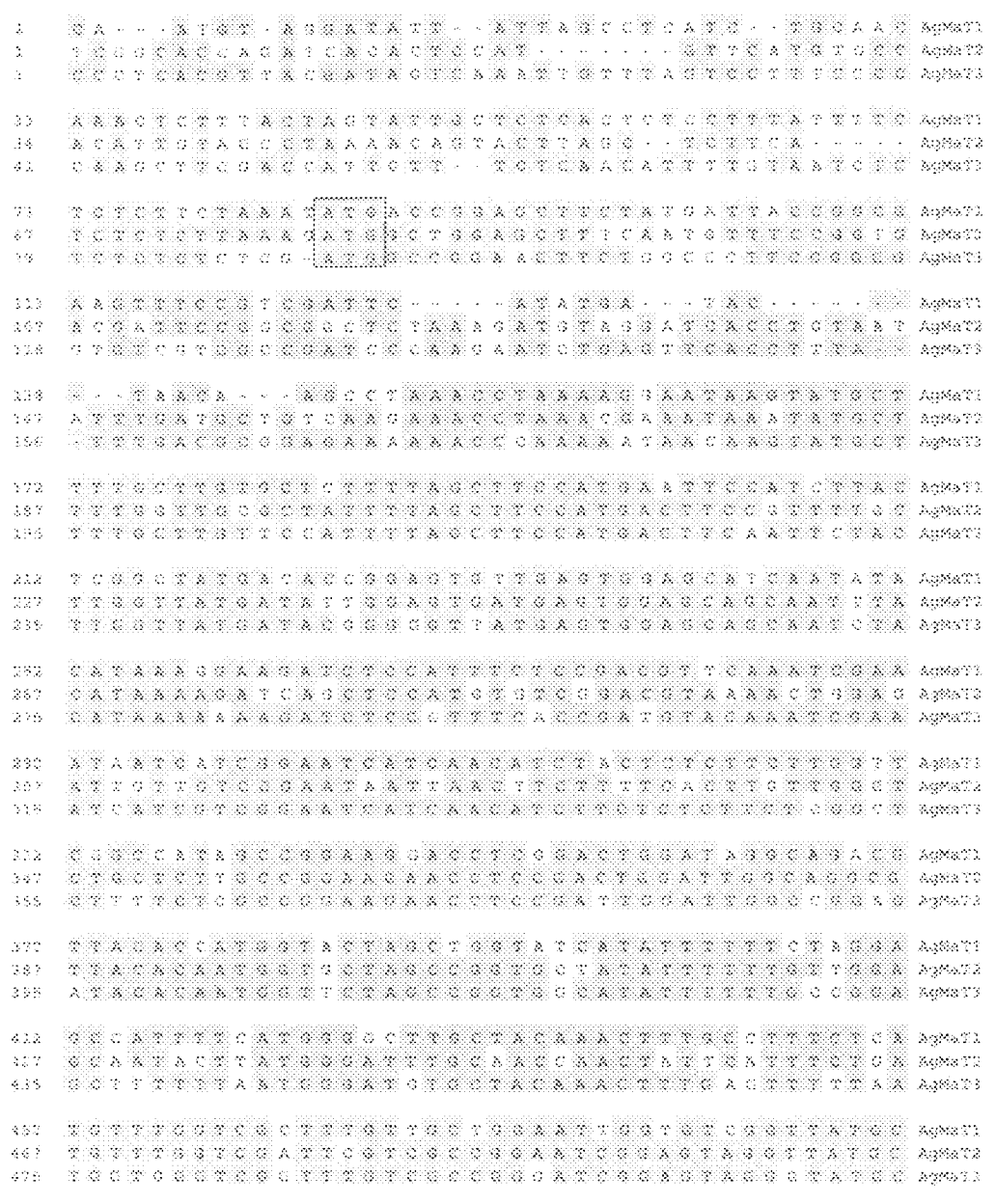
Figure 6B:
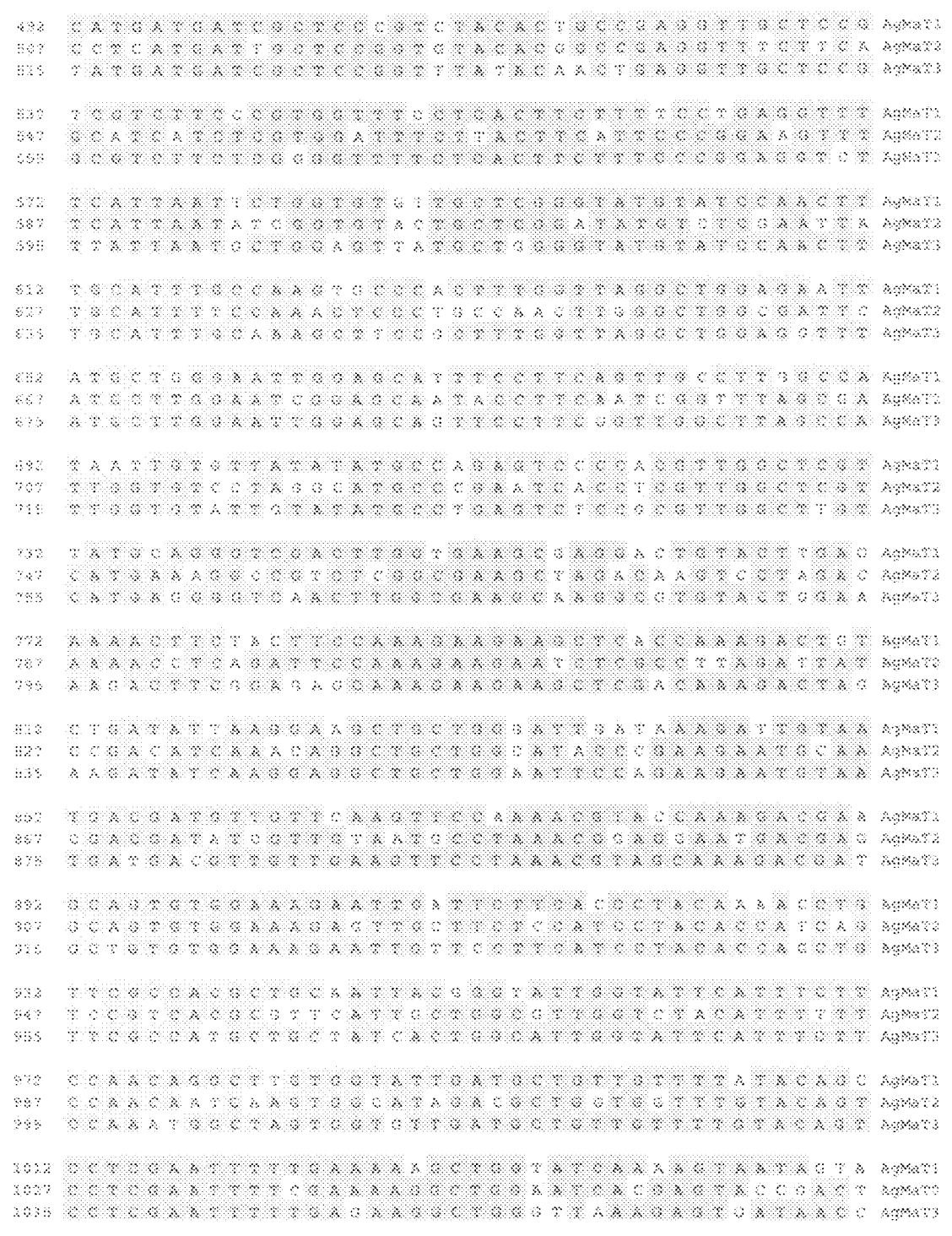
Figure 6C:
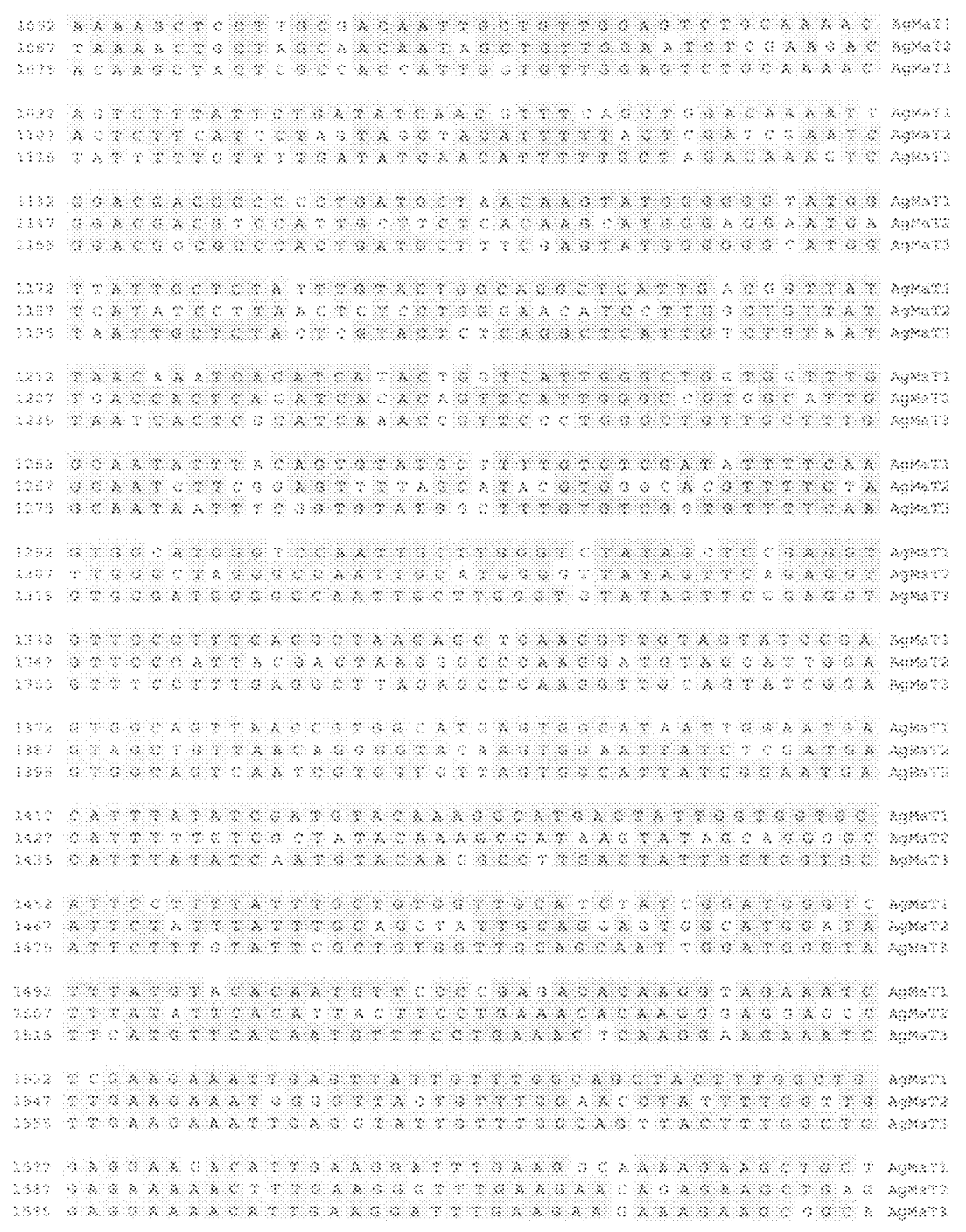
Figure 6D:
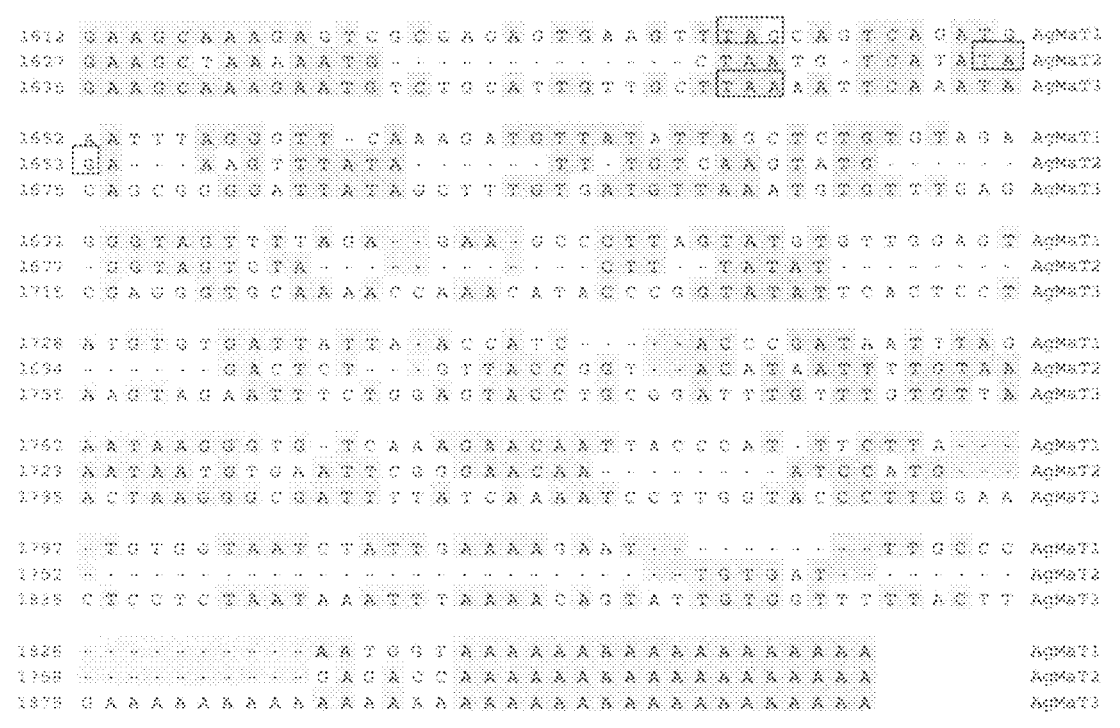

FIG. 6: Alignment of nucleotide sequences of cDNA from AgMaT1, 2 and 3. The sequences were aligned using the Clustal method of the MEGALIGN program (DNAstar, Madison, Wis.). Residues identical to the consensus sequence are underlined. The ATG and stop codons are boxed.

Figure 7:
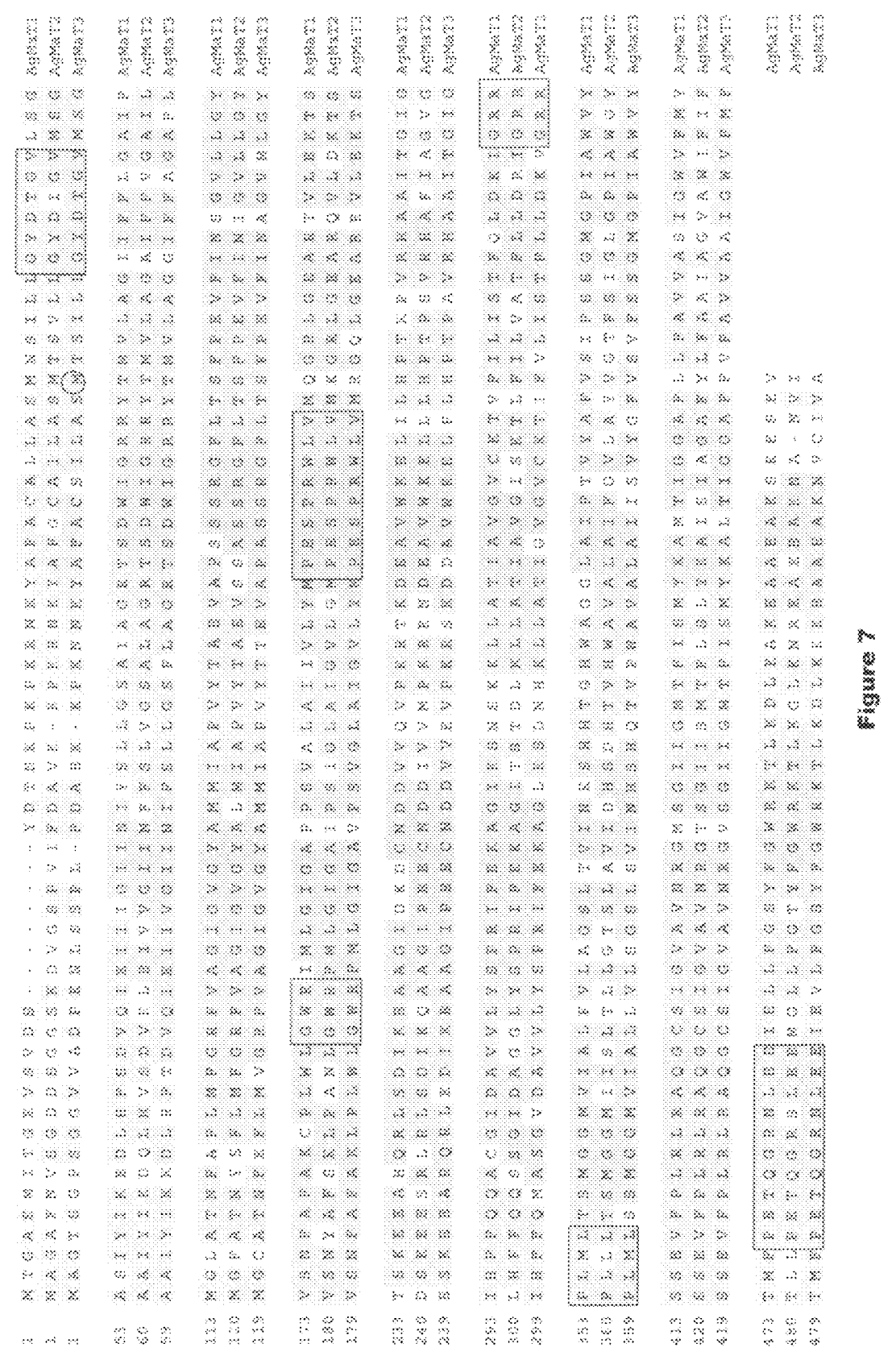

FIG. 7: Alignment of protein sequences of AgMaT1, 2 and 3. The deduced amino acid sequences were aligned using the Clustal method of the MEGALIGN program (DNAstar, Madison, WI). Residues identical to the consensus sequence are underlined. The boxed residues correspond to conserved sequences between the "sugar" transporters of the MFS family (according to NCBI Conserved Domain Search, ncbi.nlm.nih.gov/Structure/cdd/wrpsb.cgi). The boxed methionine corresponds to the start of the initially cloned protein sequence.

FIG. 8: Promoter and genomic sequence of AgMaT3 and translation of coding region. The said peptide sequence is given using the single letter abbreviation. The residues in italics correspond to the conserved sequences in the subfamily of MFS "sugar" transporters. Putative transmembrane helices are underlined. The numbering is based on the translation initiation site.

FIG. 9: Promoter sequence of AgMaT2 and translation of coding region. Said peptide sequence is given using the single letter abbreviation. The numbering is based on the translation initiation site.

FIG. 10: Promoter sequence of AgMaT3 and translation of coding region. Said peptide sequence is given using the single letter abbreviation. The numbering is based on the translation initiation site.

Figure 11:
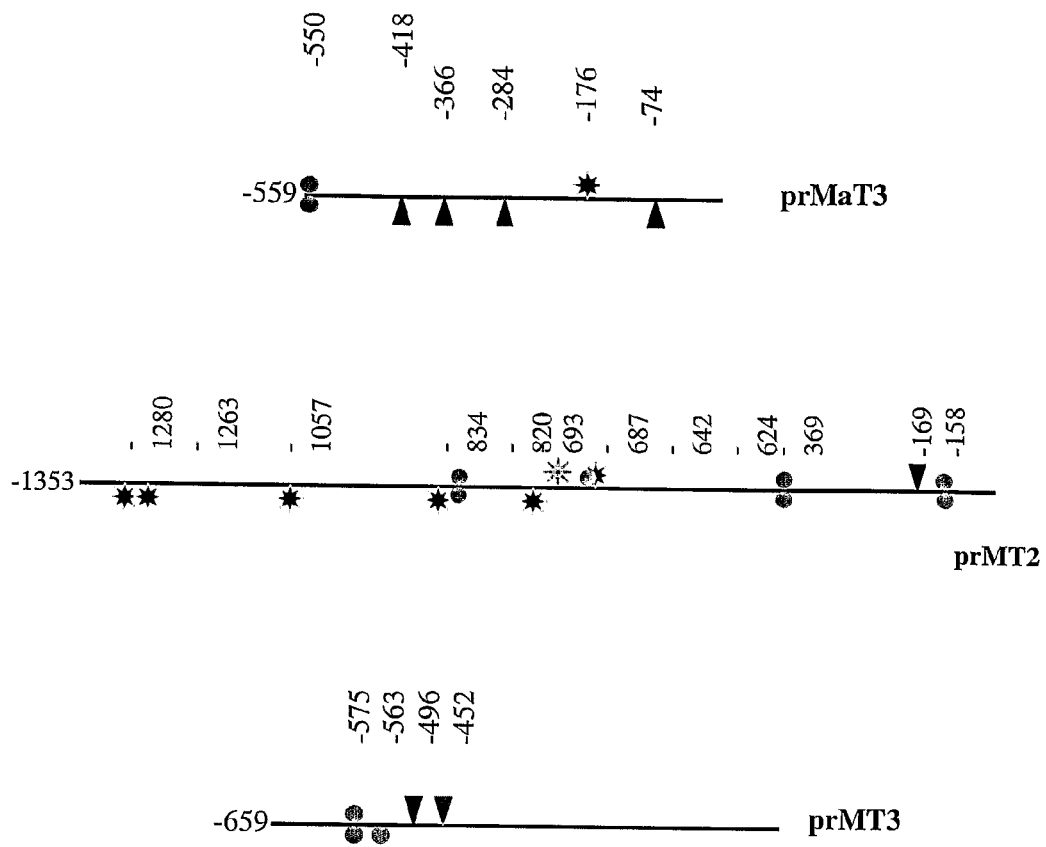

FIG. 11: Placement of certain cis elements (identified by data analysis) on promoter regions of AgMaT3 and AgMT 2 and 3, used for the constructs. The positions of the motifs are indicated as having the translation initiation site as the origin. The elements placed on the complementary strand (−) are shown below the line.

FIG. 12: Sequence of upstream 5' regions used as promoters. The sequences are shown to the first ATG corresponding to the translation initiation site. The cloned regions upstream of the reporter genes are underlined and their length is indicated in parentheses. The sequences SEQ ID NO: 1 (AgMaT3), SEQ ID NO: 2 (AgMT2) and SEQ ID NO: 3 (AgMT3) correspond to the underlined sequences; sequences SEQ ID NO: 4 (AgMaT3), SEQ ID NO: 5 (AgMT2) and SEQ ID NO: 6 (AgMT3) correspond to the bold sequences; they terminate just before the "A" of the ATG.

Figure 13:
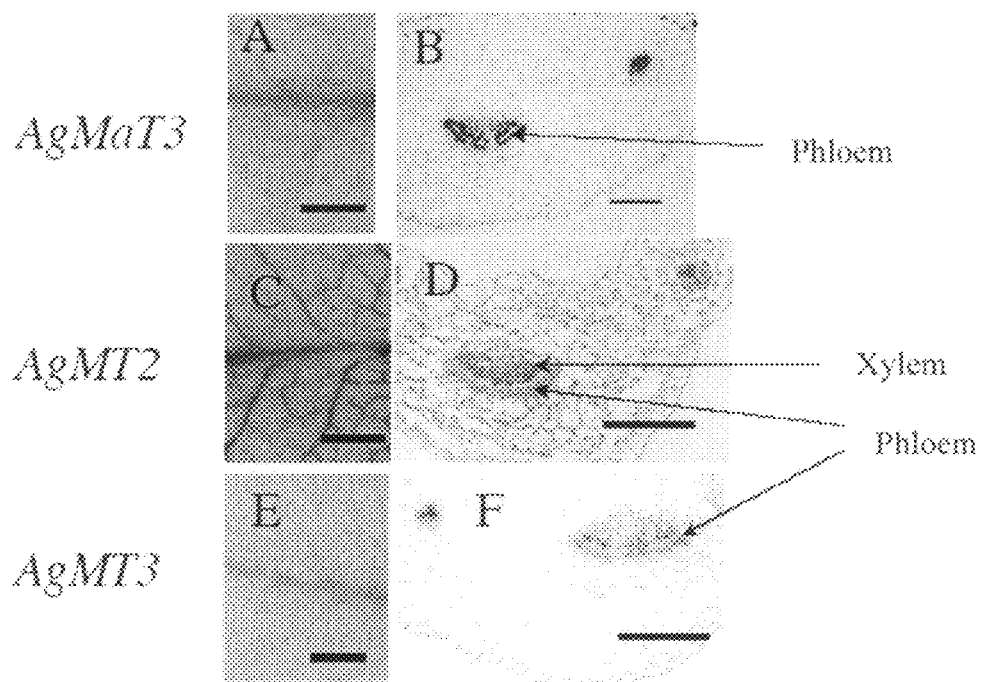

FIG. 13: GUS staining of mature leaves of *Arabidopsis* plants expressing the following constructs: AgMaT3::uiad (A, B); AgMaT2::uiad3 (C, D), AgMT3::uiad3 (E, F). The photographs show either the whole leaves (A, C, E scale bar 5 mm) or cross sections (B, D, F, scale bar 50 μm). All of the photographs were of plants following saline stress.

Figure 14A:
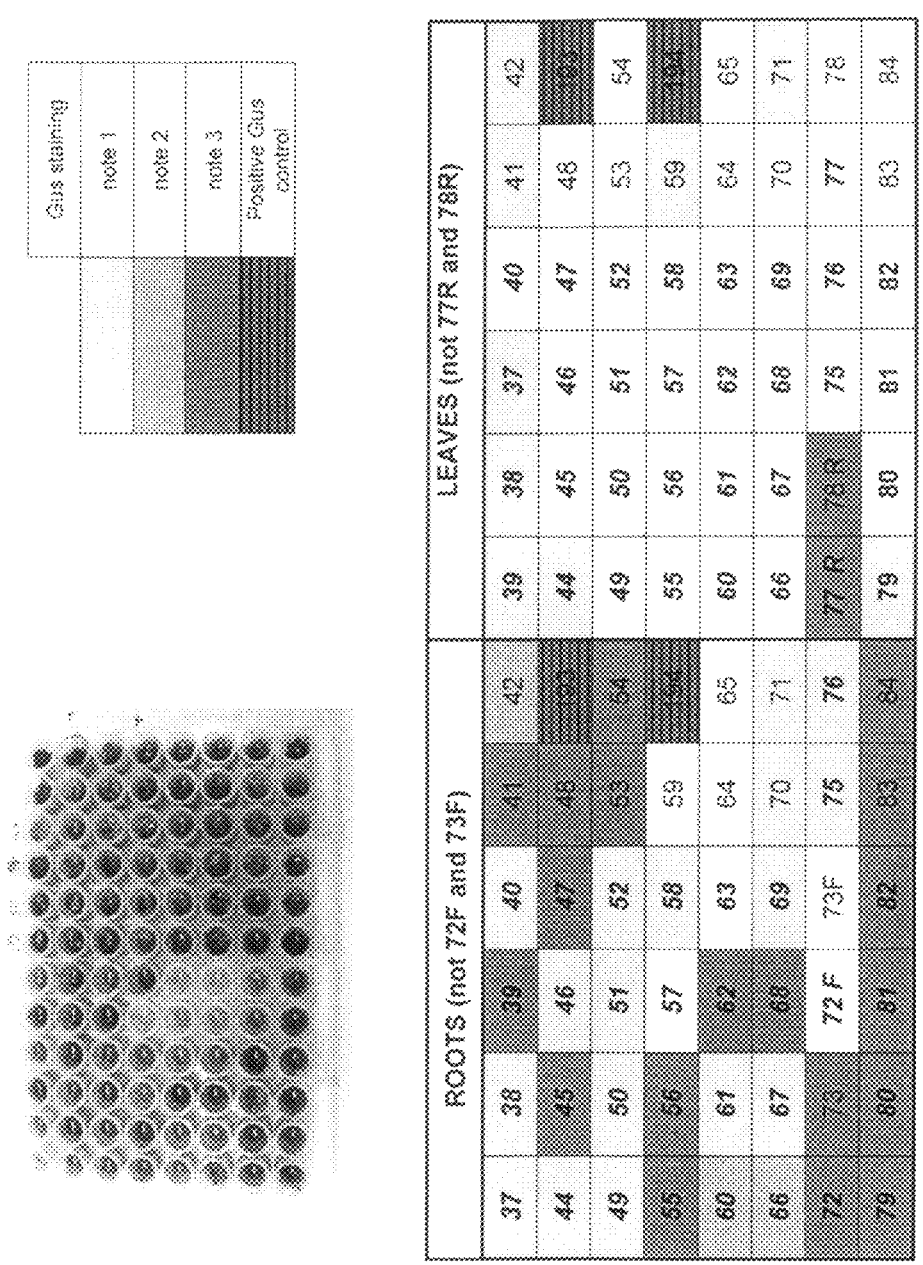
Figure 14B:
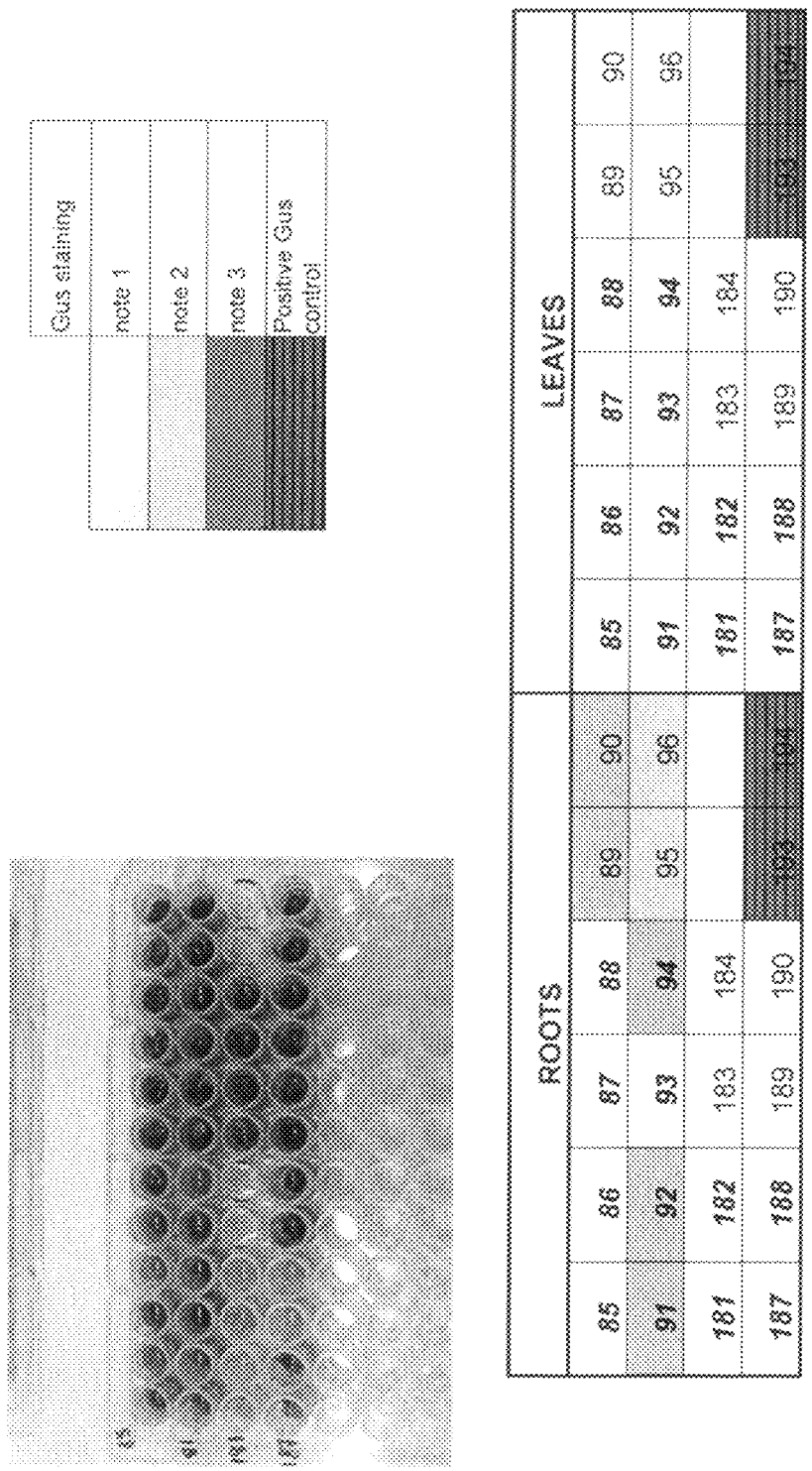

FIG. 14: Results of GUS test on root and leaf fragments from plants (Kemer tomatoes) transformed with the construct pAgMat3-GUS-tNOS. a) first plate: plants 37 to 84 and controls; b) second plate: plants 85 to 96 and controls. The plants which had been subjected to saline stress (50 mM for 4 days) are shown in bold italics. The GUS staining level is denoted 0 to 3. A positive GUS control under the control of a constitutive promoter and a non-transformed Kemer plant control were used as controls.

FIG. 15: Results of GUS test on fragments of stems and leaves from six plants (Kemer tomatoes) transformed with the construct pAgMT2-GUS-tNOS. The GUS staining level is denoted 0 to 3. A positive GUS control under the control of a constitutive promoter and a non-transformed Kemer plant control were used as controls.

Figure 16:
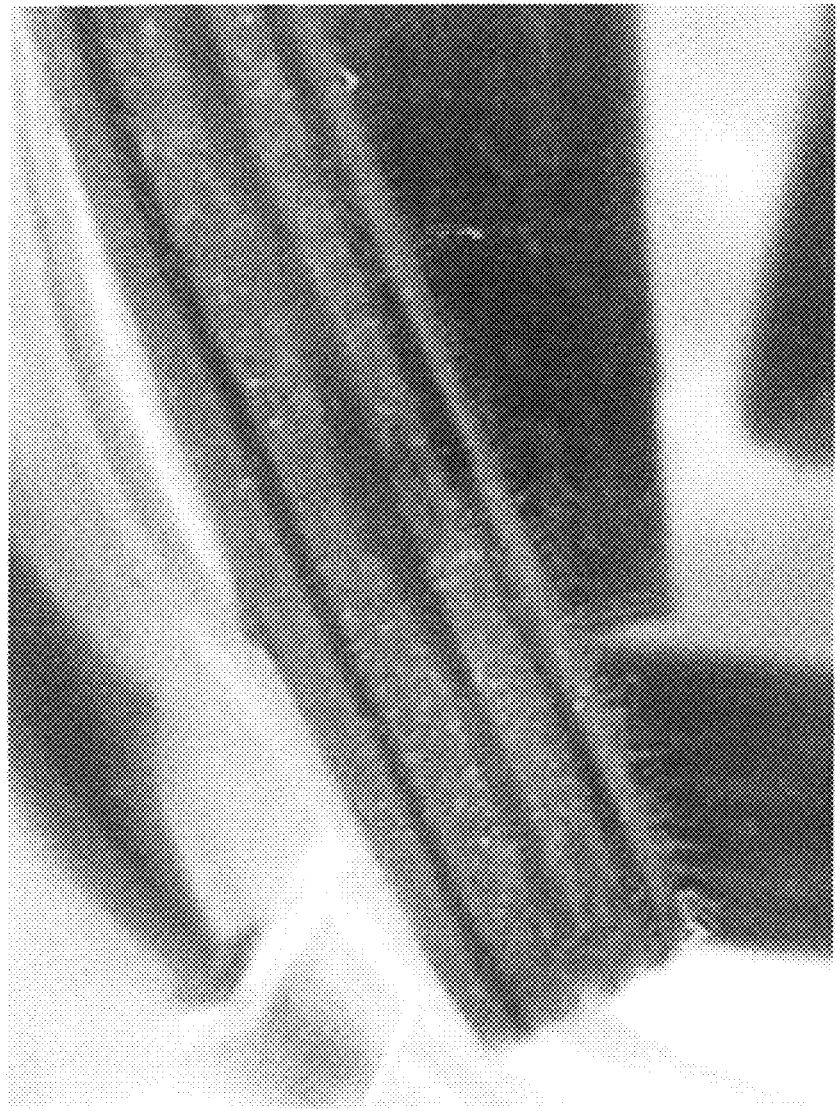

FIG. 16: Histo-cytological analysis of positive GUS fragments of plants (Kemer tomatoes) transformed with the construct pAgMT2-GUS-tNOS and observation of staining in vascular tissues. Observations were recorded 4 days following the test. The first observations show a rather concentrated blue stain on the vascular tissues of the stem, in some cases only on the ribs of the leaves.

FIG. 17: Tissue sections from plants (Kemer tomatoes) transformed with the construct pAgMT2-GUS-tNOS. Tissue sections from plant 13 at the stem (A) and plant 103 at the leaf (B) and stem (C). These cytological data indicate expression in phloem tissues.

EXPERIMENTAL SECTION

Bohnert's team (2001) carried out a large scale genomic study on various organisms (rice, *mesembryanthemum crystallinum* L, *Arabidopsis*, corn, tobacco and barley) in response to saline stress on various tissues (principally roots and leaves) at various stages of development and under highly varied conditions (concentrations and duration). This study was continued with insertional mutagenesis strategies and QTL (quantitative trait loci) carried out on rice to identify the characters allowing that species to be tolerant to saline stress (Koyama et al, 2001). General research was also carried out on the transcriptome of *Arabidopsis thaliana* treated with NaCl (Kreps et al, 2002) and on the rice proteoma (Salekdeh et al, 2002) in response to moderate salination (100-150 mM NaCl). These techniques which studied all of the genes and proteins expressed in the plant during saline stress can only be used when the whole of the genome of the species being studied is available, which is not the case with celery. Masmoidi's team (2001) investigated, by differential expression, the cDNA of what roots the expression of which was modified by treatment with 200 mM of NaCl. The technique used was much more targeted (to study the genes induced in a particular organ) but still could not identify many genes.

Thus, the present invention elected to use the subtractive library technique which allows both cloning of genes specifically induced by saline stress and the production of a large amount of cDNA, much more representative of the transcriptional state of the plant during this environmental constraint.

Further, there is little or no information regarding the tissue localizations of the various genes involved in salt tolerance. Phloem is a key tissue in the redistribution of $Na^+$ between the various organs (Lohaus et al, 2000). It is also involved in the transport of osmolytes to target accumulating tissues (Popova et al, 2003). Myo-inositol and ABA are transported rapidly to target tubes, acting as descending signals (from the leaves to the roots) and activating many mechanisms necessary to developing tolerance to saline stress (Nelson et al, 1999). It is recognized that phloem plays an important role in delivering informative molecules to remotely located organs (Ruiz-Medrano et al, 2001). Thus, it appears to be of interest to study the expression of genes during saline stress in this complex tissue. The inventors have worked on a subtractive library constructed from the phloem of plants which have undergone saline stress and phloem from a control plant (under normal hydration).

The plant which was best adapted for this study turned out to be celery, which is moderately sensitive to an excess of macroelements or to saline stress (de Pascale et al, 2003). This tolerance was in relation to an accumulation of mannitol (osmolyte) to the detriment of saccharose by modification of enzymatic activities, mannose-6-phosphate reductase and mannitol dehydrogenase (Noiraud et al, 2000). Celery has another advantage as the phloem tissue (cells of the phloem parenchyma+conductive complex) can readily be isolated microsurgically from the remainder of the conductive bundle (Noiraud, 1999). Thus, the stick celery variety apium graveolens L dulce (Vert d'Elne cultivar) was used by the inventors.

The aim was to identify promoters for genes induced in the phloem by a saline stress in celery using the subtractive library technique.

Example 1

Apparatus and Methods

1. Plant Material
IA Stick Celery
Crowns of stick celery were seeded and cultivated on the ground in a greenhouse. The plants were watered automatically for 90 sec every 3 hours during the day and received a solution of fertilizer (Peters solution 20:20:20 containing N, P and K, 100 ppm) three times per week. Once a week, the heart and young leaves were sprayed with 4 g/l calcium nitrate alternating with 10 g/l of Cosynol SC to prevent the celery from rotting (black heart disease).
IB Saline Stress (Celery)
When saline stress was applied, two batches of stick celery were prepared: "control" plants (T) and "stressed" plants (S). 5.4 l pots were covered with a black plastic film to limit evaporation. The saline stress started at a concentration of 25 mM of NaCl then was increased in 25 mM stages during each addition (two times 500 ml per pot and per day, morning and evening) of water or fertilizer up to the desired concentration, namely 300 mM NaCl. The control plants were watered in the same manner but without adding salt. The saline stress was applied for 3 weeks. Fertilizer and calcium were applied at the same frequency as with the control plants.
IC Harvest and Storage of Tissues and Organs
After 3 weeks of saline stress, the tissues were harvested in accordance with a predetermined criterion (age or size) and stored. A foliole, the parenchyma, phloem, xylem and petioles corresponding to the foliole and the roots were removed from several plants and combined in batches in accordance with the established criterion before being frozen in liquid nitrogen and stored at −80° C.
ID Culture of *Arabidopsis Thaliana*
Arabis is used for plant transformation by the promoter sequences of the various genes under study. Plants of *Arabidopsis thaliana* of the ecotype Columbia (Col-O) were sown and cultivated on the ground in a greenhouse under short day conditions (day~21° C., 8 h and night~17° C., 16 h) to develop the rosettes, then under long day conditions (day~21° C., 16 h and night~17° C., 8 h) to induce flowering until the floral spike lifted. The plants were watered automatically into their saucers for 90 sec every 3 h during the day and received a solution of fertilizer (Peters solution, 20:20:20 containing N, P and K, 100 ppm) three times a week.
II. Biological Material for Molecular Approaches
IIA. Host Microorganisms
IIA.1. Bacterial Strain
The bacterial strain *Escherichia coli* DH5α (GibcoBRL) was used for cloning and amplification of DNA and the PCR fragments. These bacteria were cultivated at 37° C. with a solid or liquid dYT medium in the presence of a suitable antibiotic; 100 µg/ml ampicillin; 100 µg/ml kanamycin or 50 µg/ml gentamycin.
IIA.2. Yeast Strain
The RS453 yeast strain (Sauer and Stadler, 1993) is incapable of developing on a medium without uracil. The PDR plasmid carrying the URA3 gene was used to transform this strain. This strain was cultivated with YPD medium if it had not been complemented, or if not on SC-glucose medium (no uracil).
IIA.3. Agrobacteria Strain
The agrobacteria strain used for transformation of flower spikes of *Arabidopsis thaliana* was *agrobacterium tumefaciens* LBA 4404. It was cultivated on YEB medium or in LB medium with agitation, at 28° C. in the presence of 100 µg/ml rifampicin and 200 µg/ml streptomycin.
IIB. Cloning Vectors
The maps for the cloning vectors used are given in FIG. 1. The vector used to clone the PCR fragments was the plasmid pGEM-T-Easy (Promega).
The expression vectors pDR 195 or pDR 196 were used to complement the strains of the *S cerevisiae* RS453 yeast. These vectors were used for heterologous expression of plant mannitol transporters in the yeast, under the control of the PMA1 promoter.
The plasmid pDONR 207 (Invitrogen) was used as a donor vector in the "Gateway Technology" (Invitrogen) kit.
The plasmids pBI 101-GUS-R1R2 and pBI 101-GFP-R1R2 have R1 and R2 borders (attR1 and attR2) which allow cloning of the promoter of interest upstream of the reporter genes GUS (β-glucuronidase, uidA) or GFP (green fluorescent protein 5-ER) by recombination between the inlet clone and the pBI destination vectors ("Gateway Technology" kit, Invitrogen) kit. After the recombination step, the vector BI 101 carried the reporter genes coding GUS or GFP under the control of the promoter being studied and the terminator NOS.
III. Methods
IIIA. Extraction of Total RNA from Plant Tissues
The technique used to extract total RNA has been described by Kay et al (1987).
IIIB. Cloning of DNA by Amplification (PCR)
IIIB.1. Amplification of Genomic DNA by PCR
10 ng of DNA was brought into the presence of 50 µl of reaction medium containing 250 µM of dNTP; 1 µM of sense and antisense primers; 1 U of DNA polymerase Taq enzyme "GoTaq" (Promega) and 1× of PCR buffer. Each cycle (after a first denaturing step of 1 min at 94° C. and followed by a last elongation step of 5 min at 72° C.) comprised: a 15 sec denaturing step at 94° C.; a 2 min hybridization step at a suitable temperature and an elongation step at 72° C. the duration of which was proportional to the size of the fragment to be amplified (1000 bp/min).
The primer pairs used for cloning into the vector pDONR207 were as follows:

```
To clone the promoter portion of AgMaT3:
5' Primer                                            (SEQ ID NO: 15)
5'-GGGGACAAGT TTGTACAAAA AAGCAGGCTG AACAGAAACAATTGTGGATG-3'

3' Primer                                            (SEQ ID NO: 16)
5'-GGGGACCACT TTGTACAAGA AAGCTGGGTA ATGTTGAGAA ACAATGGTCG-3'

To clone the promoter portion of AgMT2:
5' Primer:                                           (SEQ ID NO: 17)
5'-GGGGACAAGT TTGTACAAAA AAGCAGGCTG ACCCACTATC AACAATGATC-3'
```

-continued

```
3' Primer                                          (SEQ ID NO: 18)
5'-GGGGACCACT TTGTACAAGA AAGCTGGGTA TAAGATCGTT GTGGACTCTG-3'

To clone the promoter portion of AgMT3:
5' Primer:                                         (SEQ ID NO: 19)
5'-GGGGACAAGT TTGTACAAAA AAGCAGGCTT CTTTATTCTG CAGCTAGAGC-3'

3' Primer:                                         (SEQ ID NO: 20)
5'-GGGGACCACT TTGTACAAGA AAGCTGGGTG CTTGAAGTAA GGTGGTATGC-3'
```

The choice of hybridization temperature depends on prior computation of the melting point TM The amplification products obtained were analyzed on 1% agarose gel.

IIIB.2. DNA Amplification from Reverse Transcribed RNA (RT-PCR)

After denaturing 6 µg of total RNA at 70° C. for 10 min, reverse transcription was carried out for 60 min at 42° C. in the presence of 2.5 µM of oligo(dT)$_{18}$ primer, 500 µM dNTP and M-MLV reverse transcriptase (200 U, Promega). The RNA/cDNA heteroduplexes obtained were denatured for 5 min at 100° C. before PCR amplification of the target cDNA region was carried out by taking 2 µl of the synthesis medium of the first cDNA strand as the matrix.

IIIB.3. Cloning of PCR Fragments in pGEM-T-Easy Plasmid

The vector of the pGEM-T-Easy vector systems (Promega) system is a linearized vector adapted for direct cloning of PCR products using thymidine residues grafted to each of its 3' ends. The PCR products were ligated into 50 ng of pGEM-T-Easy plasmid in an insert/vector molar ratio of 3, overnight at 16° C. in the presence of 3 U of T4 DNA ligase (Promega kit). 3 µl of the 10 µl of ligation medium was used to transform 200 µl of competent bacteria.

IIIC. Transformation of Competent *Escherichia coli* Bacteria

The bacteria were rendered competent in the presence of CaCl$_2$.

IIIC.1. Preparation of Competent Bacteria

*E coli* DH5α bacteria were rendered competent using the method described by Sambrook et al (1989). The bacteria were then frozen in liquid nitrogen in 200 µl aliquots and stored at −80° C.

IIIC.2. Transformation of Thermocompetent Bacteria

Transformation of the competent *E coli* DH5α bacteria was carried out using the technique described by Sambrook et al (1989). Thermal shock was carried out at 42° C. for 90 sec. Addition of 800 µl of SoCt medium was followed by incubation at 37° C. with agitation for 1 h to allow phenotypical expression of the antibiotic resistance gene carried by the plasmid. The transformation medium was then spread over a dYT dish containing the appropriate antibiotic. These dishes were kept at 37° C. for 16 h.

IIID. Analysis of Plasmidic DNA

IIID.1. Minipreparation of Plasmidic DNA

This extraction is based on the bacterial alkaline lysis technique adapted by Sambrook et al (1989); a bacterial colony was cultured in 5 ml of dYT medium containing the appropriate antibiotic overnight at 37° C., with agitation. The cells from 3 ml of culture were concentrated by centrifuging for 1 min at 6000 g. The residue was resuspended in 200 µl of solution 1 (Tris HCl 25 mM (pH 8); EDTA 10 mM; glucose 50 mM] supplemented with 1 mg/ml final lysozyme, then after vortexing, 400 µl of solution 2 [0.2N NaOH; 1% SDS] and 300 µl of solution 3 [3M potassium acetate; 11.5% v/v glacial acetic acid; pH 4.8] were added in succession. After incubating for 5 min in ice, the cell debris was sedimented by centrifuging for 10 min at 14000 g. The supernatant was transferred into a clean microtube where RNase A at 100 µg/ml final was added before incubating at 65° C. for 15 min. The supernatant was purified by extraction with phenol/chloroform/isoamyl alcohol (25:24:1). The DNA was precipitated with one volume of isopropanol then rinsed twice with 70% ethanol, dried and taken up in 20 µl of water.

IIID.2. Establishing Restriction Profile

One microliter of plasmidic DNA solution (0.5 g/l) was digested with various enzymes of (3U) for 2 h at 37° C. The restriction products were analyzed on 1% agarose gel.

IIIE. Sequencing and Analysis of Clones

The most interesting clones were sequenced. Alignment of the nucleotide sequences, the investigation of restriction sites by endonucleases and also the investigation of open reading frames and the translation of DNA fragments into amino acids was carried out with Mac Molly Tetra (SoftGene GmbH) software. Comparisons with the sequences contained in the databanks were carried out using the BLAST program on the NCBI server (ncbi.nlm.nih.gov).

Promoter analysis and the investigation of specific boxes for recognition and binding of regulatory transcription proteins was carried out using the PLACE server (Higo et al., 1999, (DNA.affrc.go.jp/htdocs/PLACE/signalscan.html).

IIIF. Subtractive Library

This library represents all genes the expression of which is modified in a tissue following a given treatment. It was constructed using the "SMART PCR cDNA Synthesis" and "PCR-Select cDNA Subtraction" kits (Clontech) from total phloem RNA extracted either from "control" plants or from plants "stressed with 300 mM NaCl" for three weeks. The cDNA was directly produced and amplified from total RNA before enzymatic digestion by RsaI. The test cDNA (phloem from stressed plants S) was divided into two and each sub-batch was ligated with a different adapter giving S1 and S2. S1 and S2 were hybridized with driver cDNA (phloem from control plants T) in excess then combined and subjected to a second hybridization. The cDNA corresponding to genes expressed both under stressed conditions and control conditions are able to hybridize. Only cDNA from stressed plants which had not hybridized with a control homologue and having different adapters could be amplified and cloned.

IIIF.1. Cloning of Subtractive Library

The PCR products (fragments with 90 to 900 bp) were directly cloned into the pGEM-T-Easy vector (Promega) then into the *E coli* DH5α strain. The colonies obtained were distributed onto 96 well plates, cultivated in liquid dYT medium and stored at −80° C. (50% glycerol).

IIIF.2. Plate Minipreparation

Minipreparations were carried out directly on 96 well plates. The library was copied and cultivated onto deep well plates in 2 ml of dYT medium for 16 h at 37° C. and with agitation. After centrifuging (4000 g for 10 min at 4° C.), the residue was resuspended with 100 µl of solutions P1 (resuspension buffer, Qiagen), cold, with 50 µg/ml of RNase A, P2 (lysis buffer, Qiagen) and P3 (neutralization buffer, Qiagen), cold, with agitation until precipitates formed. After centrifuging, the supernatant was precipitated with one volume of isopropanol. Following fresh centrifuging, the residues were washed with 70% ethanol then dried and resuspended in TE buffer (25 µl; Tris 50 mM, EDTA 10 mM), with agitation. The final concentration of plasmidic DNA was determined by spectrophotometry.

IIIF.3. Deposition on Filters

Plasmidic DNA contained in each well of 96 well plates was denatured with NaOH (0.4M final) and deposited on nylon Hybond-N (Amersham; 8×12 cm) using a replicator. The plasmidic clones (100 ng) were deposited on the filters and fixed to the membranes by incubating at 80° C. for 2 h.

IIIF.4. Hybridization and Revealing of Filters

The filters were pre-hybridized for 4 h at 65° C. (complex probe) or at 42° C. (T7 probe) in a pre-hybridization solution [0.25M NaP buffer, pH 7.2 ($Na_2HPO_4$, $NaH_2PO_4$); SDS 6.6%, 1 mM EDTA, pH 8 and bovine albumin serum, 1%].

The radioactive "complex probe" was produced by reverse transcription on total RNA representing the genes expressed in a tissue following a given treatment, from anchored oligo-dT20. These probes would then hybridize differentially on clones deposited on the filters. The difference in intensity between the signals deriving from the "stressed" and "control" complex probes allowed the most interesting clones to be identified. The relative values obtained were readjusted by calibrating with an internal probe T7 of the deposited plasmid.

The first step of the reverse transcription reaction was denaturing at 70° C. for 10 min, of the mixed RNA and anchored oligo nucleotides (dT)20dA, (dT)20dG, (dT)20dC (2 µg of each). The denatured forms were stored by transferring directly onto ice. This RNA was then diluted in a mixture preheated to 42° C. for 5 min composed of RT 1× buffer Tris-HCl 50 mM, pH 8,3; KCl 75 mM; $MgCl_2$ 3 mM and DTT 10 mM), dNTP (0.8 mM of each except for dATP at 5 µM) and dATP-33P at 2.775 MBq in 7.5 µl (Amersham). Finally, 800 U of "MMLV reverse transcriptase" (Promega) was added to this PCR reaction and the mixture was incubated at 42° C. for 1 h and at 70° C. for 15 min, then cooled in ice (denature enzyme and conserve linearization of cDNA). So that there could be no interference with hybridization of the probe, the matrix RNA was destroyed by adding 8 U of ribonuclease H (Promega) at 37° C. for 30 min. The probe was stored on ice while awaiting verification of the incorporation of dATP-33P. Elution was carried out with water in 200 µl fractions and the radioactivity thereof was estimated using a scintillation counter (Packard, TRI-CARB 1900 TR). The fractions containing the probe were combined and used as the "complex probe" to hybridize the filters at 65° C. overnight.

The quantity of plasmidic DNA deposited on each spot was calibrated by hybridization with a T7 probe. This probe was produced from 100 ng of T7 oligo (20 mer) labeled at their (5') end with $\gamma ATP-^{33}P$ (1.85 MBq) fixed by reaction of "T4 poly nucleotide kinase (10U, Promega) in kinase 1× buffer (Promega) at 37° C. for 30 min, then blocked on ice. The filters were hybridized with the reaction product overnight at 42° C.

Hybridization of the filters was carried out for 16 h at 65° C. (complex probe) or at 42° C. (T7 probe) in the presence of radiolabelled probe diluted in the hybridization buffer (with the same composition as the pre hybridization buffer).

The filters were then washed twice for 10 min at 65° C. or at 42° C. in SSC 2×; SDS 0.1%; 10 min at 65° C. or 42° C. in SSC 1×; 0.1% SDS, 5 min at 65° C. or at ambient temperature in SSC 0.5×; SDS 0.1% (SSC 1×: NaCl 0.15 M and 0.015M of sodium citrate).

The filters were rolled into plastic bags and placed under "low energy" type screens (Kodak, Amersham) for six days inside exposure cassettes. The signals present on the filters were then quantified using the PhosphoImager system (STORM 820, Molecular Dynamics, Amersham) and expressed in relative units. The values obtained with the T7 probe (probe inside each plasmid) were used to calculated the relative intensities of the signal for each spot.

IIIG. Northern Type Hybridization

IIIG.1. Electrophoresis and RNA Transfer

The technique used for denaturing agarose gel electrophoresis and RNA transfer by capillarity onto a nylon membrane was that described by Noiraud et al, 2000. After transfer, the RNA was fixed on the membrane by incubation at 80° C. for 2 h.

IIIG.2. Preparation of Probe

The radioactive probe was prepared from a DNA fragment of interest. After enzymatic digestion, the DNA was separated on 1% agarose gel (Sambrook et al, 1989) of the insertion plasmid and purified on the "DNA gel extraction kit" column (Millipore). The DNA residue was resuspended in water at a final concentration of 125 ng/µl.

The radioactive probe was produced with the "Prime-a-gene labeling system" kit (Promega) based on hybridization of a mixture of hexanucleotides with the DNA fragment to be labeled, denatured. The hexanucleotides served as primers for the Klenow fragment which synthesized a complementary strand by incorporating $\alpha^{32}P$-dCTP. Synthesis of the probe was carried out at 25° C. for 2 h in the presence of 25 ng of denatured matrix DNA and $1.51 \times 10^6$ Bq of $\alpha^{32}P$-dCTP (specific activity 220 TBq/mmol). At the end of the reaction, the unincorporated nucleotides were separated from the probe by passing the mixture over a Sephadex G-50 column. The fractions containing the probe were combined, denatured at 95° C. for 3 min and stored in ice until use.

IIIG.3 Northern Hybridization

The membrane was pre hybridized for 4 h at 65° C. in the pre hybridization solution. Hybridization was carried out for 16 h at 65° C. in the presence of the radiolabelled homologous probe (celery/celery hybridization). The membrane was then washed twice for 15 min at 65° C. in SSC 2×; SDS 0.1%, 30 min at 68° C. in SSC 1×; SDS 0.1%, 15 min at 68° C. in SSC 0.5×; SDS 0.1%.

The membrane was rolled up into a plastic bag and placed on screens for 3 hours. The RNA deposits were calibrated with a 26S celery ribosomal probe labeled with $\alpha^{32}P$-dCTP.

IIIH. RACE-PCR

The coding sequences and the non translated 5' and 3' portions were cloned using the "Marathon cDNA amplification kit" (Clontech) from total phloem RNA extracted either from "T control" plants or from "S stressed" plants. The primers used for these clones were selected in accordance with the kit requirements. The PCR products were complementary DNA and were cloned directly into the pGEM-T-Easy vector (Promega) then into the *E coli* DH5α strain.

IIII. Real Time RT-PCR

Real time RT-PCR was carried out from RT (reverse transcription) on which PCR was carried out from primers (Invitrogen) and Taqman probes (Applied Biosystems, UK). These were selected from the untranslated 3' regions of the coding sequence of the test mannitol transporters. These regions had the least similarity between them and so the signal obtained was specific to expression of one of these transporters.

Quantitative RT-PCR was carried out essentially as described in Wagner et al, 2001.

The specific primers for AgMaT3 were:

5'- ATA CAG CGG GGA TTA TAG CTT TG -3' (SEQ ID NO: 21) and

5'- ATC CGC AGG TAC TCC AAA AAT TT -3' (SEQ ID NO: 22), to amplify a 101 base pair fragment specific to the non coding 3' region. The amplified fragment was verified by sequencing. The FAM labelled probe was 6 FAM-TAC CCG GTA TAT TCA CTC-MGB (SEQ ID NO: 23) (synthesised by Applied Biosystems).

To amplify Ag26S (control gene), the primers used were 5'-AGC CGC TGG ACC CTA CCT-3' (SEQ ID NO: 24) and 5'- AGT TAT CTT TTC TGT TTA ACA GCC T-3' (SEQ ID NO: 25), while the fluorescent probe was 6 FAM-CTA AGC CGT TTC CAG G-MGB (SEQ ID NO: 26).

The primers and probes were determined using Primer Express, v.1.0 software (Applied Biosystems).

The fragments were obtained by PCR in the presence of "Taqman Universal PCR Master Mix" 1× (Applied Biosystems, Roche), 0.9 µM of each 5' and 3' primer, 0.2 µM Taqman probe and RT product diluted to 1/300 (RT produced from 10 µg of total RNA). The fluorescence emitted by the Taqman probes was detected using the ABI PRISM 7700 (Applied Biosystems) detection system. The signals were quantified using 26S ribosomal probes from celery. This produced Ct values defined as the number of cycles at which the normalized value ΔRn (intensity of fluorescence of reporter stain) exceeded a threshold value generated by the software. Thus, Ct was inversely proportional to the concentration of the target sequence.

IIIJ. Cloning of Promoters and Genomic Sequences

The genomic sequences (introns+exons) and the known sequence promoters were obtained using a technique based on PCR, breaking free of all of the screening steps (phage library) normally used. Genomic DNA was divided into four batches, each being digested with a different enzyme. The enzymes selected produced blunt ends. Depending on the position of the restriction sites, the fragments obtained will vary in size. Adapters with known sequences were then ligated to the ends of the digestion fragments. On each of the 4 batches, PCR was carried out with a specific primer of the gene studied (GSPI) and a specific primer of the adapter (AP1). The second or "nested" PCR was carried out on the product of the first, with primers (GSP2 and AP2) which were more internal than the first, to optimise the specificity of the result. Up to 4 PCR fragments of varying size were obtained. The longest one, carrying the most information, was purified.

IIIJ.1. Extraction of Genomic DNA

Tissues (young folioles) were ground into a fine powder in a mortar in the presence of liquid nitrogen. Fifteen millilitres of CTAB 2× buffer [CTAB 2% w/v; NaCl 1.4M; EDTA 20 mM; Tris 100 mM (pH 8); β-mercaptoethanol 0.2% v/v] preheated to 60° C. was added per 3 to 5 g of ground powder and incubated for 30 min at 60° C. The proteins and cell debris were eliminated by extraction with chloroform/isoamyl alcohol [24:1 v/v] followed by precipitation with cold isopropanol (0.5 volume) and at −20° C. for 30 min. If DNA filaments were visible, it was then possible to catch them and wash them with 76% ethanol containing acetate-$NH_4$, 10 mM final, for 20 min. if not, it was centrifuged at 5000 g for 5 min and the residue was washed in the same manner. The DNA was then centrifuged again and the residue was air dried then taken up in 1 ml of TE buffer [Tris 50 mM; EDTA 10 mM] supplemented with RNase A, 10 µg/ml final, and incubated for 30 min at 37° C. The gDNA was precipitated by adding 1.5 ml of TE buffer, 0.5 ml of NaCl (5M) and 2 ml of cold isopropanol in succession. After centrifuging at 5000 g for 10 min, the residue was washed with 70% ethanol, dried in air and taken up in TE buffer (50 µl).

The quantities of DNA were estimated by spectrophotometric assay between 210 and 310 nm. An absorbance of 1 at 260 nm corresponded to a concentration of DNA of 50 µg/ml.

IIIJ.2. Construction of Genomic Library

The genomic library was constructed using the "universal genome walker" kit (Clontech) from genomic DNA. The primers used were selected in accordance with the instructions in the kit. The PCR products obtained were cloned directly into the pGEM-T-Easy vector then into the *E coli* DH5α strain for minipreparation and sequencing.

IIIK. Transformation of *Arabidopsis thaliana* with a Celery Promoter Upstream of a Reporter Gene IIIK.1. Gateway Technology The expression profile of the promoters was followed by transferring their sequence upstream of a reporter gene. Gateway technology allowed a DNA fragment (complementary or genomic) to pass from its PCR product into a "donor vector" (pDONR 207) then into a "destination vector" (pBI-GUS-R1R2 or pBI-GFP-R1R2).

The primers produced (Invitrogen) to clone these promoters contained the attB sequences and were selected in accordance with the criteria in the "Gateway Technology" kit (Invitrogen). The PCR experiments were carried out on genomic DNA obtained as described in IIIJ.1. after each ligation, the plasmids obtained were amplified in the *E coli* DH5α strain. The plasmids used contain the ccdB gene: it is lethal in the majority of bacteria. Thus, only plasmids which have carried out the recombination reaction (insertion of the DNA fragment and excision of the ccdB gene) can be amplified in the bacterium.

IIIK.2. Transformation of Electrocompetent Agrobacteria

IIIK.2a. Preparation of Competent Agrobacteria

The preparation of *A tumefaciens* LBA 4404 agrobacteria was carried out as described by Koncz and Schell (1986) to prepare aliquots of 40 µl (cell concentration $3 \times 10^{10}$ cells/ml) which were stored at −80° C. before use.

IIIK.2b. Transformation of Agrobacteria by Electroporation

Electroporation tanks were placed on ice at 4° C. An aliqot of agrobacteria (40 µl) was defrosted and 2 µl of plasmidic DNA solution was added; it was then deposited in the tanks. The agrobacteria suffered an electric shock of 5 msec duration at 15 kV/cm. Immediately, 960 µl of YEB medium was added then the suspension was transferred and incubated at 28° C. with agitation for 1 h to allow phenotypical expression of the antibiotic resistance gene carried by the plasmid. The transformation medium was then spread onto a YEB dish containing appropriate antibiotics placed at 28° C. for 16 h.

IIIK.3. Transformation of *Arabidopsis thaliana*

*Arabidopsis* transformation was carried out using the method described by Clough and Brent (1998), the transformed agrobacteria being cultivated until an absorbance of 0.8 at 600 nm was obtained then used to transform flower spikes of *Arabidopsis thaliana*.

IIIL. Study of Functional Heterologous Expression of Plant Transporters in the Yeast *Saccharomyces Cerevisiae*

IIIL.1 Cloning of cDNA in PDR Expression Vector

The PDR vector has the PMA1 promoter and the ADH terminator which allow expression of transporters in the yeast. The cDNA sequence was extracted from the amplification vector (pGEM-T-Easy) by enzymatic digestion with the same restriction enzymes (3 U, 2 h at 37° C.) which cut the PDR vector to produce orientated cloning. The digestion products were monitored and purified on 1% agarose gel. The PDR plasmid digested was then dephosphorylated using the shrimp alkaline phosphatase enzyme (4 U, Promega) for 1 h at 37° C., preventing its re-circularization. The various enzymes were inhibited after each reaction for 15 min at 65° C. Ligation of the cDNA of the transporter in PDR was then possible using T4-DNA ligase (3 U, Promega) overnight at 16° C., using an insert/vector ratio of 3. The prepared vector was amplified in the *E coli* dh5α strain before transformation of the yeasts.

Preparation of Competent Yeasts then their Transformation was Carried Out Using the Protocol of Dohmen et al (1991).

IIIL.2. Absorption of Polyols by Transformed Yeasts

IIIL.2a. Preparation of Yeasts for Absorption

The yeasts were prepared using the method described by Noiraud et al (2001).

IIIL.2b. Absorption of Radiolabelled Mannitol and Sorbitol by Yeasts

The absorption of radiolabelled polyols, mannitol and sorbitol yeasts was measured using the method described by Noiraud et al (2001); a hundred μl of yeast suspension was incubated at 28° C. in the presence of 100 μl of a solution containing 1.1 mM of mannitol (0.55 mM final) with 5.8 kBq of mannitol[2-3H] (specific activity $6.3 \times 10^8$ kBq/mol). For the sorbitol absorption test, 100 μl of yeast suspension contained 1.1 mM of total sorbitol (0.55 mM final) with 16.6 kBq of $^{14}$C-sorbitol (activity $1.02 \times 10^7$ kBq/mmol).

IIIL.2c. Assay of Proteins on Yeasts

500 μl of cells prepared for absorption, washed and resuspended in SC MES without uracil, was deposited in a test tube and made up to 2 ml with water. 500 μl of 15% NaOH was added and it was heated to boiling point for 5 min. After cooling, 175 μl of 11.75N HCl was added to neutralize the solution and the solution was vortexed.

The proteins were assayed using the Bearden technique (1978) based on the color change of Coomassie blue when it binds to a protein.

Example 2

I. Saline Stress and Celery

In order to constitute a reserve of tissues for the construction of a subtractive library and the production of complex probes, celery was subjected to a saline stress by modifying certain conditions compared with treatments carried out previously (Noiraud, 1999). In order to standardize the organ harvesting conditions, the real age of the leaves (from the date of emergence) rather than their general appearance (for example size) was taken in to account. Stress has a negative effect on growth and leaf development: a stressed leaf and an untreated leaf may appear identical but not have the same age.

Of nine plants of each batch (controls and stressed), six were used to harvest tissues and extract the RNA necessary for the production of libraries and probes. Only the phloem from leaf petioles which had reached an age of 3 weeks was used for the construction of the subtractive library. These leaves had developed entirely under stress conditions.

General Appearance of Saline Stress in Plants

After 3 weeks treatment with 300 mM NaCl, growth of the plants had been affected. Observation of the general appearance of celery plants (FIG. 2) showed a difference in size and volume between the stressed and control plants in correlation with the reduction in growth rate and the absence of leaf emergence in the plants treated with NaCl.

During saline stress, celery growth slows and new leaf emergence slows. Growth inhibition is a stress tolerance strategy. This slowdown is reversible, as if the plants after 3 weeks saline stress are watered with a solution containing no NaCl, then growth and leaf emergence is rapidly re-established at a level identical to that noted before saline stress.

The most exterior leaves (the oldest) become senescent more rapidly, which could indicate a strategy for eliminating toxic ions from the youngest organs by accumulating them and sequestrating them in the senescent organs. This sequestration in old leaves represents a saline stress tolerance strategy. In celery, it is important to preserve the plant meristem intact so that it can become inflorescent.

This strategy must be coordinated on the whole plant scale. This is possible by triggering a new gene expression program. It is these genes which are specifically induced by this type of stress which have been characterized by the inventors. This study concentrates on the phloem which plays a preponderant role in inter-organ exchanges of nutrient molecules and informational molecules.

II. Production of a Subtractive Library

To identify the genes specifically induced by saline stress, a subtractive library was produced using the PCR select cDNA subtraction kit from Clontech which could identify genes the expression of which is stimulated under a given physiological condition (in this case saline stress). In theory, only these genes are obtained at the end of the analysis. The cDNA corresponding to the genes which are constitutively expressed in the normal state are subtracted from the cDNA of stressed plants. PCR cycles can amplify the genes specific to saline stress.

The quantity of phloem tissue extracted is more limited than with leaves, and so a supplemental initial amplify step for the messengers was introduced (Smart PCR cDNA synthesis kit, Clontech). The subtractive library was produced in accordance with the manufacturer's instructions (PCR select cDNA subtraction kit, Clontech). Although a first phloem subtractive library was constructed and produced good results regarding a saline stress response (including thermal shock proteins and a casein kinase 1 subunit), the quantity of clones obtained was too low to constitute a library.

A new phloem subtractive library was produced and provided the results detailed below: the mean insert size was in the range 90 to 900 bp. The clones obtained after subtraction and amplification were ligated into the pGEM-T-Easy vector (Promega). The colonies (the largest, i.e. 736 of 750) were individually cultivated on 96 well plates. Replication was carried out with a view to preservation after freezing at −80° C.; another replicate was cultivated to extract plasmidic DNA by minipreparation.

IIA. Development of Subtractive Library Screening System

The number of clones obtained by the subtractive library was much too high (736 for the phloem subtractive library) to be able to analyze them independently. To refine the investigation, plasmidic DNA from the clones obtained was deposited on the filters which were hybridized with complex probes produced from RNA extracted from "stressed" tissues or "control" tissues. The signals were then quantified and analyzed and clones which were positive (depending on the NaCl/control ratio) were retained. The radioelement selected for labeling the probes was phosphorus 33 with a concentration of 50 ng/µl of plasmidic DNA.

IIB. Deposit and Hybridization of Clones Obtained Following Subtractive Library

Nitrocellulose filters (96 wells) were produced to identify the clones: the minipreparations were carried out on plates onto which host bacteria were grown after replication of the frozen library. Thus, 736 independent clones could be deposited on a membrane and analyzed. The membranes were hybridized with complex probes produced by $^{33}$P labeling following reverse transcription on RNA extracted either from control phloem or from phloem from stressed plants. The radioactive labels obtained were counted (Phospholmager) and compared. Thirty clones exhibited a strong signal under stress conditions and their plasmidic DNA was sequenced (Table I).

TABLE I cDNA sequences obtained from the phloem subtractive library which demonstrated a high stress/control ratio during differential hybridizations. The approximate size of these fragments is indicated in base pairs. The corresponding homology and accession number were obtained by comparison with BLAST databases.

| Size (bp) | Functional annotation | Homology | Accession number | BLAST E-value |
|---|---|---|---|---|
| 500 | Oxidoreductase, Zn-binding dehydrogenase | Arabidopsis | NP_173786 | 5.1 |
| 300 | No results | — | — | — |
| 90 | Metallothionein AgMT2 | P brachycarpa | AAC62510 | 1e−04 |
| 440 | Chlorophyll a/b binding protein of CP29 | Tomato | CAA43590 | 3e−43 |
| 350 | 14-3-3 family protein | Tomato | P93211 | 3e−58 |
| 310 | No result | — | — | — |
| 800 | NiFU-like protein or dehydrin | Arabidopsis Barley | NP_193953 AAD02257 | 1e−05 0.001 |
| 800 | Beta-galactosidase | Arabidopsis | T00787 | 2e−35 |
| 700 | Hypersensitive-induced reaction protein | Barley | AAN17454 | 6e−44 |
| 320 | Unknown | Arabidopsis | AAK31144 | 1e−05 |
| 150 | No result | — | — | — |
| 600 | Chlorophyll a/b-binding protein | Tomato | S14305 | 6e−23 |
| 170 | No result | — | — | — |
| 180 | Mannitol transporter AgMaT3 | Celery | AAG43998 | 2e−20 |
| 350 | Metallothionein AgMT3 | Vine | CAB85630 | 2e−09 |
| 470 | dnaK-type molecular chaperone hsc70 | Tomato | JC4786 | 2e−76 |
| 660 | High molecular weight heat shock protein | Apple | AAF34134 | 5e−40 |
| 900 | Lipid transfer protein | Arabidopsis | NP_177181 | 3e−13 |
| 400 | Fiber annexin | Cotton | T31428 | 1e−58 |
| 800 | RUB1 conjugating enzyme | Tomato | AAG23847 | 5e−54 |
| 900 | Cinnamyl-alcohol dehydrogenase | A cordata | P42495 | 2e−69 |
| 620 | 40S ribosomal protein S27 | Arabidopsis | NP_191670 | 2e−33 |
| 600 | 60S ribosomal protein L30 | Lupin | O49884 | 1e−55 |
| 650 | 60S ribosomal protein L28 | Arabidopsis | NP_194670 | 7e−41 |
| 450 | No result | — | — | — |
| 250 | No result | — | — | — |
| 250 | No result | — | — | — |
| 640 | No result | — | — | — |

IIC. Results and Bibliographic Interpretation of Positive Clones in Relation to Stress and Phloem Of the 30 positive clones, sequences could be identified which exhibited similarities with genes the role of which in stress has been documented (in particular proteins thermal shock, HSP, dehydrins and metallothioneins). Three sequences were identical and belonged to the same gene and 8 others did not correspond to anything which was known. Of the remaining 21, 3 sequences were studied in more detail.

IIC.1. AgMaT3, a Third Mannitol Transporter in Celery?

The partial sequence discovered was very similar to 2 other mannitol transporters identified in celery: AgMaT1 and AgMaT2 (Noiraud et al, 2001a). The partial sequence isolated from the phloem subtractive library is slightly different and was denoted AgMaT3.

Transporters such as AgMaT3 could play an important role in tolerance to saline stress by allowing transport of osmoprotectants such as mannitol in the plant.

This transporter represents a good candidate in response to saline stress in phloem.

IIC.2 Metallothioneins

Four sequences corresponded to metallothioneins (MT). Two were completely identified and belonged to the 3' region of AgMT2 (apium graveolens metallothionein 2). A third sequence was also homologous to AgMT2 but located upstream of the preceding two. A fourth sequence also corresponded to a metallothioneins but was homologous to AgMT3. These denominations were attributed in accordance with Vilaine et al (2003).

Metallothioneins are small proteins with a low molecular mass which are rich in cysteins and are capable of binding metals (Zn, Cd) found in all species, both animal and plant, and in prokaryotes. They are also involved in the response to stress such as treatments with metal ions, thermal shock (Hsieh et al, 1995), glucose and saccharose deficiency (Chevalier et al, 1995) or in the case of high concentrations thereof (Chatthai et al, 1997), at low temperatures (Reid and Ross, 1997), injury and viral infection (Choi et al, 1996).

IID. Complementary Analysis of Clones

The analysis of the subtractive library revealed a certain number of sequences induced by saline stress. Although these libraries were produced from RNA deriving from phloem, this does not exclude that the identified genes are also expressed in other tissues. For this reason, the location of the sequences obtained was determined by reverse Northern blot to validate their phloem specificity. The thirty clones exhibiting the most positive signals following analysis of the library on the filter were deposited onto minifilters hybridized by the novel complex probes produced from RNA extracted from phloem or xylem from "control" or "stressed" celery petioles (PhT and PhN or XT and XN respectively). Ten clones were retained following this analysis as specifically induced by saline stress; some of them had a high phloem/xylem ratio (Table II).

TABLE II cDNA sequences obtained after differential hybridizations from the phloem subtractive library with complex probes. The approximate size of these fragments is indicated in base pairs. The clones are classified in accordance with the specificity of their expression during saline stress in phloem. Only clones with a ratio of more than 2 are inserted in the table. The ratio between phloem and xylem was calculated after hybridization with complex probes obtained from RNA extracted from phloem and xylem of plants stressed by salt.

| Size (bp) | Functional annotation | Homology (accession no) | BLAST E-value | Stress/control ratio | Phloem/xylem ratio |
|---|---|---|---|---|---|
| 500 | Oxidoreductase, Zn-binding dehydrogenase | *Arabidopsis* NP-173786 | 5.1 | 30.8 | 5.6 |
| 350 | 14-3-3 family protein | Tomato P933211 | 3e−58 | 13.0 | 0.3 |
| 440 | Chlorophyll a/b binding protein of CP29 | Tomato CAA43590 | 3e−43 | 10.1 | 0.4 |
| 350 | Metallothionein AgMT3 | Vine CAB85630 | 2e−09 | 10 | 6.8 |
| 700 | Hypersensitive-induced reaction protein | Barley AAN17454 | 6e−44 | 4.2 | 3.8 |
| 650 | NiFU-like protein or dehydrin | *Arabidopsis* NP_193953 | 1e−05 | 3.3 | 0.7 |
| 310 | No score | | | 2.8 | 0.4 |
| 90 | Metallothionein AgMT2 | *P brachycarpa* AAC62510 | 1e−04 | 2.4 | 1 |
| 180 | Mannitol transporter AgMaT3 | Celery AAG43998 | 2e−20 | 2.7 | 1 |
| 800 | Beta-galactosidase | *Arabidopsis* T00787 | 2e−35 | 2.3 | 1 |

The screenings were normalized using a T7 probe (internal probe of plasmid used for cloning the library). The clones of interest included the mannitol transporter AgMaT3 and metallothionein MT2. The metallothionein MT3 is also included, but the signal in the control phloem was zero although the phloem/zytokine ratio was high.

To refine these results, Northern blot experiments were carried out by depositing RNA extracted from phloem, xylem and parenchyma storage of control or stressed celery petioles. The membranes were hybridized with radiolabelled probes produced from sequences selected for their tissue specificity (the inserts of the test clones were extracted by digestion and purified before labelling). The results of these hybridizations are shown in FIG. 3. These hybridizations were quantified using a ribosomal 26S celery probe and the intensities were measured using a revealing system (PhosphImager: STORM820). The values obtained are given as a percentage: 100% for expression of each probe in the "control" phloem (PhT); the comparisons were carried out from this tissue (FIG. 4).

The AgMaT3 probe was more specifically fixed on the "stressed" phloem (PhN, 225%), confirming the preceding results. The expression of AgMaT3 was also stimulated by saline stress in the storage parenchyma (PaN, 171%) and in the xylem. The results of the Northern blot confirm that AgMaT3 is a gene the expression of which is regulated by saline stress.

The two metallothioneins AgMT2 and AgMT3 reacted in different manners. AgMT3 is principally expressed in the phloem and this expression is very strongly stimulated following saline stress (224%). The stimulation of expression of AgMT2 in phloem following saline stress was not as strong (133%). Expression of these two metallothioneins was principally observed in the phloem of the control and stressed plants (even if it is also stimulated in the xylem following saline stress, expression remained significantly lower than that measured in the phloem). Thus, metallothioneins are specific to the phloem and expression thereof, especially for AgMT3, is effectively induced by saline stress.

IIE. Conclusion

The aim of this first section was to identify genes the expression of which is induced (or stimulated) in the phloem of celery during saline stress. The production of a subtractive library necessitated developing a maximum number of clones: the final step for amplification of the library could only be carried out using a bacterial strain which was different from that recommended by the kit manufacturer. The first analyses on a reduced number of clones selected at random showed that the subtraction had been effective. The large number of clones obtained led the inventors to seek a system which could control the efficiency of the subtraction. The minifilters produced allowed more than 700 clones to be tested for their capacity to preferentially hybridize RNA from the phloem of stressed plants over control plants. Normalization of the signal was carried out using the T7 probe present in the cloning plasmid.

The clones reproducibly providing the most intense signals were sequenced and underwent a data analysis (Table I). To refine these results and verify whether the sequences identified were actually specific to phloem and saline stress, the corresponding 29 plasmids were re-deposited on a new membrane and underwent hybridizations with radiolabelled probes produced from the phloem of stressed or unstressed plants but also from the xylem of the same plants, keeping only the sequences exhibiting a specificity and induced by saline stress. A limited number of sequences was thus selected before a final Northern blot verification, including storage parenchyma as the supplemental tissue. From these results, it appears that the 2 metallothioneins as well as the mannitol transporter AgMaT3 clearly have the most interesting profiles.

The various results obtained persuaded the inventors to continue the studies by identifying promoters of the interesting genes, namely metallothioneins 2 and 3 and the novel mannitol transporter AgMaT3.

The next step was thus investigation of the promoter of these genes using a gene library and monitoring their activation in the various organs and tissues of the plant during saline stress.

III. Characterization of AgMaT3, a Novel Mannitol Transporter in Celery

Analysis of the subtractive library of phloem allowed thirty clones exhibiting a strong signal under stress conditions to be retained of the 736 clones deposited on the membranes. A partial sequence (181 bp) was retained as it corresponded to a mannitol transporter, a compound qualified as a "compatible solute" in response to saline stress. Currently, 2 mannitol transporters have been identified in celery: AgMaT1 and AgMaT2 (Noiraud et al, 2001a and b).

III1. RACE-PCR on the Partial Sequence of AgMaT3

RACE PCR was carried out on the cDNA produced from polyA RNA extracted from stressed phloem to which adapters had been ligated, to amplify the 5' and 3' portions. These cDNA sequences 5' and 3' were amplified by PCR between primers selected from the partial sequence of 181 bp (from the phloem subtractive library) and specific adapter primers in accordance with the guidelines in the "Marathon cDNA amplification" kit (Contech). These primers were selected so that the 5' and 3' fragments could overlap and align to reconstitute the complete cDNA sequence. Once the 5' and 3' sequences had been obtained, new primers were designed to amplify the whole of the AgMaT3 cDNA (5' primer: 5' GAC TAG TCC CAA GAA TCT GAG TTC ACC-3' (SEQ ID NO: 27) and 3' primer: 5'- CCG CTC GAG CAT CAC AAA GCT ATA ATC C-3'(SEQ ID NO: 28).

The cDNA of AgMaT3 has a total length of 1796 bp. It includes an open reading frame of 1443 bp. This sequence has overall the same size as the two other mannitol transporters (1766 bp for AgMaT1 and 1781 bp for AgMaT2).

III.2. Analysis of the peptide sequence deduced from AgMaT3 cDNA

The 1443 by of the open reading frame of the AgMaT3 cDNA coded for a protein of 481 amino acids which was shorter than that coded by AgMaT1 (513 aa) and AgMaT2 (524 aa). AgMaT3 shows 82% and 73% similarity with AgMaT1 and AgMaT2, respectively. This shorter size is in fact due to a cloning artefact. In fact, by using new primers (5' primer: 5'-AGC TTC GAC CAT TGT TTC TC-3' (SEQ ID NO: 29) and 3' primer: 5'- CCG CTC GAG CAT CAC AAA GCT ATA ATC C-3') (SEQ ID NO: 30), the authors of the present invention were able to clone a novel cDNA with a longer length. The sequence corresponding to the longest protein was denoted AgMaT3; the sequence corresponding to the shortest protein was re-baptized AgMaT3'.

III.3. Analysis of Novel Nucleotide Sequence of AgMaT3 cDNA

Digital analysis of the genomic sequence of AgMaT3 showed a novel ATG (giving an open reading frame of 1572 bp, SEQ ID NO: 14). By taking this ATG as the starting point for translation (FIGS. 6 and 8), the coded protein is longer (524 aa, SEQ ID NO: 8) than that obtained by RACE PCR (481 aa). Alignment of the protein sequences AgMaT1, AgMaT2 and AgMaT3 proved that this result appears more plausible with better homogeneity regarding the length and alignment of these three sequences (FIG. 6).

III.4 Analysis of the Novel Peptide Sequence Deduced from AgMaT3 cDNA

The 1572 bp of the open reading frame of AgMaT3 cDNA codes for a protein of 524 amino acids with the same size as those coded by AgMaT2 and slightly longer than AgMaT1 (518 aa) (FIG. 7). The similarity between these three transporters is high but clouded by different protein portions (FIG. 7, non grayed spaces where the amino acids are homologous in none of the other two sequences being studied), thus indicating that these mannitol transporters are distinct and in particular in the N and C terminal ends. The 524 amino acid AgMaT3 protein has a theoretical molecular mass of 56670 Da. The isoelectric point of this protein has been estimated to be 8.3, a value close to those determined for AgMaT1 and AgMaT2 (8.3 and 8.4 respectively).

III.5. Functional Characterization of AgMaT3 Protein Heterologous Expression in Yeast Analysis of the protein sequences showed that AgMaT3 has strong homologies with the other two mannitol transporters. The cDNA of AgMaT3 and AgMaT3' were cloned separately into the shuttle vector PDR 196 then acted to complement the RS453 strain. After transformation, the yeasts possessing the AgMaT3/PDR plasmid were isolated on SC glucose medium for uracil prototrophy, the URA3 gene being carried by the plasmid.

To verify that mannitol transport was carried out by AgMaT3, the absorption kinetics of [$^3$H]-mannitol of the strain complemented by the plasmid which contained or did not contain AgMaT3 cDNA or AgMaT3' cDNA was monitored. Three independent clones were tested, corresponding to 3 transformation events with AgMaT3/PDR in the yeast. The absorption of mannitol labeled with tritium was followed as a function of time (FIG. 5). The yeasts expressing the plasmid AgMaT3/PDR absorbed much more mannitol than yeasts transformed with PDR. The absorption values at 3 minutes were very close to those noted for AgMaT1 under the same measurement conditions. This result thus indicates that AgMaT3 is a mannitol transporter. It should be noted that the results obtained during mannitol absorption by the AgMaT3'/PDR/RS453 yeasts indicate that this transporter is functional although the protein has a deletion of about forty amino acids.

III.6. Cloning of Genomic Sequence of AgMaT3

Genomic sequence cloning was carried out using the same principal as that for the promoters, with the "Universal genome walker" kit (Clontech) using primers oriented in the reverse direction to those which allowed the promoter to be sequenced. The coding sequence of AgMaT3 was spliced with two introns of 264 and 805 bp (FIG. 8). The partial genomic sequence represented 2772 bp starting from the ATG codon. The exons deduced from this genomic sequence corresponded perfectly to cDNA sequences except at the translation initiation level. Note the presence of a polyadenylation site AATAAA in position 2822 (or 179 bp after the stop codon) on the sense strand (+) of the genomic sequence of AgMaT3 (FIG. 8).

III.7. Analysis of AgMaT3 Expression in Various Tissues of Celery which has or has not Undergone Saline Stress This analysis was carried out by real time RT-PCR on various tissues (xylem, phloem, leaves, roots and parenchyma) of plants which had or had not been treated with 300 mM NaCl for three weeks, in order to study the level of expression and their stimulation in response to stress.

The values obtained with the AgMaT3 probe were normalized with the 26s celery ribosomal probe. A difference of 3.42 Ct (see ΔΔCt in Table III) between the "control" and "stressed" phloem indicates that 3.42 supplemental cycles were required to obtain the signal in the control phloem of the same intensity as in the stressed phloem; the expression of AgMaT3 was higher in phloem from plants treated with NaCl. Further, since the PCR cycles allowed exponential amplification, a difference of 3.42 Ct corresponded to $2^{3.42}$, i.e. 10.70 times more for AgMaT3 transcripts in the phloem from "stressed" plants than from "controls". This result confirms those obtained above in the subtractive library and by Northern blot (FIG. 3 and Table II). Similarly, a difference of 7.52 Ct (see ΔΔCt in Table III) between "control" and "stressed" roots indicates that 7.52 additional cycles were required to obtain a signal in the control roots of the same intensity as in the "stressed" roots.

TABLE III

Results obtained by real time RT-PCR with the AgMaT3 probe, in various tissues (phloem, xylem, parenchyma, leaves, roots) of control or NaCl-treated plants (300 mM for 3 weeks). These results have been corrected by the values for the standard 26S ribosomal probe of celery.

| Test tissue | ΔCt AgMaT3 − 26S | ΔΔCt |
|---|---|---|
| Control phloem | 19.72 | 3.42 |
| NaCl phloem | 16.31 | PhN > PhT |
| Control leaves | 19.05 | 0.58 |
| NaCl leaves | 19.63 | FN < FT |
| Control xylem | 21.88 | 3.17 |
| NaCl xylem | 18.72 | XN > XT |
| Control roots | 21.13 | 7.52 |
| NaCl roots | 13.61 | RN > RT |
| Control parenchyma | 17.50 | 1.03 |
| NaCl parenchyma | 16.47 | PaN > PaT |

Ct corresponds to the number of cycles necessary to perceive a signal of a given intensity.
ΔCt is the difference between the means of Ct (means of repetitions for a probe analyzed in a given tissue) obtained for the AgMaT3 probe after subtraction of the mean of the Cts obtained for the 26s probe.
ΔΔCt corresponds to the comparison (difference between two ΔCts) between the various tissues.
The higher the value of Ct, the more cycles were required to obtain a signal and thus the fewer transcripts in that tissue.

III.8. Conclusion for AgMaT3

The information obtained during the absorption of mannitol as a function of time and the nucleotide and protein sequence alignments allow one to conclude that AgMaT3 codes for a third mannitol transporter in stick celery. The real time RT-PCR and Northern blot studies confirm that the expression of AgMaT3 is specific to saline stress. This mannitol transporter thus could play an important role in saline stress tolerance.

IV. Investigation of Promoters and Heterologous Expression in *A Thaliana*

To investigate the specific promoters induced by saline stress in the phloem, it was desirable to be able to have available a high performance system for cloning promoters (the steps for screening a genomic library are particularly trying). Further, a first attempt to investigate the promoter for the AgMaT1 gene from a genomic library in a λ phage was without success (Cyril Maingourd, 2001). With the aim of investigating several promoters, it became necessary to use a more rapid technique. for this reason a technique for PCR amplification of promoter regions from DNA sequences (Universal genome walker kit, Clontech) was used. The investigation of promoter sequences in celery was carried out on the following selected genes: AgMaT3 coding the novel mannitol transporter and the two metallothionein genes (AgMT2 and AgMT3).

IVA. Genome Library and Cloning of Promoters

Genomic DNA from celery was separated into 4 batches on which four different restriction enzymes were caused to act, namely EcoRV, DraI, SspI and HpaI, leaving blunt ends, specific adapters having been ligated thereto. 4 different fractions were obtained on which PCR was carried out with a specific primer of the sequence to be amplified (selected close to the ATG codon for the start of translation) and a specific primer for the adapter. The fragments obtained were of variable size with a particular profile at each digestion. Only the longest amplified fragments were retained for cloning and sequencing. Several development stages were necessary to obtain this library as regards the choice of restriction enzymes (one of the enzymes recommended by the supplier not cleaving celery DNA) and the equipment used. For each gene studied, a promoter region upstream of the ATG was cloned into an intermediate vector (pDONR 207) then transferred into a binary expression vector (pBi-GUS-R1R2 and pBi-GFP-R1R2) by the Gateway system (Invitrogen). This allowed a study of the reporter genes (GUS or GFP) to be carried out under the control of the described promoters after transformation of *Arabidopsis* plants.

The constructs formed acted to transform agrobacteria. After verification of the presence of plasmids in the agrobacteria, *Arabidopsis* plants were transformed using the technique described in the Methods and Apparatus section.

IVB. Promoter of Gene Coding for the AgMaT3 Mannitol Transporter

The AgMaT3 promoter represents 589 bp upstream of the ATG (FIG. 8, SEQ ID NO: 4). The AgMaT1 and AgMaT32 promoter regions were also cloned and were 844 bp and 383 bp upstream of the ATG. These three sequences contained numerous A/T repetitions characteristic of the promoter regions.

The binding sites for the transcription factors in response to different stimuli were investigated using PLACE software (DNA.affrc.go.jp/sigscan/). Only the cis elements regulated by the sugar signal and light were analyzed. The position of the cassettes is indicated with respect to the translation initiation site (ATG codon). The regulatory proteins can bind to the sense strand denoted (+) or to its complement, the antisense strand, denoted (−).

IVB.1. Response to Light

The GATA box (Gatabox, S000039) required for regulation by light (Teakie et al, 2002) was identified 7 times in the AgMaT3 promoter (at −299 (−), −289 (−), −269 (+), −264 (+), −254 (−), −154 (+) and −77 (+)). The GT-1 binding site (GT1 CONSENSUS, S000198) (Terzaghi and Cashmore, 1995) was present 5 times upstream of AgMaT3 (−392 (−), −291 (−), −264 (+), −201 (−) and −154 (+)). The GATAA sequence (I-BOX, S000199), highly conserved upstream of the genes regulated by light in both mono and dicotyledons (Terzaghi et Cashmore, 1995), was found 3 times upstream of AgMaT3 (at −290 (−), −264 (+) and −154 (+)).

The "Tbox" (TBOXATGAPB, S000383, ACTTFG), involved in the activation of genes by light, was found in the AgMaT3 promoter at −455 (−). Transcription in response to light of the psaDb gene of tobacco depends on the element Inr ("initiator" INRNTPSADB, S000395, C/TTCANT(C/T)$_2$, present 2 times upstream of AgMaT3 (−387 (+) and −189 (−)).

IVB.2. Response to Sugars

Sugars are now considered to be molecules which are capable of regulating the expression of many genes.

The PYRIMIDINEBOXOSRAMY1A (CCTTTT, S000259) box, responding to gibberellin and also involved in the repression by sugars (Morita et al., 1998), is present in the promoter sequence of AgMaT3 two times (−398 (+) and −219 (−)). The element TATCCA (TATCCAOSAMY, S000403), the binding site of MYB proteins (Lu et al., 2002), is present once in the AgMaT3 promoter (−299 (+)). The "W-box" element (WBOXHVISO1, S000442, TGACT), the binding site of the transcription factor SUSI BA2 (sugar signalling in barley, inducible by sugar), was identified three times in the AgMaT3 promoter (−419 (−), −367 (−) and −74 (−)). These elements suggest regulation by sugars (glucose, saccharose).

IVC. Promoters of AgMT2 and 3

Metallothioneines were found to be induced in the phloem and in the case of saline stress but also in the case of attacks by greenfly and viruses (Franchon Divol, 2003). The results of the present saline stress analysis have shown that the metallothioneins AgMT2 and AgMT3 are specifically expressed in response to this stress (FIG. 3).

The promoter regions represent 1319 and 648 bp and were cloned upstream of the reporter genes (GUS and GFP) of the pBi vectors for AgMT2 and AgMT3 (FIGS. 9 and 10).

IVD. Analysis of Stress Response Cassettes

Digital analysis of the promoters revealed many potential cis elements linked to abiotic stresses.

IVD.1. Response to Abiotic Stresses

Abscissic acid (ABA) is present in all higher plants. This phytohormone is involved in several events in the development of seeds and regulates the expression of many genes in response to environmental stresses such as dehydration, salt and cold (Busk and Pages, 1998). Analysis of the promoters AgMaT3, AgMT2 and AgMT3 has brought to light the cis regulators ABRE (ABA responsive element) on which many ABFs (ABRE binding factor, members of a subfamily of bZIP proteins) bind in response to an ABA dependent signalling pathway (Kang et al, 2002) to induce expression of a large number of genes (Choi et al., 2000). In *Arabidopsis*, induction of the rd22 gene by ABA and dehydration involves the transcription factors MYC and MYB (Abe et al., 2003 and 1997) binding to specific CANNTG (MYCCONSENSUAT, S000407) or C/TAACG/TG (MYB2CONSENSUSAT, S000409), A/TAACCA (MYB1AT, S000408) sites. The CANNTG (S000407) sequence is also the ICE binding site (inducer of CBF expression) which regulates transcription of genes coding a CBF, in response to cold (Chinnusamy et al., 2003). The S000407 site is present upstream of AgMaT3 (−550 (+/−), FIGS. 8 and 11) and AgMT2 (−369 (+/−) and −158 (+/−), FIGS. 9 and 11). This site has not been identified in the AgMT3 promoter (FIGS. 10 and 11). The S000409 sequence was analyzed upstream of the AgMT2 gene at −820 (+), AgMT3 at −575 (+). S000408 is present in the AgMT2 promoter at −642. A MYB transcription factor of *Arabidopsis* induced by dehydration and saline stress (Urao et al., 1993), recognizes and binds to the consensus sequence TAACTG (MYB2AT, S000177). This has been characterized upstream of AgMT3 at −575 (+).

The CNGTTG/A (MYBCORE, S000176) sequence represents the binding site of MYB which is also induced by hydric stress in A thaliana. This sequence has been identified in the AgMT2 promoter at −820 (−) and AgMT3 promoter (−575 (−) and −563 (−)). The thermoregulated expression of a hs (heat shock) gene from soya (Rieping and Schoffl, 1992) is regulated via an HSE (heat shock element) element of the promoter, but this activity requires additional sequences: CCAAT boxes (CCAATBOX1, S000030) These are present upstream of the AgMaT3 gene (−176 (+)). This box is not present upstream of AgMT3 although it has been identified six times in the AgMT2 promoter at −1280 (−), −834 (−), −1263 (−), −693 (−), −1057 (−) and 624 (+).

IVD.2. Response to Biotic Stresses

Numerous signalling pathways in response to biotic and abiotic stresses are interlinked. The linking elements of transcription factors in response to pathogenic attack and injury were also retained as potential candidates during induction by saline stress. Some of them were enumerated when their motifs were detected on the AgMaT3, AgMT2 and AgMT3 promoters.

The expression of many defense genes is regulated by cis elements such as the GCC (GCCCORE, GCCGCC, S000430) box, identified at −284 (−) upstream of AgMaT3.

The motif AG (AGATCCAA, AGMOTI FNTMYB2, S000444) is an element which is sufficient to provide a response to injury following an eliciting treatment (Sugimoto et al., 2003). The motif S000444 has been discovered in the AgMaT3 promoter at −452.

The most important elements in response to biotic stresses are the W boxes, binding sites for WRKY proteins (transcription factor superfamily involved in the regulation of various physiological programs such as defense against a pathogen, senescence and the development of trichomas (Eulgem et al., 2000)). They are linked to palindromic TGAC sequence W boxes such as the "WB box" (WBBOXPCWRKY1, TTTGACT, S000310), present upstream of AgMaT3 at −74 (−) and AgMT2 at −169 (+).

The NPR1 gene of *Arabidopsis*, a positive regulator of inducible resistance to diseases, contains in its promoter the "W-box" (WBOXATNPR1, TTGAC, S000390) sequence, a binding site for WRKY induced by pathogenic infection or a treatment with salicylic acid (Yu et al., 2001). This has been identified three times in the AgMaT3 promoter (−418 (−), −366 (−) and −73 (−)), AgMT2 promoter at −168 (+) and AgMT3 promoter at −496. These elements were placed as a function of their position on the promoter regions of AgMaT3, AgMT2 and AgMT3 (FIG. 11).

The promoter sequence of AgMT2 comprises few MYB, MYC binding sites or sites in response to ABA but no fewer than five HSE elements on the (−) strand as well as a LTRE element. Monitoring the expression of these promoters upstream of a reporter gene in the tissues and organs of the plant during saline stress is thus important.

IVE. Functional Analysis of Promoter Regions by Heterologous Expression in *A Thaliana*

Each Sequence Identified and Cloned in Celery was Placed Upstream of Two Reporter Genes GUS and GFP to follow their expression in A thaliana. Cloning was carried out using the "Gateway" technique (Invitrogen) between the right and left edges of a pBI vector. The regions upstream of ATG which were cloned for each of the genes are shown in FIG. 12. The lengths of the cloned regions were 548 (AgMaT3), 649 (AgMT3) and 1319 base pairs (AgMT2). All of the cloned sequences included the putative transcription initiation site (located as position 541 for AgMaT3, at position 1502 for AgMT2 and at position 639 for AgMT3).

Effective transcription of plants was doubly verified by germination in the presence of kanamycin and by PCR monitoring with specific NPT-II primers. For all experiments, two controls were added: a non-transformed col10 line and plants transformed by the uiad gene under the control of the ATPP2-1 promoter (Dinant et al, 2003) which gave a strong signal in phloem. The experiments were repeated with 5 plants for each promoter construct. Plant survival was tested after treatment with NaCl at concentrations in the range 50 to 250 mM. The ideal concentration for inducing a saline stress response without being lethal for the plant nor preventing the development of a flower spike and the production of seeds was determined to be 100 mM.

The response was followed by visual inspection of the staining of leaves before and after saline stress and of the cross section to verify the color of the phloem.

General observation of the leaves of the control plants (not stressed) did not show, after GUS staining, any special coloration except in the case of ATPP2 and AgMT2. In all cases, staining was limited to the ribs. For ATPP2 and AgMT2, all of the ribs were positively colored (type I to IV, FIG. 13C) while in the case of AgMaT3 and AgMT3, only the major ribs (type I) were colored (FIGS. 13A and E). In all cases, the ribs in the petioles were also stained. Further, the young leaves and mature leaves were stained in an identical manner.

To determine the exact location of GUS expression in the vascular bundles, cross sections were made through frozen material. For the plants showing a strong staining (ATPP2-1 and AgMT2, FIG. 13D), the blue staining was evident in the cells of the phloem but also occasionally in the surrounding cells. This may be due to diffusion of the staining because it has already been shown that GUS staining is limited to phloem cells in the case of ATPP2-1 (Dinant et al, 2003). For the AgMaT3 (FIG. 13B) and AgMT3 (FIG. 13F) constructs, the coloration was also evident in the phloem cells, thus confirming the initial identification of the corresponding cDNA as specific to the phloem cells. Staining is also detected in the parenchymal xylem cells. Among these cells are most probably vessel associated cells (VAC) which are considered to be very similar as regards function to comparable cells of the phloem (Fromard et al, 1995).

Induction by saline stress may be either specific to the present test or form part of a response of the plant to stress of a more general order. To test this hypothesis, groups of 5 plants from the same transformants were subjected to an osmotic stress (absence of watering for 4 days), a cold stress (4 days at 4° C.), a heat stress (4 days at 30° C.) and to an injury stress (leaves pinched with tweezers 3 times, taking care to avoid the major ribs). The plants were harvested the day after the stress. A group of 5 independent plants was used as the control. The plants were stained as for the saline stress.

All of the plants (except for the hydric and saline stress) were watered twice a day with 10 ml of fawcet water or a solution of fertilizer (once during the stress period). The leaves (completely mature or young shoots) were sampled at the end of the stress period and used for histochemical GUS staining (Jefferson et al, 1987). Other groups of leaves were frozen in liquid nitrogen and stored at −80° C. prior to the fluorimetric GUS tests (Jefferson et al, 1987).

For the AgMT2 plants, it was difficult to observe a difference between the various stresses because the staining was already particularly intense in the control plants. However, no difference was observed in the staining profile. In the case of AgMaT3, all of the stress forms produced similar staining profiles with the exception of hydric stress and stress by injury where no signal was detected although the plants were still in good health. In AgMT3 plants, GUS staining was evident in all stress forms with the exception of stress by injury.

The responses to stress by injury would use a different signaling pathway and would not lead to activation of the genes being studied.

The results are very similar to those obtained with celery. Both the 5' region of AgMT3 and that of AgMaT3 led to expression of the reporter gene in the phloem (and to a certain extent also in the xylem) but only in the stressed plants and not in the control plants. In the case of AgMT2, a large amount of expression was observed in the phloem of transformed *Arabidopsis* plants, even under the control conditions. An interesting point is the high degree of expression of fusion between the AgMT2 promoter and GUS in *Arabidopsis* in all of the ribs of the leaf (FIG. 13C) which indicates that the expression profile is specific to phloem.

Example 3

Transformation of *Brassica*

*Brassica* transformation protocol: based on Brasileiro et al 1992 and Bethomieu (doctoral thesis: Producing transgenic cabbages tolerant to noctuids by genetic transformation with a gene coding for an endotoxin of *Bacillus thuringiensis*).

1. Seeding and Germination

Seeds were disinfected for 25 minutes with agitation in a solution of bayrochlore (3 pellets/liter of demineralised water) before being rinsed with sterile water and dried over blotting paper. Thus sterilized, they were sown into tubes on M1 germination medium (4.4 g/l of MS5519 (Sigma), 20 g/l of sacchraose and 8 g/l of agar agar (pH 5.8). The seeds were cultivated for 15 days at 20° C. (16 h photoperiod) to obtain plantlets at the 2-3 leaf stage.

2. Culture of Bacteria 2 agrobacteria were used: C 58 pMP90 contained the pSCV plasmid with T-DNA comprising the expression cassette of the reporter gene (GUS gene), under the control of the promoter sequences of the present invention (selection: kanamycin: 50 µg/ml; Rifampicin: 20 µg/ml), the second containing tumorigenic t-DNA (pT182-139) (selection: kanamycin: 50 µg/ml; rifampicin: 50 µg/ml and gentamycin: 20 µg/ml).

The bacteria were pre-cultivated in 20 ml of LB medium (Luria Bertani from Difco) containing selection antibiotics plus 1 ml of glycerol bacterial stock. These pre-cultures were agitated (200 rpm) at 28° C. for 24 h. The cultures were carried out by adding 1 ml of pre-culture to 20 ml of LB medium containing the selection antibiotics. The cultures were agitated (200 rpm) at 28° C. overnight.

3. Preparation of Bacteria

If the optical density at 600 nm of the 2 agrobacteria cultures after one night was not 1, they were centrifuged for 10 min at 4000 rpm. The bacterial residue was taken up with a sufficient volume of M4 liquid medium containing 0.88 g/l of MS 5519 and 10 g/l of saccharose (pH 5.8) to attain the desired OD. The 2 bacteria were mixed in a bact2/bact1 ratio of 1:1/6.

4. Inoculation of Plants and Planting Out

The plantlets were inoculated using DEMARTEL 20 cm gripping tweezers dipped in the bacteria mixture and used to injure the stem at three different points above the cotyledons. The inoculated plantlets were cultivated at a temperature of 20° C. (photoperiod 16 h) until tumors appeared at the injury points. The tumors were planted out on a M2 medium containing 4.4 g/l of MS5519, 30 g/l of saccharose, 8 g/l of agar-agar, 400 mg/l of antibiotic (Augmentin) (pH 5.8).

5. Bud Regeneration

About 1 month after planting out the tumors, the buds appeared. When they were about 3 to 4 cm in size, they were isolated and placed in tubes on a M3 medium containing 4.4 g/l of MS5519, 30 g/l of saccharose, 8 g/l of agar agar (pH 5.8) and 200 mg/l of antibiotic (Augmentin) (pH 5.8).

The tumors were fragmented and planted out on M2 medium to regenerate other buds. The plantlets had rooted 3 to 4 weeks after isolating the buds on M3 medium.

6. Acclimatization of Plants

The plantlets were transferred into plugs of earth and maintained at 22° C. and 80% relative humidity for one week. They were then treated as plants from sown seeds (temperature 20° C. and ambient hygrometry), repotted in culturing pots for the production of seeds. The siliques matured at 5 months.

Example 4

Tomato Transformation

Tomato Transformation Protocol (Binary Transformation System)

Derived from Filatti et al, 1987.

1. Sowing and Germination

Seeds placed in a square of mosquito netting and closed with staples were disinfected in a solution of bayrochlore (2 or 3 pellets per liter of distilled water and a few drops of Tween) for 20 minutes. They were then rinsed three times over 15 minutes in sterile distilled water then rapidly dried on blotting paper. The sterilized seeds were sown into bottles on T1 germination medium (MS 6899, Sigma) comprising 2.2 g/l of MS 6899, 2 ml.l of Nitsh and Nitsh vitamins, 1965, 30 g/l of saccharose (pH 5.9, adjusted with KOH) and 8 g/l of agar agar. The dishes were left in the dark for 24 hours in an oven at 26° C. When placed in the light, the cotyledons developed. They could be used 7 to 8 days after sowing.

2. Preculture of Explants on Solid TT2

One explant was cut per cotyledon and then placed on T2 preculture medium comprising 4.4 g/l of MS 6899, 2 ml/l of Nitsh and Nisch vitamins, 0.9 mg/l of thiamine, 200 mg of potassium dihydrogen phosphate ($KH_2PO_4$), 30 g/l of saccharose (pH 5.9, adjusted with KOH), 8 g/l of agar agar, 0.2 mg/l of 2,4-D (Sigma), 0.1 mg/l of kinetin (Sigma), 200 µmol/l of acetosyringone (Aldrich). The lower face of the explants was placed against the medium. The dishes were left in the light at 26° C. for 24 h.

3. Preparation of Bacteria

EHA 105 *agrobacterium* containing the plasmid pBI101 with the T-DNA comprising the expression cassette of the selection gene (kanamycin resistance gene) and the reporter gene (GUS gene of beta-glucuronidase, under the control of the promoter sequences of the present invention (kanamycin antibiotic: 50 µg/ml; rifampicin: 50 µg/ml).

Bacterial pre-culture was carried out in a 50 ml Falcon tube by seeding 1 ml of glycerol bacterial stock into 10 ml of culture medium of LB or TP (yeast tryptone from Difco) containing the selection antibiotics. These pre-cultures were agitated (250 rpm) in the dark at 28° C. for 24 h. The cultures were carried out by adding 1 ml of the pre-culture to 20 ml of LB or YT medium containing the selection antibiotics. The cultures were agitated (250 rpm) in the dark at 28° C. overnight. The next morning, the OD at 600 nm of one ml of bacterial culture was measured. If it was not 2, the cultures were centrifuged for 10 minutes at 3000 rpm. The supernatant was eliminated and the bacterial residue was resuspended with a suitable volume of liquid T2 medium.

4. Co-Culture 2.5 ml of bacterial solution at the $OD_{600\ nm}$ of 2 was added to 28.5 ml of co-culture medium (T2 liquid medium with only acetosyringone, no kinetin, nor 2,4-D) per Petri dish.

The explants were removed from the pre-culture medium and added to the Petri dishes to incubate with the bacteria for 30 minutes. The explants were then dried on sterile blotting paper and replaced on the same solid T2 medium which was used for pre-culture. The dishes were placed in the dark at 26° C. for 48 h.

5. Washing of Explants

About 150 ml of MS 6899 liquid washing medium was placed in each sterile pot (disposable) and a maximum of 50 explants were immersed therein (T3 medium: 4.4 g/l of MS 6899, 2 ml/l of Nitsh and Nitsh vitamins, 30 g/l of saccharose and 400 mg/l of Augmentin (pH 5.9 adjusted with KOH). After about ten minutes immersion, the explants were recovered using tweezers and dried rapidly on sterile blotting paper.

6. Planting Out of Explants into Regeneration Medium

The explants were planted out onto solid T3 medium cast into deep Petri dishes. Solid T3 medium: 4.4 g/l of MS 6899, 2 ml/l of Nitsh and Nitsh vitamins, 30 g/l of saccharose, 8 g/l of agar agar, 2 mg/l of zeatin (Sigma), 500 mg/l of augmentin (600 mg/l when using the LBA4404 bacteria), 100 mg/l of kanamycin (Sigma). After 2 weeks in the light at 26° C., the explants were cut into two to differentiate the transformation events (the two ends of an explant are considered to be distinct and planted out into fresh T3 medium. The number of explants which had regenerated 21 days after co culture was counted.

7. Preparation of Development Medium

The buds were separated from the primary explant 4 to 6 weeks after co culture and placed on T4 selective medium (2.2 g/l of MS 6899, 2 ml/l of Nitsh and Nitsh vitamins, 20 g/l of saccharose, 8 g/l of agar agar, 0.5 mg/l of zeatin (Sigma), 300 mg/l of augmentin (600 mg/l when the LBA4404 bacterium was used), 50 mg/l of kanamycin (Sigma)

8. Rooting of Transformed Buds

When the buds reached a few centimeters in height, they were planted out into large TPS pots on T5 rooting medium (2.2 g/l of MS 6899, 2 ml/l of Nitsh and Nitsh vitamins, 20 g/l of saccharose, 2.5 g/l of phytagel, 0.5 mg/l of AIA (Sigma), 300 mg/l of augmentin (600 mg/l when the LBA4404 bacterium was used), 50 mg/l of kanamycin (Sigma). Plantlets synthesizing chlorophyll and developing roots were considered to have transformed. After determining the degree of ploidy on each plantlet by flow cytometry or counting amyloplasts, the diploid plantlets were acclimatized by planting in a greenhouse.

9. Acclimatization—Greenhouse Planting

Well developed plantlets were rooted in 10 cm cells on Steckmedium (planting out medium). They were covered for two weeks with a plastic sheet to maintain a high degree of hygrometry. The plantlets were then planted into 7 liter pots filled with Pouzzolane.

Development of Saline Stress Protocol

Non transgenic tomato seeds (Kemer) were sown under conventional germination conditions: 10 seeds per plastic dish with blotting paper soaked in water supplemented with different concentrations of NaCl ($H_2O$, 50, 100, 150, 200, 250 and 300 mM) using two dishes per concentration.

The seeds were kept in the dark for 3 days then exposed to light at a temperature of 25° C. Observations were made 5 to 6 days following germination.

The $H_2O$ control exhibited 90% germination, and the plantlets (cotyledon stage) measured about 2 cm. Seeds which had received 50 mM of NaCl exhibited 45% germination and the plantlet size was 1 cm. Seeds which had received 100 mM of NaCl and above had not germinated at the time of the observation and had not germinated 2 weeks later.

A dose of 50 mM of NaCl was used to produce saline stress.

GUS Test Protocol

1. Preparation of Reaction Buffer

A solution a of 0.2 M $Na_2HPO_4$ (Merck no 238), 28.4 g/l, was gradually mixed with a solution B of 0.2 M $NaH_2PO_4$ (Merck no 6), 24 g/l, until a pH of 7 was reached. 5 mg of X glucuronide (Clontech) was dissolved in 50 µl of dimethylformamide and 5 ml of 0.2 M $NaPO_4$, pH4, was added (solution A+B) to obtain the reaction buffer.

2. Carrying Out the Test

200 μl of reaction buffer was deposited in the walls of an Elisa plate (96 wells) or 700 μl in a 24 well plate. Fragments of tissues (stems, leaves etc) which had been very finely cut with a scalpel were then added. The plate was incubated in an oven at 37° C. for approximately 18 hours. The appearance of a blue coloration revealed activity of the GUS enzyme. A few rinses with 95° alcohol could be carried out to decolorize the tissue fragments to facilitate reading (optional).

The intensity of the blue stain was recorded using the following scale:

| 0 | zero |
| 1 | + |
| 2 | ++ |
| 3 | +++ |

Protocol for Preparing Tissue Sections for Plants Transformed with the Construct pAgMT2-GUS-tNOS Positive GUS stems were placed vertically in a 6% agar plug; the plug was then stuck to the platen of a vibratom (electronic device provided with a razor blade which can make fine 1 μm cuts) to obtain the 40 μm sections used in our study.

These sections were recovered from the blade in a drop of a water/glycerol, 50/50 mixture; they were then observed between the slide and cover under an optical microscope (LEICA).

Results

Tomato plants (*solanum lycopersicum*) of the KEMER genotype were transformed using the protocol described above with EHA 105 *agrobacterium* containing the pBI101 plasmid with the T-DNA comprising the pAgMat3-GUS-tNos or pAgMT2-GUS-tNos construct. Ten to twenty independent transformation events were obtained for each construct (To plants).

PCR tests were carried out on T0 plants using primers amplifying a sequence straddling between the promoter of interest and the GUS gene in order to check whether the plants had effectively been transformed and included the construct.

Positive To PCR plants were repotted and their seeds were harvested (T1 seeds) and sown onto growth medium supplemented with kanamycin (100 mg/ml) to produce T1 plants. A PCR analysis and segregation and KHI2 tests were carried out on the tomato plants to conserve only T1 plants exhibiting a 3:1 segregation (KHI2 less than 5, indicating mono-insertion). 6 T1 plants per event were repotted for observation of the expression of the study promoters (GUS tests).

1. Saline Stress and GUS Test on Plants Transformed with the pAgMat3-GUS-tNOS Construct 1) Transformation with the Construct pAqMat3-tNOS PCR analyses were carried out using the following primers:

```
Promoter primer:                              (SEQ ID 36)
5'-GGGGACAAGTTTGTACAAAAAAGCAGGCTGAACAGAAACAATTGTG
GATG-3'

GUS primer:                                   (SEQ ID 37)
5'-CGATCCAGACTGAATGCCC-3'
```

The transformation events for which the PCR test was positive and the T1 plants with a 3:1 segregation (KHI2 less than 5) are shown in Table 4.

TABLE IV transformation events with the PCR positive pAgMat3-GUS-tNOS construct and exhibiting a test KHI2 of <5

| Construct | Transformation event | PCR promoter/GUS confirmation | KHI2 | Number of acclimatized plants |
|---|---|---|---|---|
| pAgMat3-GUS-tNOS | 1T-LE-KE-010-5b | + | 0 | 10 |
| pAgMat3-GUS-tNOS | 1T-LE-KE-010-8a | + | 0 | 6 |
| pAgMat3-GUS-tNOS | 1T-LE-KE-010-10b | + | 0 | 10 |
| pAgMat3-GUS-tNOS | 1T-LE-KE-010-11a | + | 0 | 5 |
| pAgMat3-GUS-tNOS | 1T-LE-KE-010-4a | + | 1 | 10 |
| pAgMat3-GUS-tNOS | 1T-LE-KE-010-10a | + | 1 | 7 |
| pAgMat3-GUS-tNOS | 1T-LE-KE-010-11a | + | 1 | 2 |
| pAgMat3-GUS-tNOS | 1T-LE-KE-010-27a | + | 1 | 4 |
| pAgMat3-GUS-tNOS | 1T-LE-KE-010-28a | + | 0 | 8 |
| pAgMat3-GUS-tNOS | 1T-LE-KE-010-29b | + | 0 | 10 |
| pAgMat3-GUS-tNOS | 1T-LE-KE-010-51a | + | 0 | 10 |

2) Saline Stress and GUS Test

The T1 plants obtained were watered with water containing 50 mM of NaCl twice a day, with 10 ml at each watering, for 4 days. The fifth day, tissue samples were taken and the GUS tests were carried out. Two controls were also used: a positive GUS control under the control of a constitutive promoter and a non-transformed KEMER plant control.

Eleven independent transformation events (KHI2 test of less than 5, indicating mono insertion) and 2 controls (non-transformed and positive GUS) were analyzed. When sufficient plants were available, 6 T1 plants per transformation event were repotted and used for the GUS tests: 4 which had undergone a saline stress (S) and 2 watered with clear water (NS). If there were fewer than 6 plants, all available plants were used.

The GUS test was carried out separately on root and leaf fragments. Reading was carried out 3 days after the test (see plates in FIG. 14).

The transformed plants had a blue coloration at the roots. Preferential expression of GUS in the root tissue indicates an activity of the AgMaT3 promoter in this tissue. The test results are shown in table 5 below.

TABLE V

GUS test on plants transformed with the pAgMat3-GUS-tNOS construct and subjected or not subjected to saline stress.

| Transformation event | Plant number | Stress/ no stress (S/NS) | 4 days 50 mM GUS test roots | 4 days 50 mM GUS test leaves |
|---|---|---|---|---|
| 1T-LE-KE-010-5b | 37 | S | 1 | 1 |
|  | 38 | S | 1 | 1 |
|  | 39 | S | 3 | 0 |
|  | 40 | S | 1 | 0 |
|  | 41 | NS | 3 | 1 |
|  | 42 | NS | 2 | 1 |

TABLE V-continued

GUS test on plants transformed with the pAgMat3-GUS-tNOS construct and subjected or not subjected to saline stress.

| Transformation event | Plant number | Stress/ no stress (S/NS) | 4 days 50 mM GUS test roots | 4 days 50 mM GUS test leaves |
|---|---|---|---|---|
| 1T-LE-KE-010-8a | 44 | S | 1 | 1 |
| | 45 | S | 3 | 0 |
| | 46 | S | 1 | 0 |
| | 47 | S | 3 | 0 |
| | 48 | NS | 3 | 0 |
| 1T-LE-KE-010-10b | 49 | S | 1 | 0 |
| | 50 | S | 1 | 0 |
| | 51 | S | 1 | 0 |
| | 52 | S | 1 | 0 |
| | 53 | NS | 3 | 0 |
| | 54 | NS | 3 | 0 |
| 1T-LE-KE-010-11a | 55 | S | 3 | 0 |
| | 56 | S | 3 | 0 |
| | 57 | S | 0 | 0 |
| | 58 | S | 1 | 0 |
| | 59 | NS | 0 | 1 |
| 2T-LE-KE-010-4a | 60 | S | 2 | 0 |
| | 61 | S | 1 | 0 |
| | 62 | S | 3 | 0 |
| | 63 | S | 0 | 0 |
| | 64 | NS | 0 | 0 |
| | 65 | NS | 0 | 0 |
| 2T-LE-KE-010-10a | 66 | S | 2 | 0 |
| | 67 | S | 1 | 0 |
| | 68 | S | 3 | 0 |
| | 69 | S | 1 | 0 |
| | 70 | NS | 1 | 0 |
| | 71 | NS | 1 | 1 |
| 2T-LE-KE-010-11a | 72 | S | 3 | 0 |
| | 73 | NS | 3 | 0 |
| 2T-LE-KE-010-27a | 75 | S | 1 | 0 |
| | 76 | S | 1 | 0 |
| | 77 | S | 3 | 0 |
| | 78 | NS | 3 | 0 |
| 2T-LE-KE-010-28a | 79 | S | 3 | 1 |
| | 80 | S | 3 | 0 |
| | 81 | S | 3 | 0 |
| | 82 | S | 3 | 0 |
| | 83 | NS | 3 | 0 |
| | 84 | NS | 3 | 0 |
| 2T-LE-KE-010-29b | 85 | S | 3 | 0 |
| | 86 | S | 3 | 0 |
| | 87 | S | 3 | 0 |
| | 88 | S | 0 | 0 |
| | 89 | NS | 2 | 0 |
| | 90 | NS | 2 | 0 |
| 2T-LE-KE-010-51a | 91 | S | 2 | 0 |
| | 92 | S | 2 | 0 |
| | 93 | s | 3 | 0 |
| | 94 | S | 2 | 0 |
| | 95 | NS | 1 | 0 |
| | 96 | NS | 1 | 0 |
| KEMER NT | 187 | S | 0 | 0 |
| | 188 | S | 0 | 0 |
| | 189 | NS | 0 | 0 |
| | 190 | NS | 0 | 0 |
| GUS + control | 193 | NS | 3 | 3 |
| | 194 | NS | 3 | 3 |

These data indicate a specific root expression of the AgMaT3 promoter.

II. GUS Test on Plants Transformed with the pAgMT2-GUS-tNOS Construct

1) Transformation with the pAgMT2-GUS-tNOS Construct

PCR analysis was carried out using the following primers:

```
Promoter primer:                          (SEQ ID 38)
5'-GGGGACAAGTTTGTACAAAAAAGCAGGCTGACCCACTATCAACAATG
ATC-3'

GUS primer:                               (SEQ ID 37)
5'-CGATCCAGACTGAATGCCC-3'
```

The transformation events for which the PCR test was positive and the T1 plants with a 3:1 segregation (KHI2 less than 5) are shown in Table 6.

TABLE V transformation events with the PCR positive pAgMT2-GUS-tNOS construct and exhibiting a test KHI2 of <5

| Construct | Transformation event | PCR promoter/GUS confirmation | KHI2 | Number of acclimatized plants |
|---|---|---|---|---|
| pAgMT2-GUS-tNOS | 1T-LE-KE-008-11a | + | 1 | 6 |
| pAgMT2-GUS-tNOS | 1T-LE-KE-008-16a | + | 2 | 10 |
| pAgMT2-GUS-tNOS | 1T-LE-KE-008-20a | + | 1 | 10 |
| pAgMT2-GUS-tNOS | 1T-LE-KE-008-23a | + | 0 | 9 |
| pAgMT2-GUS-tNOS | 1T-LE-KE-008-33b | + | 1 | 4 |
| pAgMT2-GUS-tNOS | 1T-LE-KE-008-40a | + | 0 | 6 |
| pAgMT2-GUS-tNOS | 1T-LE-KE-008-59a | + | 5 | 4 |
| pAgMT2-GUS-tNOS | 1T-LE-KE-008-64a | + | 0 | 6 |
| pAgMT2-GUS-tNOS | 1T-LE-KE-008-96a | + | 0 | 10 |
| pAgMT2-GUS-tNOS | 1T-LE-KE-008-103a | + | 4 | 10 |

2) GUS Test

Eleven independent transformation events (KHI2 test of less than 5, indicating mono insertion) and 2 controls (non-transformed and positive GUS) were analyzed. 6 T1 plants per transformation event were repotted and used for the GUS tests.

The GUS test was carried out on root and leaf fragments. (plate example: FIG. 15).

The test results are shown in Table 7 below.

TABLE VII

GUS test on plants transformed with the pAgMT2-GUS-tNOS PCR construct and subjected or not subjected to saline stress.

| Transformation event | Plant number (T1) | GUS tests on stems |
|---|---|---|
| 1T-LE-KE-008-5a | 1 | 0 |
| | 2 | 0 |
| | 3 | 0 |
| | 4 | 0 |
| | 5 | 0 |
| | 6 | 0 |
| 1T-LE-KE-008-11a | 7 | 1 |
| | 8 | 0 |
| | 9 | 0 |

TABLE VII-continued

GUS test on plants transformed with the pAgMT2-GUS-tNOS PCR construct and subjected or not subjected to saline stress.

| Transformation event | Plant number (T1) | GUS tests on stems |
|---|---|---|
|  | 10 | 0 |
|  | 11 | 0 |
|  | 12 | 1 |
| 1T-LE-KE-008-16a | 13 | 1 |
|  | 14 | 1 |
|  | 15 | 0 |
|  | 16 | 0 |
|  | 17 | 1 |
|  | 18 | 1 |
| 1T-LE-KE-008-20a | 19 | 0 |
|  | 20 | 0 |
|  | 21 | 0 |
|  | 22 | 0 |
|  | 23 | 0 |
|  | 24 | 0 |
| 3T-LE-KE-008-23a | 97 | 2 |
|  | 98 | 1 |
|  | 99 | 1 |
|  | 100 | 1 |
|  | 101 | 2 |
|  | 102 | 1 |
| 3T-LE-KE-008-33b | 103 | 2 |
|  | 104 | 2 |
|  | 105 | 2 |
|  | 106 | 3 |
| 3T-LE-KE-008-40a | 107 | 1 |
|  | 108 | 0 |
|  | 109 | 0 |
|  | 110 | 0 |
|  | 111 | 0 |
|  | 112 | 0 |
| 3T-LE-KE-008-59a | 113 | 1 |
|  | 114 | 0 |
|  | 115 | 0 |
|  | 116 | 0 |
| 3T-LE-KE-008-64a | 117 | 2 |
|  | 118 | 1 |
|  | 119 | 0 |
|  | 120 | 1 |
|  | 121 | 1 |
|  | 122 | 0 |
| 3T-LE-KE-008-96a | 123 | 1 |
|  | 124 | 0 |
|  | 125 | 0 |
|  | 126 | 0 |
|  | 127 | 0 |
|  | 128 | 0 |
| 3T-LE-KE-008-103a | 129 | 0 |
|  | 130 | 0 |
| KEMER NT | 131 | 0 |
|  | 132 | 0 |
|  | 133 | 0 |
|  | 134 | 0 |
| KEMER NT | 187 | 0 |
| GUS + control | 193 | 3 |

Positive GUS fragments were then used for a histocytological analysis and observing the coloration in vascular tissues. Readings were taken 4 days after the test. The first observations showed a rather concentrated blue coloration in the vascular tissues of the stem, in some cases solely in the leaf ribs (FIG. 16).

3) Tissue Sections

FIG. 17 shows the tissue sections of plants 13(a) and 103 at the leaf (b) and the stem c). These cytological data indicate expression in the phloem tissues. These data indicate specific phloem expression of the AgMT2 promoter.

The SEQ ID sequences identified in the present application are as follows:

SEQ ID NO: 1: promoter sequence of the AgMaT3 gene of *Apium graveolens*;
SEQ ID NO: 2: promoter sequence of the AgMT2 gene of *Apium graveolens*;
SEQ ID NO: 3: promoter sequence of the AgMT3 gene of *Apium graveolens*;
SEQ ID NO: 4: complete 5' sequence AgMaT3 gene of *Apium graveolens*;
SEQ ID NO: 5: complete 5' sequence of AgMT2 gene of *Apium graveolens*;
SEQ ID NO: 6: complete 5' sequence of AgMT3 gene of *Apium graveolens*;
SEQ ID NO: 7: complete sequence of AgMaT3 gene;
SEQ ID NO: 8: putative AgMaT3 gene deduced from corresponding DNA sequence;
SEQ ID NO: 9: complete sequence of AgMT2 gene;
SEQ ID NO: 10: putative AgMT2 protein deduced from corresponding DNA sequence;
SEQ ID NO: 11: complete sequence of AgMT3 gene;
SEQ ID NO: 12: putative AgMT3 protein deduced from corresponding DNA sequence;
SEQ ID NO: 13: sequence of AgMaT3 gene without promoter portion;
SEQ ID NO: 14: cDNA coding for AgMaT3 protein (SEQ ID NO: 8).

REFERENCES

Abe H., et al., 2003. Plant Cell 15: 63-78.
Abe H., et al., 1997. Plant Cell 9: 1859-1868.
Bearden J. C., 1978. Biochem. Biophys. Acta 533: 525-529.
Bohnert H. J., et al., 2001. Plant Physiol. Biochem. 39: 295-311.
Brasileiro A. C. M., et al., 1992. Transgenic Res 1: 133-141
Busk P. K. and Pages M., 1998. Plant Mol. Biol. 37: 425-435.
Chatthai M., et al., 1997. Plant Mol. Biol. 34: 243-254.
Chevalier C, et al., 1995. Plant Mol. Biol. 28: 473-485.
Chinnusamy V., et al., 2003. Genes Dev. 17: 1043-1054.
Choi H., et al., 2000. Biol. Chem. 275: 1723-1730.
Choi D., et al., 1996. Plant Physiol. 112: 353-359.
Clough S F and Bent A F, 1998, Plant J., 16: 735-743
De Pascale S., et al., 2003. J. Amer. Soc. Hort. Sci. 128: 136-143.
Dinant S., Clark A. M., Zhu Y., Vilaine F., Palauqui J.-C, Kusiak C. and Thompson G. A., 2003. Plant Physiol. 131: 114-128.
Divol F., 2004. Biology Thesis, Plant Sciences faculty, University of Paris Xl.
Dohmen R. J., et al., 1991. Yeast 1: 691-692.
Eulgem T., et al., 2000. Trends Plant Sci. 5: 199-206.
Filatti J. J., et al., 1987. Bio/Technology 5: 726-730.
Fromard L., et al., 1995. Plant Physiol. 108: 913-918
Hasegawa P. M., et al., 2000 a. Trends Plant Sci. 5: 317-319.
Hasegawa P. M., et al., 2000 b. Annu. Rev. Plant Physiol. Plant Mol. Biol. 51: 463-499.
Higo K., et al., 1999. Nucleic Acids Res. 27: 297-300.
Hsieh H.-M., et al., 1995. Plant Mol. Biol. 28: 381-389.
Jefferson R. A., et al., 1987. EMBO J. 6: 3901-3907.
Kang J. Y., et al., 2002. Plant Cell 14: 343-357.
Karakas B., et al., 1997. Plant Cell Environ. 20: 609-616.
Kay R., et al., 1987. Science 236: 1299-1302.
Koncz C and Schell J. 1986 Mol. Gen. Genet. 204
Koyama M. L., et al., 2001. Plant Physiol. 125: 406-422.
Kreps J. A., et al., 2002. Plant Physiol. 130: 2129-2141.
Lohaus G., et al., 2000. J. Exp. Bot. 51: 1721-1732.
Lu C. A., et al., 2002. Plant Cell 14: 1963-1980.

Maingourd C, 2001. DEA Interactions Cellulaires et Transports Membranaires, University of Poitiers.
Masmoudi K., et al., 2001. Plant Physiol. Biochem. 39: 971-979.
Morita A., et al., 1998. FEBS Lett. 423: 81-85.
Nelson D. E., et al., 1999. Plant Physiol. 119: 165-172.
Noiraud N., 1999. Thesis, Plant Physiology and Biochemistry, University of Poitiers.
Noiraud N., Delrot S. and Lemoine R., 2000. Plant Physiol. 122: 1447-1455.
Noiraud N., Maurousset L. and Lemoine R., 2001 a. Plant Cell 13: 695-705.
Noiraud N., Maurousset L. and Lemoine R., 2001 b. Plant Physiol. Biochem. 39: 717-728.
Popova O. V., et al., 2003. Plant Mol. Biol. 52: 569-578.
Reid S J. et Ross G. S., 1997. Physiol. Plant. 100: 183-189.
Rieping M. et Schoffl F., 1992. Mol. Gen. Genet. 231: 226-232.
Ruiz-Medrano R., Xoconostle-Cázares B. et Lucas W J., 2001. Curr. Opin. Plant Biol. 4: 202-209.
Salekdeh G. H., et al., 2002. Field Crops Res. 76: 199-219.
Sambrook J., et al., 1989. Molecular cloning: A laboratory manual. Cold Spring Harbor laboratory (Eds), Cold Spring Harbor, N.Y.
Sauer N. and Stadler R., 1993. Plant J. 4: 601-610.
Shen B., et al., 1997 a. Plant Physiol. 113: 1177-1183.
Shen B., et al., 1997 b. Plant Physiol. 115: 527-532.
Sugimoto K., et al., 2003. Plant J. 36: 550-564.
Tarczynski M. C., et al., 1993. Science 259: 508-510.
Teakle G. R., et al., 2002. *Arabidopsis thaliana* GATA factors: organisation, expression and DNA-binding characteristics. Plant Mol. Biol. 50: 43-57.
Terzaghi W. B. et Cashmore A. R., 1995. Annu. Rev. Plant Physiol. Plant Mol. Biol. 46: 445-474.
Urao T., et al., 1993. Plant Cell 5: 1529-1539.
Vilaine F., Palauqui J.-C, Amselem J., Kusiak C, Lemoine R. and Dinant S., 2003. Plant J. 36: 67-81.
Wagner H J., et al., 2001. Transplantation 72: 1012-1019.
Yu D., Chen C. et Chen Z., 2001. Plant Cell 13: 1527-1540.

The invention claimed is:

1. An isolated nucleic acid sequence comprising the sequence SEQ ID NO:1, wherein:
said nucleic acid sequence has transcriptional promoter activity.

2. The sequence according to claim 1, having transcriptional promoter activity in plant cells.

3. The sequence according to claim 2, wherein said transcriptional promoter activity is induced by a biotic or abiotic stress.

4. The sequence according to claim 2, wherein said sequence has specific transcriptional promoter activity in the roots.

5. The sequence according to claim 2, having transcriptional promoter activity in cells of celery (*Apium graveolens* L), *Arabidopsis thaliana* or tomato (*Solanum iycopersicum* L).

6. The sequence according to claim 1, comprising or consisting of a sequence selected from sequences SEQ ID NO: 1 or 4.

7. The nucleic acid sequence according to claim 1, wherein said sequence is double stranded DNA or single stranded DNA.

8. A nucleic acid sequence fully complementary to the sequence in accordance with claim 1.

9. A DNA construct consisting of or comprising the promoter sequence according to claim 1, and a downstream sequence of interest to be transcribed, wherein transcription of said sequence to be transcribed is under the control of the promoter sequence.

10. The construct according to claim 9, wherein said promoter sequence is heterologous with respect to the sequence of interest to be transcribed.

11. A plant cell transformed by the construct according to claim 10.

12. The cell according to claim 11, wherein said DNA construct is integrated into the genome of the cell.

13. A transgenic plant comprising in its genome the sequence according to claim 1 which is exogenous with respect to the plant.

14. The plant according to claim 13, wherein said sequence is stably inserted into the nuclear genome.

15. The plant according to claim 13, in which said sequence is inserted into the mitochondrial or chloroplastic genome.

16. A transgenic plant comprising the plant cell according to claim 11, or a portion of such a plant, said portion being transgenic.

17. The plant according to claim 13, wherein said plant is a monocotyledon.

18. The plant according to claim 13, wherein said plant is a dicotyledon.

19. The plant according to claim 13, wherein said plant is a plant from the cucurbitaceae, chenopodiaceae, crucifereae, poaceae, legumineae, apiaceae, rosaceae, valerianaceae, solanaceae or asteraceae family.

20. The plant according to claim 14, wherein said plant is a tomato plant, a melon plant or a lettuce.

21. A method for preparing a transgenic plant, comprising:
    a) obtaining the construct in accordance with claim 9;
    b) introducing the construct into a cell obtained from a plant of interest;
    c) regenerating a transgenic plant and
    d) optionally, proliferating the plant to obtain descendants.

22. A transgenic plant comprising in its genome a nucleic acid sequence comprising SEQ ID NO:1; wherein
    said sequence has transcriptional promoter activity; and
    said sequence is in functional association with a heterologous coding sequence expressing said coding sequence in a specific manner in the roots.

23. A transgenic plant comprising in its genome a nucleic acid sequence comprising all or a portion of SEQ ID NO: 1, wherein:
    said sequence has transcriptional promoter activity; and
    said sequence is in functional association with a heterologous coding sequence expressing said coding sequence in a specific manner in the phloem.

* * * * *

```
                          SEQUENCE LISTING

<160> NUMBER OF SEQ ID NOS: 38

<210> SEQ ID NO 1
<211> LENGTH: 548
<212> TYPE: DNA
<213> ORGANISM: Apium graveolens

<400> SEQUENCE: 1
aagaaatttt gaacagaaac aattgtggat gcacctctct atatatttgt acttttgcat        60
actgtcgtat atatagtaaa gaattactta ataggggtga atgtactcac cgggcaaagt       120
attagtaatt tcttcattaa aatatttaag agtcaattta atttgccact gccttttctt       180
tttcagttct tacttcaagg ttagtcaatc tattccggtg aataattacg aacgaatata       240
taatctctga gtagcaaaga ttcccaaaac tatccaaaat tatccggcgg ctgcggattt       300
gatacgataa aaaaatatcg ctataatcac aaatttattc aaatttacta aaaagggccc       360
acagcctaat taccaaaatc aaattgaact ttcccaattc cacgcaatcc tcaaagataa       420
acacagcaac caccaactaa tactctataa aaaatcatac aaaagtccaa ctaattacac       480
ccctcacgtt acgatagtca aattgtttag tcctttcccc caagcttcga ccattgtttc       540
tcaacatt                                                                548

<210> SEQ ID NO 2
<211> LENGTH: 1319
<212> TYPE: DNA
<213> ORGANISM: Apium graveolens

<400> SEQUENCE: 2
gacccactat caacaatgat caagaatgaa caatacatat acatggtgta tagttaagat        60
ttcaggatat tttattggta tgattgttgc attggtatag atatagcatg ttgagaggaa       120
agtgtttgaa acagagattg caatataagt agggtaggct atagcagact actcttaaac       180
cgagcaccaa aagcttcttg attcatctct agataaatatc agaatgatga ttgcagttca       240
aactatgtgc tgatactcgt aaaactcctc ttcagcagtg gctggttcga tttgttattg       300
gtaaatgaat ttctatactc gatcgcccgg cagaatcggc catctaacat tatatcaaaa       360
ttttatactt tttatcagca tcctaatgag ggtgttaata atctttaata ttaattgttt       420
```

```
gatagagatg atcgtctaat aaacgtaaat atcgtttaag atgatagttc accatcttct        480
ttagaaaggt aaactgattc agataagcat gcttcactta ttggagatgg tgacaacggc        540
attctgcttt tgattgatcg acgccctcgg ttccttatgc aaagcaactt tctcttttgt        600
tagtggacgt ctattagttt caatccattg tcatttctg ctgtaggaat ccttttatt         660 attggaccga aaaattgctc ttcaggctct acctgagaca tatcagatcg taaaccagat        720
caaacatatc aatgtaatc ggcttgtaga tcaggatttt atgtggggtg agatgtacgc        780
atattatata gccaggattt taggtggcat aagatgtacg catatcatat aacacttcta       840
cacttattga gtagaggcaa aacaatttc ttttagtgta tagaaaacta cagagtcgtg         900
cataatgttg aaatcgcatg tttgttggta cagattgaag gtccatgagc ttaagttaaa        960 taaaaatct acgataaaaa tcaccatatg atattcaact ttttacacga gtcagaattc        1020
ataaaatgtt attacctgct caaaattgct aagttatgga atattattgc atggatatta      1080
tactactacc gcaaaaacta tctttaagat aacaatatga agtacaaata atggagttct      1140
tcaggccaca gacaaagctg taccagagga tatataactt ttcgtttgac tggtccaggt      1200
ggacggtcga tagttagcct ccttctcct ttttgcacta taaataaagc tcatgacttc       1260
acaaaacaaa gtcaccagat aagtgagagt gattaataca gagtccacaa cgatcttat       1319

<210> SEQ ID NO 3
<211> LENGTH: 649
<212> TYPE: DNA
<213> ORGANISM: Apium graveolens

<400> SEQUENCE: 3
ttctttattc tgcagctaga gcctacaaga aagtgttcca aaatatcaaa agtgactaat         60
cgattagtta taacttaaca tgttttaact ggtgttttaa ccgatgaatg catatattaa       120
tgaatgcaag atcatctatt tacgaataaa aaatcaataa ttaattgaca tttatcgttt       180
tagaaagaaa gtgttcgaaa atatcaaaag atccaaatcg acgaattgta acttaatatg      240
ttttaactag cgaatacata ttaatgaatg caagatcatc tatttacgaa taaaaaatca      300
ataattaatt aacacatttt tatttgaaaa ccgttttaga aacaaatttg ggagtttccg      360
attctctttt aagattaata tatttgaaaa gttaaaaaca caattaaatt cagaaaatgg      420
gaaagtatca agttgatgaa tatgagatac ttaaaaagga tggacgagag aaggatagca      480
taggccccaa gctccattat caagattcct caagtaacct ttattcattg aagcgtgtgc       540
tcttctcgtg ccactccatc tataaatacc agcccaaatc acacttctgg aaaatatagc      600
aaactacaaa gctctacaat acactcttgc ataccacctt acttcaagc                  649

<210> SEQ ID NO 4
<211> LENGTH: 589
<212> TYPE: DNA
<213> ORGANISM: Apium graveolens

<400> SEQUENCE: 4
aaaatgtttc atattcacaa aagaaatttt gaacagaaac aattgtggat gcacctctct        60
atatatttgt acttttgcat actgtcgtat atatagtaaa gaattactta ataggggtga       120
atgtactcac cgggcaaagt attagtaatt tcttcattaa atatttaag agtcaattta         180 atttgccact gccttttctt tttcagttct tacttcaagg ttagtcaatc tattccggtg       240
aataattacg aacgaatata taatctctga gtagcaaaga ttcccaaaac tatccaaaat      300
tatccggcgg ctgcggattt gatacgataa aaaatatcg ctataatcac aaatttattc       360
```

```
aaatttacta aaaagggccc acagcctaat taccaaaatc aaattgaact ttcccaattc      420
cacgcaatcc tcaaagataa acacagcaac caccaactaa tactctataa aaaatcatac      480
aaaagtccaa ctaattacac ccctcacgtt acgatagtca aattgtttag tcctttcccc      540
caagcttcga ccattgtttc tcaacatttt gtaatctctc tctctctcg                 589
```

<210> SEQ ID NO 5
<211> LENGTH: 1573
<212> TYPE: DNA
<213> ORGANISM: Apium graveolens

<400> SEQUENCE: 5

```
aacgttgcca ataaacttta tgagattgtt tgatgggtag acattgaaga taaaataaag       60
ttgtttcttc ttttgccggg agatattctc aaatctcaaa tattctggac cgaagaagtt      120
tatttgcaat tgcctagttc acaaaataaa ataaacagag ttcactttg tagagcaatt       180 attcgaaatc caccaccatt gacggatgca gctcatcttg gacccactat caacaatgat      240
caagaatgaa caatacatat acatggtgta tagttaagat ttcaggatat tttattggta      300
tgattgttgc attggtatag atatagcatg ttgagaggaa agtgtttgaa acagagattg      360
caatataagt agggtaggct atagcagact actcttaaac cgagcaccaa aagcttcttg      420
attcatctct agataaatatc agaatgatga ttgcagttca aactatgtgc tgatactcgt      480
aaaactcctc ttcagcagtg gctggttcga tttgttattg gtaaatgaat ttctatactc      540
gatcgcccgg cagaatcggc catctaacat tatatcaaaa ttttatactt tttatcagca      600
tcctaatgag ggtgttaata atctttaata ttaattgttt gatagagatg atcgtctaat      660
aaacgtaaat atcgtttaag atgatagttc accatcttct ttagaaaggt aaactgattc      720
agataagcat gcttcactta ttggagatgg tgacaacggc attctgcttt tgattgatcg      780
acgccctcgg ttccttatgc aaagcaactt tctcttttgt tagtggacgt ctattagttt      840
caatccattg tcattttctg ctgtaggaat cctttttatt attggaccga aaaattgctc      900
ttcaggctct acctgagaca tatcagatcg taaaccagat caaacatatc caatgtaatc      960
ggcttgtaga tcaggatttt atgtggggtg agatgtacgc atattatata gccaggatt     1020 taggtggcat aagatgtacg catatcatat aacacttcta cacttattga gtagaggcaa     1080
aacaattttc ttttagtgta tagaaaacta cagagtcgtg cataatgttg aaatcgcatg     1140
tttgttggta cagattgaag gtccatgagc ttaagttaaa taaaaaatct acgataaaaa     1200
tcaccatatg atattcaact ttttacacga gtcagaattc ataaaatgtt attacctgct     1260
caaaattgct aagttatgga atattattgc atggatatta tactactacc gcaaaaacta     1320 tcttaagat aacaatatga agtacaaata atggagttct tcaggccaca gacaaagctg     1380
taccagagga tatataactt ttcgtttgac tggtccaggt ggacggtcga tagttagcct     1440
cctttctcct ttttgcacta taaataaagc tcatgacttc acaaaacaaa gtcaccgat     1500 aagtgagagt gattaataca gagtccacaa cgatcttata atcttaatca ttctctttac     1560
tatccattcg aaa                                                      1573
```

<210> SEQ ID NO 6
<211> LENGTH: 690
<212> TYPE: DNA
<213> ORGANISM: Apium graveolens

<400> SEQUENCE: 6

```
aaagcaacga tttcttttta ccaaattttg ttctttattc tgcagctaga gcctacaaga       60
```

```
aagtgttcca aaatatcaaa agtgactaat cgattagtta taacttaaca tgttttaact    120
ggtgttttaa ccgatgaatg catatattaa tgaatgcaag atcatctatt tacgaataaa    180
aaatcaataa ttaattgaca tttatcgttt tagaaagaaa gtgttcgaaa atatcaaaag    240
atccaaatcg acgaattgta acttaatatg ttttaactag cgaatacata ttaatgaatg    300
caagatcatc tatttacgaa taaaaaatca ataattaatt aacacatttt tatttgaaaa    360
ccgttttaga aacaaatttg ggagtttccg attctctttt aagattaata tatttgaaaa    420
gttaaaaaca caattaaatt cagaaaatgg gaaagtatca agttgatgaa tatgagatac    480
ttaaaaagga tggacgagag aaggatagca taggccccaa gctccattat caagattcct    540 caagtaaccct ttattcattg aagcgtgtgc tcttctcgtg ccactccatc tataaatacc    600
agcccaaatc acacttctgg aaaatatagc aaactacaaa gctctacaat acactcttgc    660
ataccacctt acttcaagct cttaacaacc                                    690

<210> SEQ ID NO 7
<211> LENGTH: 3697
<212> TYPE: DNA
<213> ORGANISM: Apium graveolens
<220> FEATURE:
<221> NAME/KEY: CDS
<222> LOCATION: (590)..(742)
<223> OTHER INFORMATION:
<220> FEATURE:
<221> NAME/KEY: CDS
<222> LOCATION: (2175)..(3230)
<223> OTHER INFORMATION:
<220> FEATURE:
<221> NAME/KEY: CDS
<222> LOCATION: (1007)..(1369)
<223> OTHER INFORMATION:

<400> SEQUENCE: 7
aaaatgtttc atattcacaa aagaaatttt gaacagaaac aattgtggat gcacctctct     60
atatatttgt acttttgcat actgtcgtat atatagtaaa gaattactta ataggggtga    120
atgtactcac cgggcaaagt attagtaatt tcttcattaa atatttaag agtcaatta    180 atttgccact gccttttctt tttcagttct tacttcaagg ttagtcaatc tattccggtg    240
aataattacg aacgaatata taatctctga gtagcaaaga ttcccaaaac tatccaaaat    300
tatccggcgg ctgcggattt gatacgataa aaaaatatcg ctataatcac aaatttattc    360
aaatttacta aaagggccc acagcctaat taccaaaatc aaattgaact ttcccaattc    420
cacgcaatcc tcaagataa acacagcaac caccaactaa tactctataa aaaatcatac    480
aaaagtccaa ctaattacac ccctcacgtt acgatagtca aattgtttag tcctttcccc    540
caagcttcga ccattgtttc tcaacatttt gtaatctctc tctctctcg atg gcc gga    598
                                                      Met Ala Gly
                                                        1 act tct ggc cct tcc ggc ggt gtc gtc gcc gat ccc aag aat ctg agt        646
Thr Ser Gly Pro Ser Gly Gly Val Val Ala Asp Pro Lys Asn Leu Ser
      5                  10                  15 tca cct tta ttt gac gcg gag aaa aaa ccc aaa aat aac aag tat gct        694
Ser Pro Leu Phe Asp Ala Glu Lys Lys Pro Lys Asn Asn Lys Tyr Ala
 20                  25                  30                  35 ttt gct tgt tcc att tta gct tcc atg act tca att cta ctt ggt tat        742
Phe Ala Cys Ser Ile Leu Ala Ser Met Thr Ser Ile Leu Leu Gly Tyr
                 40                  45                  50 ggtacgatgt ctttcaaacc tacacttatt tcagtacac tcacaatgtc acaaattctt     802
cgtaatcgat ctctcttcca cgatcagtat ttttatttta attcaattta ttaaagcttt    862
```

```
cggacagatc tctttagttt taccgacaca tattacatta gaataatctg aacaacactc        922
tgcatgtctt tttgtcttaa ctatcttatg atctaaacac tctacttgtg ttgtgttata        982 acctttcaa ttttttattt ttta gat acg ggg gtt atg agt gga gca gca          1033
                          Asp Thr Gly Val Met Ser Gly Ala Ala
                                      55                  60 atc tac ata aaa aaa gat ctc cgt ttc acc gat gta caa atc gaa atc        1081
Ile Tyr Ile Lys Lys Asp Leu Arg Phe Thr Asp Val Gln Ile Glu Ile
                65                  70                  75 atc gtc gga atc atc aac atc ttc tct ctt ctc ggc tct ttt ctc gcc        1129
Ile Val Gly Ile Ile Asn Ile Phe Ser Leu Leu Gly Ser Phe Leu Ala
            80                  85                  90 gga aga acc tcc gat tgg att ggc cgg aga tac aca atg gtt cta gcc        1177
Gly Arg Thr Ser Asp Trp Ile Gly Arg Arg Tyr Thr Met Val Leu Ala
        95                 100                 105 ggt ggc ata ttt ttt gcc gga gct ttt tta atg gga tgt gct aca aac        1225
Gly Gly Ile Phe Phe Ala Gly Ala Phe Leu Met Gly Cys Ala Thr Asn
    110                 115                 120 ttt gag ttt tta atg gtg ggt cgg ttt gtc gcc ggg atc gga gta ggg        1273
Phe Glu Phe Leu Met Val Gly Arg Phe Val Ala Gly Ile Gly Val Gly
125                 130                 135                 140 tat gct atg atg atc gct ccg gtt tat aca act gag gtt gct ccg gcg        1321
Tyr Ala Met Met Ile Ala Pro Val Tyr Thr Thr Glu Val Ala Pro Ala
                145                 150                 155 tct tct cgg ggt ttt ctc act tct ttc ccg gag gtc ttt att aat gct        1369
Ser Ser Arg Gly Phe Leu Thr Ser Phe Pro Glu Val Phe Ile Asn Ala
            160                 165                 170 ggtgcgtttt tattcgctaa ttaatttata tttatttatt tatttgtata aattagatat       1429
aatttttaat ttaaattgaa taaaacttta ctgtactaaa gatcagataa cgtatatctc       1489
gtgcaaatgt tgtggaacac atcatgaaga taataatatt aagcatatat taaaataatg       1549
ttttattaaa aatatgtgaa ctgttgtttg gtgttaactg cttttttta tttggtgttc       1609 gtgatgtttt aacaacactg accaatatgt aagtgtgtac aactttacca acaaaagata       1669
ctgttattaa agtacagatt atgtgaatat tatttatata aaataaaaaa atatgtaggt       1729
ccagtgaagc attttttcgtc gtttagatgt gtggtcctta tgataggta gagttgtgta       1789 tcttttgctt ttgtacacgt ttacaataag atatttggtt gtcaatttaa cagctgtata       1849
gctttgatga cctgtgttat atattatgtg gtgtacatag gttgtgattg tgatgtttat       1909
ctgataatta gtctgttttt atttgttata tttttgggtt tgaattggtt aacatgtagt       1969
gatgagttgt tgaactcgat ttaattgtat atagttggac agttgtgatt actcgatttg       2029
atcgaatata attggtattg gacagttgtg attggttttt tttggataat gttggcggct       2089
ttttcttgat tatcgtttgg atgataatga aatgttaatt gttattgaca ttacatggta       2149
gatgtaacta tgttgtttgt taaca gga gtt atg ctg ggg tat gta tcc aac       2201
                              Gly Val Met Leu Gly Tyr Val Ser Asn
                                              175                 180 ttt gca ttt gca aag ctt ccg ctt tgg tta ggc tgg agg ttt atg ctt        2249
Phe Ala Phe Ala Lys Leu Pro Leu Trp Leu Gly Trp Arg Phe Met Leu
                185                 190                 195 gga att gga gca gtt cct tcg gtt ggc tta gcc att ggt gta ttg tat        2297
Gly Ile Gly Ala Val Pro Ser Val Gly Leu Ala Ile Gly Val Leu Tyr
            200                 205                 210 atg cct gag tct ccg cgt tgg ctt gtc atg agg ggt caa ctt ggc gaa        2345
Met Pro Glu Ser Pro Arg Trp Leu Val Met Arg Gly Gln Leu Gly Glu
        215                 220                 225 gca agg cgt gta ctg gaa aag act tcg gag agc aaa gaa gaa gct cga        2393
Ala Arg Arg Val Leu Glu Lys Thr Ser Glu Ser Lys Glu Glu Ala Arg
```

-continued

```
             230                 235                 240                 245
caa aga cta gaa gat atc aag gag gct gct gga att cca gaa gaa tgt         2441
Gln Arg Leu Glu Asp Ile Lys Glu Ala Ala Gly Ile Pro Glu Glu Cys
            250                 255                 260 aat gat gac gtt gtt gaa gtt cct aaa cgt agc aaa gac gat gct gtg         2489
Asn Asp Asp Val Val Glu Val Pro Lys Arg Ser Lys Asp Asp Ala Val
            265                 270                 275 tgg aaa gaa ttg ttc ctt cat cct aca cca gct gtt cgc cat gct gct         2537
Trp Lys Glu Leu Phe Leu His Pro Thr Pro Ala Val Arg His Ala Ala
        280                 285                 290 atc act ggc att ggt att cat ttc ttc caa atg gct agt ggt gtt gat         2585
Ile Thr Gly Ile Gly Ile His Phe Phe Gln Met Ala Ser Gly Val Asp
        295                 300                 305 gct gtt gtt ttg tac agt cct cga att ttt gag aag gct ggg tta aag         2633
Ala Val Val Leu Tyr Ser Pro Arg Ile Phe Glu Lys Ala Gly Leu Lys
310                 315                 320                 325 agt gat aac cac aag cta ctc gcc acc att ggt gtt gga gtc tgc aaa         2681
Ser Asp Asn His Lys Leu Leu Ala Thr Ile Gly Val Gly Val Cys Lys
                330                 335                 340 act att ttt gtt ttg ata tca aca ttt ttg cta gac aaa gtc gga cgg         2729
Thr Ile Phe Val Leu Ile Ser Thr Phe Leu Leu Asp Lys Val Gly Arg
            345                 350                 355 cgc cca ctg atg ctt tcg agt atg ggg ggc atg gta att gct cta ctc         2777
Arg Pro Leu Met Leu Ser Ser Met Gly Gly Met Val Ile Ala Leu Leu
            360                 365                 370 gta ctc tca ggc tca ttg tct gta att aat cac tcg cat caa acc gtt         2825
Val Leu Ser Gly Ser Leu Ser Val Ile Asn His Ser His Gln Thr Val
            375                 380                 385 ccc tgg gct gtt gct ttg gca ata att tcg gtg tat ggc ttt gtg tcg         2873
Pro Trp Ala Val Ala Leu Ala Ile Ile Ser Val Tyr Gly Phe Val Ser
390                 395                 400                 405 gtg ttt tca agt ggg atg ggg cca att gct tgg gtg tat agt tcg gag         2921
Val Phe Ser Ser Gly Met Gly Pro Ile Ala Trp Val Tyr Ser Ser Glu
                410                 415                 420 gtg ttt cct ttg agg ctt aga gcc caa ggt tgc agt atc gga gtg gca         2969
Val Phe Pro Leu Arg Leu Arg Ala Gln Gly Cys Ser Ile Gly Val Ala
            425                 430                 435 gtc aat cgt ggt gtt agt ggc att atc gga atg aca ttt ata tca atg         3017
Val Asn Arg Gly Val Ser Gly Ile Ile Gly Met Thr Phe Ile Ser Met
            440                 445                 450 tac aag gcc ttg act att ggt ggt gca ttc ttt gta ttc gct gtg gtt         3065
Tyr Lys Ala Leu Thr Ile Gly Gly Ala Phe Phe Val Phe Ala Val Val
            455                 460                 465 gca gca att gga tgg gta ttc atg ttc aca atg ttt cct gaa act caa         3113
Ala Ala Ile Gly Trp Val Phe Met Phe Thr Met Phe Pro Glu Thr Gln
470                 475                 480                 485 gga aga aat ctt gaa gaa att gag gta ttg ttt ggc agt tac ttt ggc         3161
Gly Arg Asn Leu Glu Glu Ile Glu Val Leu Phe Gly Ser Tyr Phe Gly
                490                 495                 500 tgg agg aaa aca ttg aag gat ttg aag aag aaa gaa gcg gca gaa gca         3209
Trp Arg Lys Thr Leu Lys Asp Leu Lys Lys Lys Glu Ala Ala Glu Ala
            505                 510                 515 aag aat gtc tgc att gtt gct taaaattcaa atacagcggg gattatagct            3260
Lys Asn Val Cys Ile Val Ala
        520 ttgtgatgtt aaatgtgttt gagcgagggt gcaaaaccaa acatacccgg tatattcact       3320 cctaagtaga atttctggag tacctgcgga tttgttgtgt taactaagg gcgatttat         3380 caaaatcctt ggtaccctg gaactcctct aataaattta aacagtatt gtggtttta          3440
```

-continued

```
cttgattcgt gacattccta catttctgct tctcatctct agttttatgt acgcatataa    3500
ttgtgcttag tactcctacg ttattgctca acctctgttt gtgaatcgaa tatggtttgc    3560
tgacatcttc cgagaccaga aacggaaaga gtaaatgttt tttcgcatgt gcaattataa    3620
catcaatgtc ttgcgtttaa ttggtatgat atatgttctc ttgtttgcag cttctttgct    3680
cagttcatat gcacaat                                                   3697
```

<210> SEQ ID NO 8
<211> LENGTH: 524
<212> TYPE: PRT
<213> ORGANISM: Apium graveolens

<400> SEQUENCE: 8

```
Met Ala Gly Thr Ser Gly Pro Ser Gly Val Val Ala Asp Pro Lys
 1               5                  10                  15

Asn Leu Ser Ser Pro Leu Phe Asp Ala Glu Lys Lys Pro Lys Asn Asn
                20                  25                  30

Lys Tyr Ala Phe Ala Cys Ser Ile Leu Ala Ser Met Thr Ser Ile Leu
            35                  40                  45

Leu Gly Tyr Asp Thr Gly Val Met Ser Gly Ala Ala Ile Tyr Ile Lys
        50                  55                  60

Lys Asp Leu Arg Phe Thr Asp Val Gln Ile Glu Ile Val Gly Ile
65                  70                  75                  80

Ile Asn Ile Phe Ser Leu Leu Gly Ser Phe Leu Ala Gly Arg Thr Ser
                85                  90                  95

Asp Trp Ile Gly Arg Arg Tyr Thr Met Val Leu Ala Gly Ile Phe
            100                 105                 110

Phe Ala Gly Ala Phe Leu Met Gly Cys Ala Thr Asn Phe Glu Phe Leu
        115                 120                 125

Met Val Gly Arg Phe Val Ala Gly Ile Gly Val Gly Tyr Ala Met Met
    130                 135                 140

Ile Ala Pro Val Tyr Thr Thr Glu Val Ala Pro Ala Ser Ser Arg Gly
145                 150                 155                 160

Phe Leu Thr Ser Phe Pro Glu Val Phe Ile Asn Ala Gly Val Met Leu
                165                 170                 175

Gly Tyr Val Ser Asn Phe Ala Phe Ala Lys Leu Pro Leu Trp Leu Gly
            180                 185                 190

Trp Arg Phe Met Leu Gly Ile Gly Ala Val Pro Ser Val Gly Leu Ala
        195                 200                 205

Ile Gly Val Leu Tyr Met Pro Glu Ser Pro Arg Trp Leu Val Met Arg
    210                 215                 220

Gly Gln Leu Gly Glu Ala Arg Arg Val Leu Glu Lys Thr Ser Glu Ser
225                 230                 235                 240

Lys Glu Glu Ala Arg Gln Arg Leu Glu Asp Ile Lys Glu Ala Ala Gly
                245                 250                 255

Ile Pro Glu Glu Cys Asn Asp Val Val Glu Val Pro Lys Arg Ser
            260                 265                 270

Lys Asp Asp Ala Val Trp Lys Glu Leu Phe Leu His Pro Thr Pro Ala
        275                 280                 285

Val Arg His Ala Ala Ile Thr Gly Ile Gly Ile His Phe Phe Gln Met
    290                 295                 300

Ala Ser Gly Val Asp Ala Val Val Leu Tyr Ser Pro Arg Ile Phe Glu
305                 310                 315                 320

Lys Ala Gly Leu Lys Ser Asp Asn His Lys Leu Leu Ala Thr Ile Gly
                325                 330                 335
```

```
Val Gly Val Cys Lys Thr Ile Phe Val Leu Ile Ser Thr Phe Leu Leu
            340                 345                 350

Asp Lys Val Gly Arg Arg Pro Leu Met Leu Ser Ser Met Gly Gly Met
            355                 360                 365

Val Ile Ala Leu Leu Val Leu Ser Gly Ser Leu Ser Val Ile Asn His
370                 375                 380

Ser His Gln Thr Val Pro Trp Ala Val Ala Leu Ala Ile Ile Ser Val
385                 390                 395                 400

Tyr Gly Phe Val Ser Val Phe Ser Ser Gly Met Gly Pro Ile Ala Trp
                405                 410                 415

Val Tyr Ser Ser Glu Val Phe Pro Leu Arg Leu Arg Ala Gln Gly Cys
                420                 425                 430

Ser Ile Gly Val Ala Val Asn Arg Gly Val Ser Gly Ile Ile Gly Met
            435                 440                 445

Thr Phe Ile Ser Met Tyr Lys Ala Leu Thr Ile Gly Gly Ala Phe Phe
450                 455                 460

Val Phe Ala Val Ala Ala Ile Gly Trp Val Phe Met Phe Thr Met
465                 470                 475                 480

Phe Pro Glu Thr Gln Gly Arg Asn Leu Glu Glu Ile Glu Val Leu Phe
                485                 490                 495

Gly Ser Tyr Phe Gly Trp Arg Lys Thr Leu Lys Asp Leu Lys Lys Lys
                500                 505                 510

Glu Ala Ala Glu Ala Lys Asn Val Cys Ile Val Ala
            515                 520

<210> SEQ ID NO 9
<211> LENGTH: 2042
<212> TYPE: DNA
<213> ORGANISM: Apium graveolens
<220> FEATURE:
<221> NAME/KEY: CDS
<222> LOCATION: (1574)..(1801)
<223> OTHER INFORMATION:
<220> FEATURE:
<221> NAME/KEY: misc_feature
<222> LOCATION: (1920)..(1920)
<223> OTHER INFORMATION: undefined
<220> FEATURE:
<221> NAME/KEY: misc_feature
<222> LOCATION: (1979)..(1979)
<223> OTHER INFORMATION: undefined
<220> FEATURE:
<221> NAME/KEY: misc_feature
<222> LOCATION: (1994)..(1994)
<223> OTHER INFORMATION: undefined
<220> FEATURE:
<221> NAME/KEY: misc_feature
<222> LOCATION: (2017)..(2017)
<223> OTHER INFORMATION: undefined

<400> SEQUENCE: 9
aacgttgcca aataacttta tgagattgtt tgatgggtag acattgaaga taaaataaag    60
ttgtttcttc ttttgccggg agatattctc aaatctcaaa tattctggac cgaagaagtt   120
tatttgcaat tgcctagttc acaaaataaa ataaacagag ttcactttg tagagcaatt    180 attcgaaatc caccaccatt gacggatgca gctcatcttg acccactat caacaatgat    240 caagaatgaa caatacatat acatggtgta tagttaagat ttcaggatat tttattggta    300
tgattgttgc attggtatag atatagcatg ttgagaggaa agtgtttgaa acagagattg    360
caatataagt agggtaggct atagcagact actcttaaac cgagcaccaa aagcttcttg    420
attcatctct agataatatc agaatgatga ttgcagttca aactatgtgc tgatactcgt    480
```

```
aaaactcctc ttcagcagtg gctggttcga tttgttattg gtaaatgaat ttctatactc    540
gatcgcccgg cagaatcggc catctaacat tatatcaaaa ttttatactt tttatcagca    600
tcctaatgag ggtgttaata atctttaata ttaattgttt gatagagatg atcgtctaat    660
aaacgtaaat atcgtttaag atgatagttc accatcttct ttagaaaggt aaactgattc    720
agataagcat gcttcactta ttggagatgg tgacaacggc attctgcttt tgattgatcg    780
acgccctcgg ttccttatgc aaagcaactt tctcttttgt tagtggacgt ctattagttt    840
caatccattg tcattttctg ctgtaggaat ccttttttatt attggaccga aaaattgctc    900
ttcaggctct acctgagaca tatcagatcg taaaccagat caaacatatc caatgtaatc    960
ggcttgtaga tcaggatttt atgtggggtg agatgtacgc atattatata gccaggatt    1020 taggtggcat aagatgtacg catatcatat aacacttcta cacttattga gtagaggcaa   1080 aacaatttc ttttagtgta tagaaaacta cagagtcgtg cataatgttg aaatcgcatg    1140
tttgttggta cagattgaag gtccatgagc ttaagttaaa taaaaaatct acgataaaaa    1200
tcaccatatg atattcaact ttttacacga gtcagaattc ataaaatgtt attacctgct    1260
caaaattgct aagttatgga atattattgc atggatatta tactactacc gcaaaaacta    1320
tctttaagat aacaatatga agtacaaata atggagttct tcaggccaca gacaaagctg    1380
taccagagga tatataactt tcgtttgac tggtccaggt ggacggtcga tagttagcct    1440
cctttctcct ttttgcacta taaataaagc tcatgacttc acaaaacaaa gtcaccagat    1500
aagtgagagt gattaataca gagtccacaa cgatcttata atcttaatca ttctctttac    1560
tatccattcg aaa atg tct tgc tgt gga gga aac tgt ggt tgt ggt gct    1609
              Met Ser Cys Cys Gly Gly Asn Cys Gly Cys Gly Ala
                1               5                  10 ggc tgc aag tgc ggc aat ggc tgt gga gga tgc gga atg tac cct gat    1657
Gly Cys Lys Cys Gly Asn Gly Cys Gly Gly Cys Gly Met Tyr Pro Asp
         15                  20                  25 gtg gag aag aac aca act gca acc atc att gat gga gtt gca cca aca    1705
Val Glu Lys Asn Thr Thr Ala Thr Ile Ile Asp Gly Val Ala Pro Thr
     30                  35                  40 aag acg ttt tct cag ggt tca gag atg agc ttt aca act gaa gga ggg    1753
Lys Thr Phe Ser Gln Gly Ser Glu Met Ser Phe Thr Thr Glu Gly Gly
 45                  50                  55                  60 cat gcc tgc aag tgc gga tca aac tgc aca tgt aat ccg tgc aaa tgt    1801
His Ala Cys Lys Cys Gly Ser Asn Cys Thr Cys Asn Pro Cys Lys Cys
             65                  70                  75 taacgatgaa atggaactga gtacctaaca aagcagctag cgtttctcca atattgtact    1861
ataataatgc cgcagcctgt gttttatgct attccagact tggatgtgtt taatgttgnt    1921
aggctgctta atcttttttt tttatgtttt tcgtaactac cgttgctctc tgctttgngg    1981
gtactggtat tgncttaagg gttaattcat ctgcgngatg aaactaatgg catgaaattc    2041
t                                                                  2042
```

<210> SEQ ID NO 10
<211> LENGTH: 76
<212> TYPE: PRT
<213> ORGANISM: Apium graveolens

<400> SEQUENCE: 10

Met Ser Cys Cys Gly Gly Asn Cys Gly Cys Gly Ala Gly Cys Lys Cys
1               5                   10                  15

Gly Asn Gly Cys Gly Gly Cys Gly Met Tyr Pro Asp Val Glu Lys Asn
            20                  25                  30

```
Thr Thr Ala Thr Ile Ile Asp Gly Val Ala Pro Thr Lys Thr Phe Ser
        35                  40                  45
Gln Gly Ser Glu Met Ser Phe Thr Thr Glu Gly His Ala Cys Lys
 50                  55                  60
Cys Gly Ser Asn Cys Thr Cys Asn Pro Cys Lys Cys
 65                  70                  75
```

<210> SEQ ID NO 11
<211> LENGTH: 1102
<212> TYPE: DNA
<213> ORGANISM: Apium graveolens
<220> FEATURE:
<221> NAME/KEY: CDS
<222> LOCATION: (691)..(891)
<223> OTHER INFORMATION:
<220> FEATURE:
<221> NAME/KEY: misc_feature
<222> LOCATION: (802)..(802)
<223> OTHER INFORMATION: undefined

<400> SEQUENCE: 11

```
aaagcaacga tttcttttta ccaaattttg ttctttattc tgcagctaga gcctacaaga     60
aagtgttcca aaatatcaaa agtgactaat cgattagtta aacttaaca tgttttaact    120 ggtgttttaa ccgatgaatg catatattaa tgaatgcaag atcatctatt tacgaataaa    180
aaatcaataa ttaattgaca tttatcgttt tagaaagaaa gtgttcgaaa atatcaaaag    240
atccaaatcg acgaattgta acttaatatg ttttaactag cgaatacata ttaatgaatg    300
caagatcatc tatttacgaa taaaaaatca ataattaatt aacacatttt tatttgaaaa    360 ccgtttttaga aacaaatttg ggagtttccg attctctttt aagattaata tatttgaaaa    420
gttaaaaaca caattaaatt cagaaaatgg gaaagtatca agttgatgaa tatgagatac    480
ttaaaaagga tggacgagag aaggatagca taggccccaa gctccattat caagattcct    540 caagtaaacct ttattcattg aagcgtgtgc tcttctcgtg ccactccatc tataaatacc    600
agcccaaatc acacttctgg aaaatatagc aaactacaaa gctctacaat acactcttgc    660 ataccaccctt acttcaagct cttaacaacc atg tcg aac acc tgt ggc aac tgt     714
                                Met Ser Asn Thr Cys Gly Asn Cys
                                  1               5 gac tgc tcc gac aag agc cag tgc gtg aag aag gga gcc agc tat ggc    762
Asp Cys Ser Asp Lys Ser Gln Cys Val Lys Lys Gly Ala Ser Tyr Gly
     10                  15                  20 ctt gac att gtt gaa act gga aag agc tat gtc cag acc nct gtg atg    810
Leu Asp Ile Val Glu Thr Gly Lys Ser Tyr Val Gln Thr Xaa Val Met
 25                  30                  35                  40 gaa gtc tcg gca act gag aac gac ggc aag tgc aaa tgc gga aca agc    858
Glu Val Ser Ala Thr Glu Asn Asp Gly Lys Cys Lys Cys Gly Thr Ser
                 45                  50                  55 tgc act tgt gtg aac tgc agt tgc ggt ggt cac taagcagccc ttctccatcc    911
Cys Thr Cys Val Asn Cys Ser Cys Gly Gly His
             60                  65 tccagacaac tataatatgt tacaaataga acttgtgcat gcatgagctc tgtcacaataa    971 aactgtgact atagtgtcaa gtgtctgagt gtcaattagt ccccttgtat ttcagtttcc   1031
ttgttacctg tgtaatgtgt tcacagctgc tacattagta cagttgtgtt aaatgaatca   1091
cttcctagtt t                                                       1102
```

<210> SEQ ID NO 12
<211> LENGTH: 67
<212> TYPE: PRT

<213> ORGANISM: Apium graveolens
<220> FEATURE:
<221> NAME/KEY: misc_feature
<222> LOCATION: (38)..(38)
<223> OTHER INFORMATION: The 'Xaa' at location 38 stands for Thr, Ala, Pro, or Ser.

<400> SEQUENCE: 12

```
Met Ser Asn Thr Cys Gly Asn Cys Asp Cys Ser Asp Lys Ser Gln Cys
1               5                   10                  15

Val Lys Lys Gly Ala Ser Tyr Gly Leu Asp Ile Val Glu Thr Gly Lys
            20                  25                  30

Ser Tyr Val Gln Thr Xaa Val Met Glu Val Ser Ala Thr Glu Asn Asp
        35                  40                  45

Gly Lys Cys Lys Cys Gly Thr Ser Cys Thr Cys Val Asn Cys Ser Cys
    50                  55                  60

Gly Gly His
65
```

<210> SEQ ID NO 13
<211> LENGTH: 3108
<212> TYPE: DNA
<213> ORGANISM: Apium graveolens

<400> SEQUENCE: 13

| | |
|---|---|
| atggccggaa cttctggccc ttccggcggt gtcgtcgccg atcccaagaa tctgagttca | 60 |
| cctttatttg acgcggagaa aaaacccaaa aataacaagt atgcttttgc ttgttccatt | 120 |
| ttagcttcca tgacttcaat tctacttggt tatggtacga tgtctttcaa acctacactt | 180 |
| attttcagta cactcacaat gtcacaaatt cttcgtaatc gatctctctt ccacgatcag | 240 |
| tattttatt ttaattcaat ttattaaagc tttcggacag atctctttag ttttaccgac | 300 |
| acatattaca ttagaataat ctgaacaaca ctctgcatgt ctttttgtct taactatctt | 360 |
| atgatctaaa cactctactt gtgttgtgtt ataaccttt caatttttta tttttagat | 420 |
| acggggtta tgagtggagc agcaatctac ataaaaaaag atctccgttt caccgatgta | 480 |
| caaatcgaaa tcatcgtcgg aatcatcaac atcttctctc ttctcggctc ttttctcgcc | 540 |
| ggaagaacct ccgattggat tggccggaga tacacaatgg ttctagccgg tggcatattt | 600 |
| tttgccggag cttttttaat gggatgtgct acaaactttg agtttttaat ggtgggtcgg | 660 |
| tttgtcgccg ggatcggagt agggtatgct atgatgatcg ctccggttta tacaactgag | 720 |
| gttgctccgg cgtcttctcg ggttttctc acttcttttcc cggaggtctt tattaatgct | 780 |
| ggtgcgtttt tattcgctaa ttaatttata tttatttatt tatttgtata aattagatat | 840 |
| aattttaat ttaaattgaa taaaacttta ctgtactaaa gatcagataa cgtatatctc | 900 |
| gtgcaaatgt tgtggaacac atcatgaaga taataatatt aagcatatat taaaataatg | 960 |
| ttttattaaa aatatgtgaa ctgttgtttg gtgttaactg ctttttttta tttggtgttc | 1020 |
| gtgatgtttt aacaacactg accaatatgt aagtgtgtac aactttacca acaaaagata | 1080 |
| ctgttattaa agtacagatt atgtgaatat tatttatata aaataaaaaa atatgtaggt | 1140 |
| ccagtgaagc atttttcgtc gtttagatgt gtggtccctta ttgataggta gagttgtgta | 1200 |
| tcttttgctt ttgtacacgt ttacaataag atatttggtt gtcaatttaa cagctgtata | 1260 |
| gctttgatga cctgtgttat atattatgtg gtgtacatag gttgtgattg tgatgttat | 1320 |
| ctgataatta gtctgttttt atttgttata ttttgggtt tgaattggtt aacatgtagt | 1380 |
| gatgagttgt tgaactcgat ttaattgtat atagttggac agttgtgatt actcgatttg | 1440 |

-continued

| | |
|---|---|
| atcgaatata attggtattg gacagttgtg attggttttt tttggataat gttggcggct | 1500 |
| ttttcttgat tatcgtttgg atgataatga aatgttaatt gttattgaca ttacatggta | 1560 |
| gatgtaacta tgttgtttgt taacaggagt tatgctgggg tatgtatcca actttgcatt | 1620 |
| tgcaaagctt ccgctttggt taggctggag gtttatgctt ggaattggag cagttccttc | 1680 |
| ggttggctta gccattggtg tattgtatat gcctgagtct ccgcgttggc ttgtcatgag | 1740 |
| gggtcaactt ggcgaagcaa ggcgtgtact ggaaaagact tcggagagca agaagaagc | 1800 |
| tcgacaaaga ctagaagata tcaaggaggc tgctggaatt ccagaagaat gtaatgatga | 1860 |
| cgttgttgaa gttcctaaac gtagcaaaga cgatgctgtg tggaaagaat gttccttca | 1920 |
| tcctacacca gctgttcgcc atgctgctat cactggcatt ggtattcatt tcttccaaat | 1980 |
| ggctagtggt gttgatgctg ttgttttgta cagtcctcga atttttgaga aggctgggtt | 2040 |
| aaagagtgat aaccacaagc tactcgccac cattggtgtt ggagtctgca aaactatttt | 2100 |
| tgttttgata tcaacatttt tgctagacaa agtcggacgg cgcccactga tgctttcgag | 2160 |
| tatgggggc atggtaattg ctctactcgt actctcaggc tcattgtctg taattaatca | 2220 |
| ctcgcatcaa accgttccct gggctgttgc tttggcaata atttcggtgt atggctttgt | 2280 |
| gtcggtgttt tcaagtggga tggggccaat tgcttgggtg tatagttcgg aggtgtttcc | 2340 |
| tttgaggctt agagcccaag gttgcagtat cggagtggca gtcaatcgtg tgttagtgg | 2400 |
| cattatcgga atgacattta tatcaatgta caaggccttg actattggtg gtgcattctt | 2460 |
| tgtattcgct gtggttgcag caattggatg ggtattcatg ttcacaatgt ttcctgaaac | 2520 |
| tcaaggaaga aatcttgaag aaattgaggt attgtttggc agttactttg gctggaggaa | 2580 |
| aacattgaag gatttgaaga agaaagaagc ggcagaagca agaatgtct gcattgttgc | 2640 |
| ttaaaattca aatacagcgg ggattatagc tttgtgatgt taaatgtgtt tgagcgaggg | 2700 |
| tgcaaaacca acatacccg gtatattcac tcctaagtag aatttctgga gtacctgcgg | 2760 |
| atttgtttgt gttaactaag ggcgatttta tcaaaatcct tggtaccctt ggaactcctc | 2820 |
| taataaattt aaaacagtat tgtggttttt acttgattcg tgacattcct acatttctgc | 2880 |
| ttctcatctc tagttttatg tacgcatata attgtgctta gtactcctac gttattgctc | 2940 |
| aacctctgtt tgtgaatcga atatggtttg ctgacatctt ccgagaccag aaacggaaag | 3000 |
| agtaaatgtt ttttcgcatg tgcaattata acatcaatgt cttgcgttta attggtatga | 3060 |
| tatatgttct cttgtttgca gcttctttgc tcagttcata tgcacaat | 3108 |

<210> SEQ ID NO 14
<211> LENGTH: 1575
<212> TYPE: DNA
<213> ORGANISM: Apium graveolens

<400> SEQUENCE: 14

| | |
|---|---|
| atggccggaa cttctggccc ttccggcggt gtcgtcgccg atcccaagaa tctgagttca | 60 |
| cctttatttg acgcggagaa aaaacccaaa aataacaagt atgcttttgc ttgttccatt | 120 |
| ttagcttcca tgacttcaat tctacttggt tatgatacgg gggttatgag tggagcagca | 180 |
| atctacataa aaaaagatct ccgtttcacc gatgtacaaa tcgaaatcat cgtcggaatc | 240 |
| atcaacatct tctctcttct cggctctttt ctcgccggaa gaacctccga ttggattggc | 300 |
| cggagataca caatggttct agccggtggc atattttttg ccggagcttt tttaatggga | 360 |
| tgtgctacaa actttgagtt tttaatggtg ggtcggtttg tcgccgggat cggagtaggg | 420 |
| tatgctatga tgatcgctcc ggtttataca actgaggttg ctccggcgtc ttctcggggt | 480 |

```
tttctcactt ctttcccgga ggtctttatt aatgctggag ttatgctggg gtatgtatcc      540
aactttgcat ttgcaaagct tccgctttgg ttaggctgga ggtttatgct tggaattgga      600
gcagttcctt cggttggctt agccattggt gtattgtata tgcctgagtc tccgcgttgg      660
cttgtcatga ggggtcaact tggcgaagca aggcgtgtac tggaaaagac ttcggagagc      720
aaagaagaag ctcgacaaag actagaagat atcaaggagg ctgctggaat tccagaagaa      780
tgtaatgatg acgttgttga agttcctaaa cgtagcaaag acgatgctgt gtggaaagaa      840
ttgttccttc atcctacacc agctgttcgc catgctgcta tcactggcat tggtattcat      900
ttcttccaaa tggctagtgg tgttgatgct gttgttttgt acagtcctcg aattttgag       960 aaggctgggt taaagagtga taaccacaag ctactcgcca ccattggtgt tggagtctgc     1020
aaaactattt tgttttgat atcaacattt tgctagaca aagtcggacg gcgcccactg       1080
atgctttcga gtatgggggg catggtaatt gctctactcg tactctcagg ctcattgtct     1140
gtaattaatc actcgcatca aaccgttccc tgggctgttg cttt ggcaat aatttcggtg    1200 tatggctttg tgtcggtgtt ttcaagtggg atggggccaa ttgcttgggt gtatagttcg     1260
gaggtgtttc ctttgaggct tagagcccaa ggttgcagta tcggagtggc agtcaatcgt    1320
ggtgttagtg gcattatcgg aatgacattt atatcaatgt acaaggcctt gactattggt    1380
ggtgcattct ttgtattcgc tgtggttgca gcaattggat gggtattcat gttcacaatg    1440
tttcctgaaa ctcaaggaag aaatcttgaa gaaattgagg tattgtttgg cagttacttt   1500
ggctggagga aaacattgaa ggatttgaag aagaagaag cggcagaagc aaagaatgtc     1560
tgcattgttg cttaa                                                     1575
```

<210> SEQ ID NO 15
<211> LENGTH: 50
<212> TYPE: DNA
<213> ORGANISM: Artificial
<220> FEATURE:
<223> OTHER INFORMATION: primer

<400> SEQUENCE: 15
ggggacaagt ttgtacaaaa aagcaggctg aacagaaaca attgtggatg                50

<210> SEQ ID NO 16
<211> LENGTH: 50
<212> TYPE: DNA
<213> ORGANISM: artificial
<220> FEATURE:
<223> OTHER INFORMATION: primer

<400> SEQUENCE: 16
ggggaccact ttgtacaaga aagctgggta atgttgagaa acaatggtcg                50

<210> SEQ ID NO 17
<211> LENGTH: 50
<212> TYPE: DNA
<213> ORGANISM: Artificial
<220> FEATURE:
<223> OTHER INFORMATION: primer

<400> SEQUENCE: 17
ggggacaagt ttgtacaaaa aagcaggctg acccactatc aacaatgatc                50

<210> SEQ ID NO 18
<211> LENGTH: 50
<212> TYPE: DNA
<213> ORGANISM: Artificial
<220> FEATURE:

<223> OTHER INFORMATION: primer

<400> SEQUENCE: 18
ggggaccact ttgtacaaga aagctgggta taagatcgtt gtggactctg         50

<210> SEQ ID NO 19
<211> LENGTH: 50
<212> TYPE: DNA
<213> ORGANISM: Artificial
<220> FEATURE:
<223> OTHER INFORMATION: primer

<400> SEQUENCE: 19
ggggacaagt ttgtacaaaa aagcaggctt ctttattctg cagctagagc         50

<210> SEQ ID NO 20
<211> LENGTH: 50
<212> TYPE: DNA
<213> ORGANISM: Artificial
<220> FEATURE:
<223> OTHER INFORMATION: primer

<400> SEQUENCE: 20
ggggaccact ttgtacaaga aagctgggtg cttgaagtaa ggtggtatgc         50

<210> SEQ ID NO 21
<211> LENGTH: 23
<212> TYPE: DNA
<213> ORGANISM: Artificial
<220> FEATURE:
<223> OTHER INFORMATION: primer

<400> SEQUENCE: 21
atacagcggg gattatagct ttg                                      23

<210> SEQ ID NO 22
<211> LENGTH: 23
<212> TYPE: DNA
<213> ORGANISM: Artificial
<220> FEATURE:
<223> OTHER INFORMATION: primer

<400> SEQUENCE: 22
atccgcaggt actccaaaaa ttt                                      23

<210> SEQ ID NO 23
<211> LENGTH: 18
<212> TYPE: DNA
<213> ORGANISM: Artificial
<220> FEATURE:
<223> OTHER INFORMATION: probe

<400> SEQUENCE: 23
tacccggtat attcactc                                            18

<210> SEQ ID NO 24
<211> LENGTH: 18
<212> TYPE: DNA
<213> ORGANISM: Artificial
<220> FEATURE:
<223> OTHER INFORMATION: primer

<400> SEQUENCE: 24
agccgctgga ccctacct                                            18

<210> SEQ ID NO 25

```
<211> LENGTH: 25
<212> TYPE: DNA
<213> ORGANISM: Artificial
<220> FEATURE:
<223> OTHER INFORMATION: primer

<400> SEQUENCE: 25
agttatcttt tctgtttaac agcct                                         25

<210> SEQ ID NO 26
<211> LENGTH: 16
<212> TYPE: DNA
<213> ORGANISM: Artificial
<220> FEATURE:
<223> OTHER INFORMATION: probe

<400> SEQUENCE: 26
ctaagccgtt tccagg                                                   16

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
gactagtccc aagaatctga gttcacc                                       27

<210> SEQ ID NO 28
<211> LENGTH: 28
<212> TYPE: DNA
<213> ORGANISM: Artificial
<220> FEATURE:
<223> OTHER INFORMATION: primer

<400> SEQUENCE: 28
ccgctcgagc atcacaaagc tataatcc                                      28

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
agcttcgacc attgtttctc                                               20

<210> SEQ ID NO 30
<211> LENGTH: 28
<212> TYPE: DNA
<213> ORGANISM: Artificial
<220> FEATURE:
<223> OTHER INFORMATION: primer

<400> SEQUENCE: 30
ccgctcgagc atcacaaagc tataatcc                                      28

<210> SEQ ID NO 31
<211> LENGTH: 518
<212> TYPE: PRT
<213> ORGANISM: Apium graveolens

<400> SEQUENCE: 31

Met Thr Gly Ala Ser Met Ile Thr Gly Glu Val Ser Val Asp Ser Tyr
 1               5                  10                  15
```

-continued

```
Asp Thr Asn Lys Pro Lys Pro Lys Arg Asn Lys Tyr Ala Phe Ala Cys
            20                  25                  30
Ala Leu Leu Ala Ser Met Asn Ser Ile Leu Leu Gly Tyr Asp Thr Gly
        35                  40                  45
Val Leu Ser Gly Ala Ser Ile Tyr Ile Lys Glu Asp Leu His Phe Ser
 50                  55                  60
Asp Val Gln Ile Glu Ile Ile Gly Ile Ile Asn Ile Tyr Ser Leu
 65                  70                  75                  80
Leu Gly Ser Ala Ile Ala Gly Arg Thr Ser Asp Trp Ile Gly Arg Arg
                85                  90                  95
Tyr Thr Met Val Leu Ala Gly Ile Ile Phe Phe Leu Gly Ala Ile Phe
                    100                 105                 110
Met Gly Leu Ala Thr Asn Phe Ala Phe Leu Met Phe Gly Arg Phe Val
            115                 120                 125
Ala Gly Ile Gly Val Gly Tyr Ala Met Met Ile Ala Pro Val Tyr Thr
        130                 135                 140
Ala Glu Val Ala Pro Ser Ser Ser Arg Gly Phe Leu Thr Ser Phe Pro
145                 150                 155                 160
Glu Val Phe Ile Asn Ser Gly Val Leu Leu Gly Tyr Val Ser Asn Phe
                    165                 170                 175
Ala Phe Ala Lys Cys Pro Leu Trp Leu Gly Trp Arg Ile Met Leu Gly
            180                 185                 190
Ile Gly Ala Phe Pro Ser Val Ala Leu Ala Ile Ile Val Leu Tyr Met
        195                 200                 205
Pro Glu Ser Pro Arg Trp Leu Val Met Gln Gly Arg Leu Gly Glu Ala
210                 215                 220
Arg Thr Val Leu Glu Lys Thr Ser Thr Ser Lys Glu Glu Ala His Gln
225                 230                 235                 240
Arg Leu Ser Asp Ile Lys Glu Ala Ala Gly Ile Asp Lys Asp Cys Asn
                    245                 250                 255
Asp Asp Val Val Gln Val Pro Lys Arg Thr Lys Asp Glu Ala Val Trp
            260                 265                 270
Lys Glu Leu Ile Leu His Pro Thr Lys Pro Val Arg His Ala Ala Ile
        275                 280                 285
Thr Gly Ile Gly Ile His Phe Phe Gln Gln Ala Cys Gly Ile Asp Ala
        290                 295                 300
Val Val Leu Tyr Ser Pro Arg Ile Phe Glu Lys Ala Gly Ile Lys Ser
305                 310                 315                 320
Asn Ser Lys Lys Leu Leu Ala Thr Ile Ala Val Gly Val Cys Lys Thr
                    325                 330                 335
Val Phe Ile Leu Ile Ser Thr Phe Gln Leu Asp Lys Ile Gly Arg Arg
            340                 345                 350
Pro Leu Met Leu Thr Ser Met Gly Gly Met Val Ile Ala Leu Phe Val
        355                 360                 365
Leu Ala Gly Ser Leu Thr Val Ile Asn Lys Ser His His Thr Gly His
        370                 375                 380
Trp Ala Gly Gly Leu Ala Ile Phe Thr Val Tyr Ala Phe Val Ser Ile
385                 390                 395                 400
Phe Ser Ser Gly Met Gly Pro Ile Ala Trp Val Tyr Ser Ser Glu Val
                    405                 410                 415
Phe Pro Leu Arg Leu Arg Ala Gln Gly Cys Ser Ile Gly Val Ala Val
            420                 425                 430
Asn Arg Gly Met Ser Gly Ile Ile Gly Met Thr Phe Ile Ser Met Tyr
```

```
                   435                 440                 445
Lys Ala Met Thr Ile Gly Gly Ala Phe Leu Leu Phe Ala Val Val Ala
        450                 455                 460

Ser Ile Gly Trp Val Phe Met Tyr Thr Met Phe Pro Glu Thr Gln Gly
465                 470                 475                 480

Arg Asn Leu Glu Glu Ile Glu Leu Leu Phe Gly Ser Tyr Phe Gly Trp
                485                 490                 495

Arg Lys Thr Leu Lys Asp Leu Lys Ala Lys Glu Ala Ala Glu Ala Lys
                500                 505                 510

Ser Arg Glu Ser Glu Val
        515

<210> SEQ ID NO 32
<211> LENGTH: 524
<212> TYPE: PRT
<213> ORGANISM: Apium graveolens

<400> SEQUENCE: 32

Met Ala Gly Ala Phe Asn Val Ser Gly Asp Ser Gly Gly Ser Lys
1               5                   10                  15

Asp Val Gly Ser Pro Val Ile Phe Asp Ala Val Lys Lys Pro Lys Arg
                20                  25                  30

Asn Lys Tyr Ala Phe Gly Cys Ala Ile Leu Ala Ser Met Thr Ser Val
            35                  40                  45

Leu Leu Gly Tyr Asp Ile Gly Val Met Ser Gly Ala Ala Ile Tyr Ile
    50                  55                  60

Lys Asp Gln Leu His Val Ser Asp Val Lys Leu Glu Ile Val Val Gly
65              70                  75                  80

Ile Ile Asn Phe Phe Ser Leu Val Gly Ser Ala Leu Ala Gly Arg Thr
                85                  90                  95

Ser Asp Trp Ile Gly Arg Arg Tyr Thr Met Val Leu Ala Gly Ala Ile
            100                 105                 110

Phe Phe Val Gly Ala Ile Leu Met Gly Phe Ala Thr Asn Tyr Ser Phe
        115                 120                 125

Leu Met Phe Gly Arg Phe Val Ala Gly Ile Gly Val Gly Tyr Ala Leu
    130                 135                 140

Met Ile Ala Pro Val Tyr Thr Ala Glu Val Ser Ser Ala Ser Ser Arg
145                 150                 155                 160

Gly Phe Leu Thr Ser Phe Pro Glu Val Phe Ile Asn Ile Gly Val Leu
                165                 170                 175

Leu Gly Tyr Val Ser Asn Tyr Ala Phe Ser Lys Leu Pro Ala Asn Leu
            180                 185                 190

Gly Trp Arg Phe Met Leu Gly Ile Gly Ala Ile Pro Ser Ile Gly Leu
        195                 200                 205

Ala Ile Gly Val Leu Gly Met Pro Glu Ser Pro Arg Trp Leu Val Met
    210                 215                 220

Lys Gly Arg Leu Gly Glu Ala Arg Gln Val Leu Asp Lys Thr Ser Asp
225                 230                 235                 240

Ser Lys Glu Glu Ser Arg Leu Arg Leu Ser Asp Ile Lys Gln Ala Ala
                245                 250                 255

Gly Ile Pro Glu Glu Cys Asn Asp Asp Ile Val Val Met Pro Lys Arg
            260                 265                 270

Arg Asn Asp Glu Ala Val Trp Lys Glu Leu Leu Leu His Pro Thr Pro
        275                 280                 285

Ser Val Arg His Ala Phe Ile Ala Gly Val Gly Leu His Phe Phe Gln
```

```
                290                 295                 300
Gln Ser Ser Gly Ile Asp Ala Gly Gly Leu Tyr Ser Pro Arg Ile Phe
305                 310                 315                 320
Glu Lys Ala Gly Ile Thr Ser Thr Asp Leu Lys Leu Leu Ala Thr Ile
                325                 330                 335
Ala Val Gly Ile Ser Lys Thr Leu Phe Ile Leu Val Ala Thr Phe Leu
                340                 345                 350
Leu Asp Arg Ile Gly Arg Arg Pro Leu Leu Leu Thr Ser Met Gly Gly
                355                 360                 365
Met Ile Ile Ser Leu Thr Leu Leu Gly Thr Ser Leu Ala Val Ile Asp
370                 375                 380
His Ser Asp His Thr Val His Trp Ala Val Ala Leu Ala Ile Phe Gly
385                 390                 395                 400
Val Leu Ala Tyr Val Gly Thr Phe Ser Ile Gly Leu Gly Pro Ile Ala
                405                 410                 415
Trp Gly Tyr Ser Ser Glu Val Phe Pro Leu Arg Leu Arg Ala Gln Gly
                420                 425                 430
Cys Ser Ile Gly Val Ala Val Asn Arg Gly Thr Ser Gly Ile Ile Ser
                435                 440                 445
Met Thr Phe Leu Ser Leu Tyr Lys Ala Ile Ser Ile Ala Gly Ala Phe
450                 455                 460
Tyr Leu Phe Ala Ala Ile Ala Gly Val Ala Trp Ile Phe Ile Phe Thr
465                 470                 475                 480
Leu Leu Pro Glu Thr Gln Gly Arg Ser Leu Glu Glu Met Gly Leu Leu
                485                 490                 495
Phe Gly Thr Tyr Phe Gly Trp Arg Lys Thr Leu Lys Gly Leu Lys Asn
                500                 505                 510
Arg Glu Ala Glu Glu Ala Lys Asn Ala Asn Val Ile
                515                 520

<210> SEQ ID NO 33
<211> LENGTH: 1849
<212> TYPE: DNA
<213> ORGANISM: Apium graveolens

<400> SEQUENCE: 33
caatgtagga tattattagc ctcatctgca acaaactctt tactagtatt gctctcactc        60
tcctttattt tctctcttct aaatatgacc ggagcttcta tgattaccgg cgaagtttcc       120
gtcgattcat atgatactaa caagcctaaa cctaaaagga ataagtatgc ttttgcttgt       180
gctcttttag cttccatgaa ttccatctta ctcggctatg acaccggagt gttgagtgga       240
gcatcaatat acataaagga agatctccat ttctccgacg ttcaaatcga ataatcatc        300
ggaatcatca acatctactc tcttcttggt tcggccatag ccggaaggac ctcggactgg       360
ataggcagac gttacaccat ggtactagct ggtatcatat tttttctagg agccattttc       420
atggggcttg ctacaaactt tgcctttctc atgtttggtc gctttgttgc tggaattggt       480
gtcggttatg ccatgatgat cgctcccgtc tacactgccg aggttgctcc gtcgtcttcc       540
cgtggtttcc tcacttcttt tcctgaggtt ttcattaatt ctggtgtgtt gctcgggtat       600
gtatccaact ttgcatttgc caagtgccca ctttggttag ctggagaat tatgctggga       660
attggagcat tccttcagt tgccttggcc ataattgtgt tatatatgcc agagtcccca       720
cgttggctcg ttatgcaggg tcgacttggt gaagcgagga ctgtacttga gaaaacttct       780
acttccaaag aagaagctca ccaaagactg tctgatatta aggaagctgc tgggattgat       840
```

```
aaagattgta atgacgatgt tgttcaagtt ccaaaacgta ccaaagacga agcagtgtgg      900
aaagaattga ttcttcaccc tacaaaacct gttcgccacg ctgcaattac gggtattggt      960
attcatttct tccaacaggc ttgtggtatt gatgctgttg ttttatacag ccctcgaatt     1020
tttgaaaaag ctggtatcaa aagtaatagt aaaaagctcc ttgcgacaat tgctgttgga     1080
gtctgcaaaa cagtctttat tctgatatca acgtttcagc tggacaaaat tggacgacgc     1140
cccctgatgc taacaagtat gggggtatg gttattgctc tatttgtact ggcaggctca      1200
ttgacggtta ttaacaaatc acatcatact ggtcattggg ctggtggttt ggcaatattt     1260
acagtgtatg cttttgtgtc gatattttca agtggcatgg gtccaattgc ttgggtctat     1320
agctccgagg tgttcccttt gaggctaaga gctcaaggtt gtagtatcgg agtggcagtt     1380
aaccgtggca tgagtggcat aattggaatg acatttatat cgatgtacaa agccatgact     1440
attggtggtg cattccttt atttgctgtg gttgcatcta tcggatgggt ctttatgtac      1500
acaatgttcc ccgagacaca aggtagaaat ctcgaagaaa ttgagttatt gtttggcagc     1560
tactttggct ggaggaagac attgaaggat ttgaaggcaa agaagctgc tgaagcaaag      1620 agtcgcgaga gtgaagttta gcagtcagat gaatttaggg ttcaaagatg ttatattagc     1680
tctgtgtaga gggtagtttt agagaagccc ttagtatgtg ttggagtatg tgtgattatt     1740
aaccatcacc cgataattta gaataagggt gtcaaagaac aattacccat ttcttatgtg     1800
gtaatctatt gaaaagaatt tgcccaatgg taaaaaaaa aaaaaaaa                  1849

<210> SEQ ID NO 34
<211> LENGTH: 1781
<212> TYPE: DNA
<213> ORGANISM: Apium graveolens

<400> SEQUENCE: 34
tcggcaccag atcacactcc atgttcatgt gccacattgt accctaaaac agtacttagc       60
tcttcatctc tcttaaagat ggctggagct ttcaatgttt ccggtgacga ttccggcggc      120
tctaaagatg taggatcacc tgtaatattt gatgctgtca agaaacctaa acgaaataaa      180
tatgcttttg gttgcgctat tttagcttcc atgacttccg ttttgcttgg ttatgatatt      240
ggagtgatga gtggagcagc aatttacata aaagatcagc tccatgtgtc ggacgtaaaa      300
ctggagattg ttgtcggaat aattaacttc ttttcacttg ttgggtctgc tcttgccgga     360
agaacctccg actggattgg caggcgttac acaatggtgc tagccggtgc tatatttttt     420
gttggagcaa tacttatggg atttgcaacc aactattcat ttctgatgtt tggtcgattc     480
gtcgccggaa tcggagtagg ttatgccctc atgattgctc cggtgtacac ggccgaggtt     540
tcttcagcat catctcgtgg atttcttact tcattcccgg aagttttcat taatatcggt     600
gtactgctcg atatgtctc gaattatgca ttttccaaac tccctgccaa cttgggctgg     660
cgattcatgc ttgaatcgg agcaataccct tcaatcggtt tagcgattgg tgtcctaggc    720
atgcccgaat cacctcgttg gctcgtcatg aaaggccgtc tcggcgaagc tagacaagtc     780
ctagacaaaa cctcagattc caaagaagaa tctcgcctta gattatccga catcaaacag     840
gctgctggca tacccgaaga atgcaacgac gatatcgttg taatgcctaa acggaggaat     900
gacgaggcag tgtggaaaga gttgcttctc catcctacac catcagtccg tcacgcgttc     960
attgctggcg ttggtctaca ttttttccaa caatcaagtg gcatagacgc tggtggtttg    1020
tacagtcctc gaattttcga aaaggctgga atcacgagta ccgacttaaa actgctagca    1080
acaatagctg ttggaatctc gaagacactc ttcatcctag tagctacatt tttactcgat    1140
```

-continued

| | |
|---|---|
| cgaatcggac gacgtccatt gcttctcaca agcatgggag gaatgatcat atccttaact | 1200 |
| ctcctgggaa catccttggc tgttattgac cactcagatc acacagttca ttgggccgtg | 1260 |
| gcattggcaa tcttcggagt tttagcatac gtgggcacgt tttctattgg ctagggcca | 1320 |
| attgcatggg gttatagttc agaggtgttc ccattacgac taagggccca aggatgtagc | 1380 |
| attggagtag ctgttaacag gggtacaagt ggaattatct cgatgacatt tttgtcgcta | 1440 |
| tacaaagcca taagtatagc aggggcattc tatttatttg cagctattgc aggagtggca | 1500 |
| tggatattta tattcacatt acttcctgaa acacaaggga ggagccttga agaaatgggg | 1560 |
| ttactgtttg gaacctattt tggttggaga aaaactttga aggtttgaa gaacagagaa | 1620 |
| gctgaggaag ctaaaaatgc taatgtcata tagaaagttt atatttgtca agtatgggta | 1680 |
| gtctacttta tatgactctg ttaccggtac ataattttgt aaaataatgt gaattcggga | 1740 |
| acaaatccat gtgtgatgag accaaaaaaa aaaaaaaaaa a | 1781 |

<210> SEQ ID NO 35
<211> LENGTH: 1908
<212> TYPE: DNA
<213> ORGANISM: Apium graveolens

<400> SEQUENCE: 35

| | |
|---|---|
| ccctcacgtt acgatagtca aattgtttag tcctttcccc caagcttcga ccattgtttc | 60 |
| tcaacatttt gtaatctctc tctctctcga tggccggaac ttctggccct tccggcggtg | 120 |
| tcgtcgccga tcccaagaat ctgagttcac ctttatttga cgcggagaaa aaacccaaaa | 180 |
| ataacaagta tgcttttgct tgttccattt tagcttccat gacttcaatt ctacttggtt | 240 |
| atgatacggg ggttatgagt ggagcagcaa tctacataaa aaaagatctc cgtttcaccg | 300 |
| atgtacaaat cgaaatcatc gtcggaatca tcaacatctt ctctcttctc ggctcttttc | 360 |
| tcgccggaag aacctccgat tggattggcc ggagatacac aatggttcta gccggtggca | 420 |
| tattttttgc cggagctttt ttaatgggat gtgctacaaa ctttgagttt ttaatggtgg | 480 |
| gtcggtttgt cgccgggatc ggagtagggt atgctatgat gatcgctccg gtttatacaa | 540 |
| ctgaggttgc tccggcgtct tctcggggtt ttctcacttc tttcccggag gtctttatta | 600 |
| atgctggagt tatgctgggg tatgtatcca actttgcatt tgcaaagctt ccgctttggt | 660 |
| taggctggag gttatgctt ggaattggag cagttccttc ggttggctta gccattggtg | 720 |
| tattgtatat gcctgagtct ccgcgttggc ttgtcatgag gggtcaactt ggcgaagcaa | 780 |
| ggcgtgtact ggaaaagact tcggagagca agaagaagc tcgacaaaga ctagaagata | 840 |
| tcaaggaggc tgctggaatt ccagaagaat gtaatgatga cgttgttgaa gttcctaaac | 900 |
| gtagcaaaga cgatgctgtg tggaaagaat tgttccttca tcctacacca gctgttcgcc | 960 |
| atgctgctat cactggcatt ggtattcatt tcttccaaat ggctagtggt gttgatgctg | 1020 |
| ttgttttgta cagtcctcga attttgaga aggctgggtt aaagagtgat aaccacaagc | 1080 |
| tactcgccac cattggtgtt ggagtctgca aaactatttt tgttttgata tcaacatttt | 1140 |
| tgctagacaa agtcggacgg cgcccactga tgctttcgag tatggggggc atggtaattg | 1200 |
| ctctactcgt actctcaggc tcattgtctg taattaatca ctcgcatcaa accgttccct | 1260 |
| gggctgttgc tttggcaata atttcggtgt atggctttgt gtcggtgttt tcaagtggga | 1320 |
| tggggccaat tgcttgggtg tatagttcgg aggtgtttcc tttgaggctt agagcccaag | 1380 |
| gttgcagtat cggagtggca gtcaatcgtg tgttagtgg cattatcgga atgacattta | 1440 |
| tatcaatgta caaggccttg actattggtg gtgcattctt tgtattcgct gtggttgcag | 1500 |

```
caattggatg ggtattcatg ttcacaatgt ttcctgaaac tcaaggaaga aatcttgaag    1560
aaattgaggt attgtttggc agttactttg gctggaggaa aacattgaag gatttgaaga    1620
agaaagaagc ggcagaagca aagaatgtct gcattgttgc ttaaaattca aatacagcgg    1680
ggattatagc tttgtgatgt taaatgtgtt tgagcgaggg tgcaaaacca aacatacccg    1740
gtatattcac tcctaagtag aatttctgga gtacctgcgg atttgtttgt gttaactaag    1800
ggcgatttta tcaaaatcct tggtacccct ggaactcctc taataaattt aaaacagtat    1860
tgtggttttt acttgaaaaa aaaaaaaaaa aaaaaaaaa aaaaaaa                   1908

<210> SEQ ID NO 36
<211> LENGTH: 50
<212> TYPE: DNA
<213> ORGANISM: Artificial
<220> FEATURE:
<223> OTHER INFORMATION: Primer

<400> SEQUENCE: 36
ggggacaagt ttgtacaaaa aagcaggctg aacagaaaca attgtggatg              50

<210> SEQ ID NO 37
<211> LENGTH: 19
<212> TYPE: DNA
<213> ORGANISM: artificial
<220> FEATURE:
<223> OTHER INFORMATION: Primer

<400> SEQUENCE: 37
cgatccagac tgaatgccc                                                19

<210> SEQ ID NO 38
<211> LENGTH: 50
<212> TYPE: DNA
<213> ORGANISM: artificial
<220> FEATURE:
<223> OTHER INFORMATION: Primer

<400> SEQUENCE: 38
ggggacaagt ttgtacaaaa aagcaggctg acccactatc aacaatgatc              50
```